(12) United States Patent
Hermez et al.

(10) Patent No.: US 10,384,030 B2
(45) Date of Patent: Aug. 20, 2019

(54) MEDICAL COMPONENTS WITH MICROSTRUCTURES FOR HUMIDIFICATION AND CONDENSATE MANAGEMENT

(71) Applicant: FISHER & PAYKEL HEALTHCARE LIMITED, Auckland (NZ)

(72) Inventors: Laith Adeeb Hermez, Auckland (NZ); David John Sims, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 810 days.

(21) Appl. No.: 14/775,007

(22) PCT Filed: Mar. 14, 2014

(86) PCT No.: PCT/NZ2014/000036
§ 371 (c)(1),
(2) Date: Sep. 11, 2015

(87) PCT Pub. No.: WO2014/142677
PCT Pub. Date: Sep. 18, 2014

(65) Prior Publication Data
US 2016/0015926 A1    Jan. 21, 2016

Related U.S. Application Data

(60) Provisional application No. 61/920,423, filed on Dec. 23, 2013, provisional application No. 61/785,895, filed on Mar. 14, 2013.

(30) Foreign Application Priority Data

Jun. 25, 2013  (WO) ................ PCT/NZ2013/000113

(51) Int. Cl.
*A61M 16/00*  (2006.01)
*A61M 16/08*  (2006.01)
(Continued)

(52) U.S. Cl.
CPC ...... *A61M 16/0808* (2013.01); *A61M 16/024* (2017.08); *A61M 16/06* (2013.01);
(Continued)

(58) Field of Classification Search
CPC ............ A61M 16/0808; A61M 16/145; A61M 16/0883; A61M 16/06; A61M 16/0875;
(Continued)

(56) References Cited

U.S. PATENT DOCUMENTS 1,813,959 A * 7/1931 Romanoff ............... F24F 6/025
261/119.1
3,110,748 A    11/1963 Myklebust
(Continued)

FOREIGN PATENT DOCUMENTS

CN     1489521       4/2004
CN     1652923 A     8/2005
(Continued)

OTHER PUBLICATIONS

International Search Report; PCT/NZ2013/000113, dated Aug. 15, 2013, in 4 pages.
(Continued)

*Primary Examiner* — Steven O Douglas
(74) *Attorney, Agent, or Firm* — Knobbe, Martens, Olson & Bear, LLP

(57) ABSTRACT

New medical circuit components and methods for forming such components are disclosed. These components include microstructures for humidification and/or condensate management. The disclosed microstructures can be incorporated into a variety of components, including tubes (e.g., inspiratory breathing tubes and expiratory breathing tubes and other tubing between various elements of a breathing circuit, such as ventilators, humidifiers, filters, water traps, sample lines, connectors, gas analyzers, and the like), Y-connectors,
(Continued)

catheter mounts, humidifiers, and patient interfaces (e.g., masks for covering the nose and face, nasal masks, cannulas, nasal pillows, etc.), floats, probes, and sensors in a variety of medical circuits.

25 Claims, 44 Drawing Sheets

(51) Int. Cl.
*A61M 16/16* (2006.01)
*A61M 16/06* (2006.01)
*A61M 16/10* (2006.01)

(52) U.S. Cl.
CPC ...... *A61M 16/0875* (2013.01); *A61M 16/109* (2014.02); *A61M 16/16* (2013.01); *A61M 16/165* (2014.02); *A61M 16/1095* (2014.02); *A61M 2205/0244* (2013.01); *A61M 2205/3653* (2013.01); *A61M 2206/14* (2013.01); *A61M 2206/20* (2013.01)

(58) Field of Classification Search
CPC .. A61M 16/109; A61M 16/165; A61M 16/16; A61M 2205/0244; A61M 2206/14; A61M 2205/3653; A61M 16/1095; A61M 2206/20
See application file for complete search history.

(56) References Cited

U.S. PATENT DOCUMENTS

| | | | |
|---|---|---|---|
| 3,283,478 A | 11/1966 | Katzman et al. | |
| 4,110,419 A | 8/1978 | Miller | |
| 5,445,143 A * | 8/1995 | Sims | A61M 16/167 128/203.26 |
| 5,607,627 A | 3/1997 | Berkeley et al. | |
| 5,955,006 A * | 9/1999 | Charnecky | F24D 19/0082 261/66 |
| 5,996,976 A * | 12/1999 | Murphy | B01D 53/22 261/104 |
| 6,398,197 B1 * | 6/2002 | Dickinson | A61M 16/16 261/119.1 |
| 6,531,206 B2 | 3/2003 | Johnston et al. | |
| 8,181,938 B2 | 5/2012 | Payne et al. | |
| 8,347,909 B2 * | 1/2013 | Zollinger | A61M 16/168 128/205.24 |
| 2006/0012057 A1 | 1/2006 | Johnston | |
| 2007/0107879 A1 | 5/2007 | Rodomski et al. | |
| 2009/0000620 A1 | 1/2009 | Virr | |
| 2009/0038614 A1 | 2/2009 | Kuo et al. | |
| 2011/0309157 A1 | 12/2011 | Yang et al. | |

FOREIGN PATENT DOCUMENTS

| | | |
|---|---|---|
| CN | 102753229 A | 10/2012 |
| DE | 10 2005 005349 | 6/2006 |
| EP | 0589429 | 3/1994 |
| EP | 1586345 | 10/2005 |
| EP | 1733751 | 12/2006 |
| EP | 2340867 | 7/2011 |
| JP | 63-065452 U | 4/1988 |
| JP | 06-000453 U | 1/1994 |
| JP | 06-235538 | 8/1994 |
| JP | 2004-533564 | 11/2004 |
| JP | 2008-545943 | 12/2008 |
| WO | WO 2003/099367 | 12/2003 |
| WO | WO 2004/112873 | 12/2004 |
| WO | WO 2005/018724 | 3/2005 |
| WO | WO 2006/124757 | 11/2006 |
| WO | WO 2007/019626 | 2/2007 |
| WO | WO 2008/095245 | 8/2008 |
| WO | WO 2011/042212 | 4/2011 |
| WO | WO 2011/077250 | 6/2011 |

OTHER PUBLICATIONS

European Search Report, PCT/NZ2013/000113, dated Dec. 15, 2015, in 6 pages.
Chinese Exam Report, CN Application No. 201380042710.4, dated Feb. 1, 2016, in 16 pages.
International Search Report; Application No. PCT/NZ2014/000036; filed Mar. 14, 2014.
Chinese Second Office Action re Application No. 2013800427104 dated Oct. 24, 2016 (10 Pages).

* cited by examiner

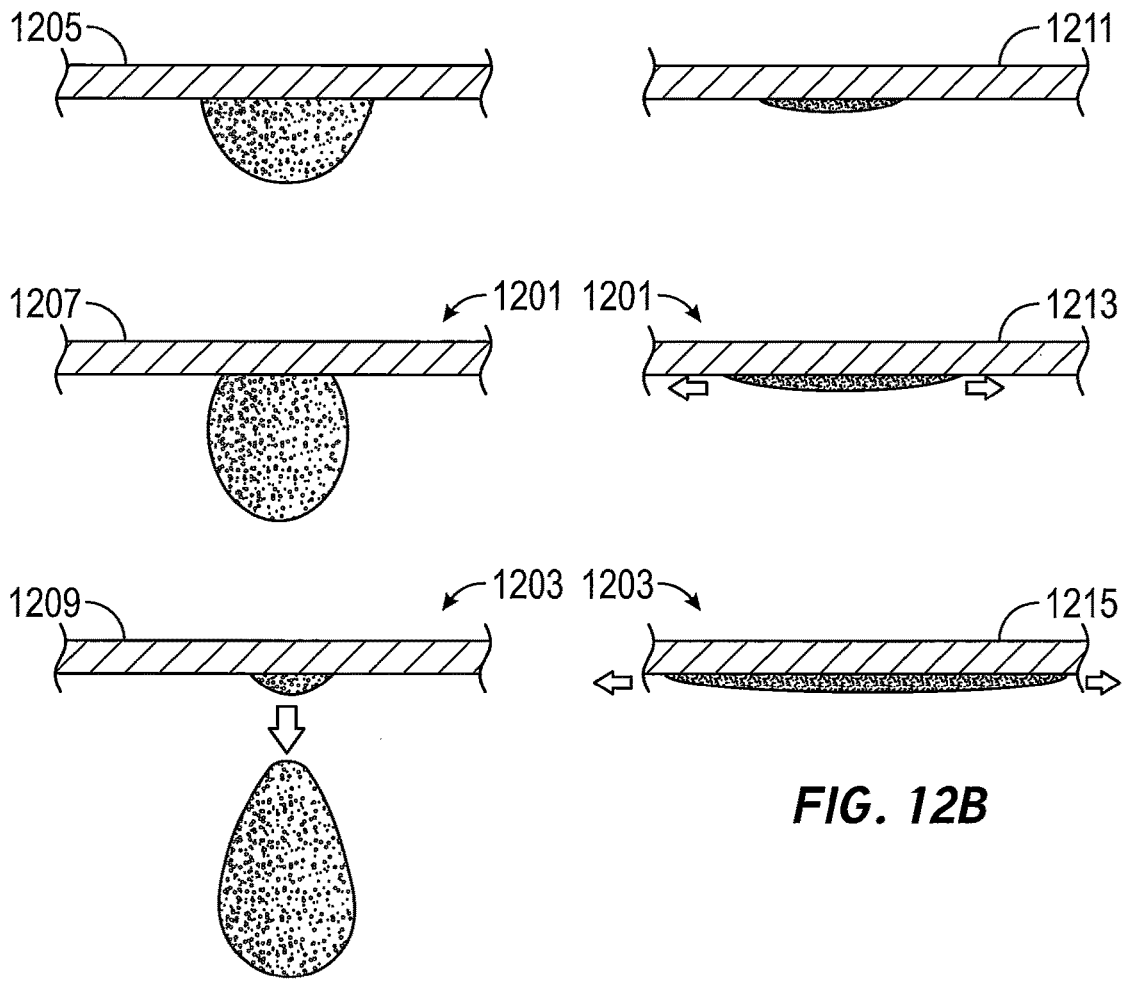
FIG. 12A
FIG. 12B
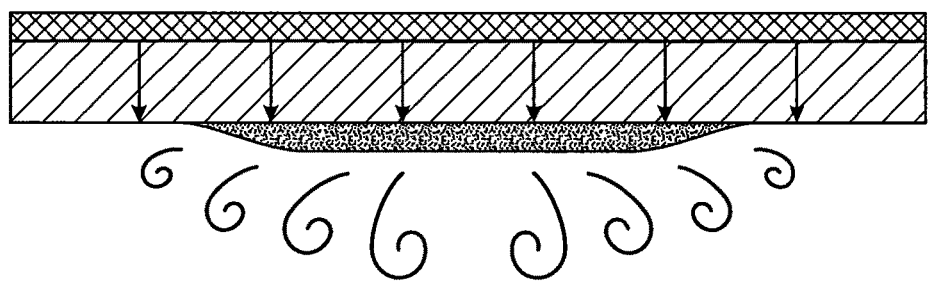
FIG. 13

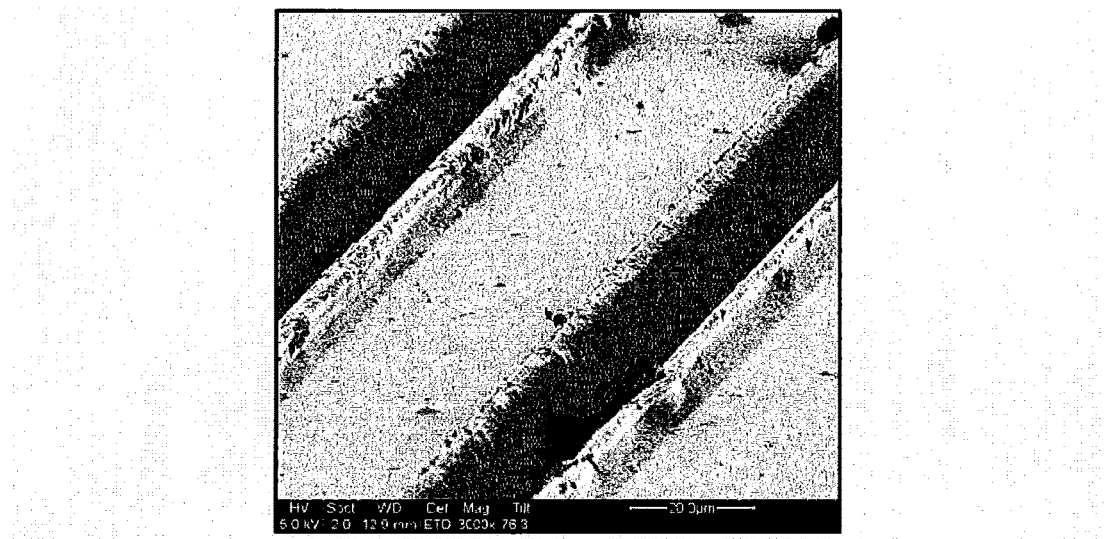
FIG. 18A
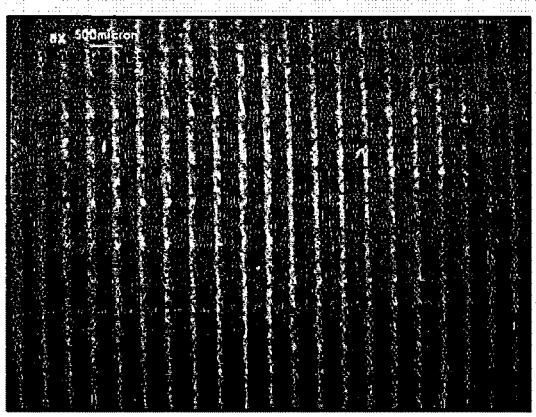 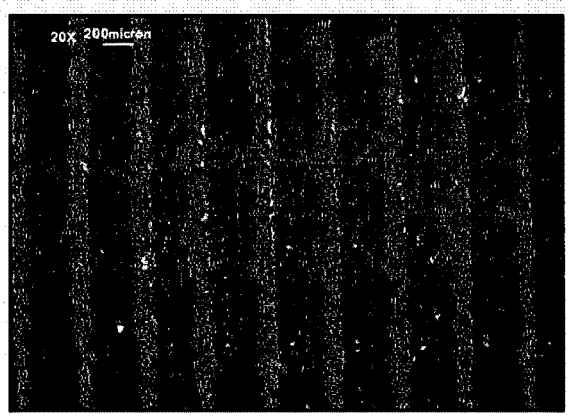
FIG. 18B  FIG. 18C

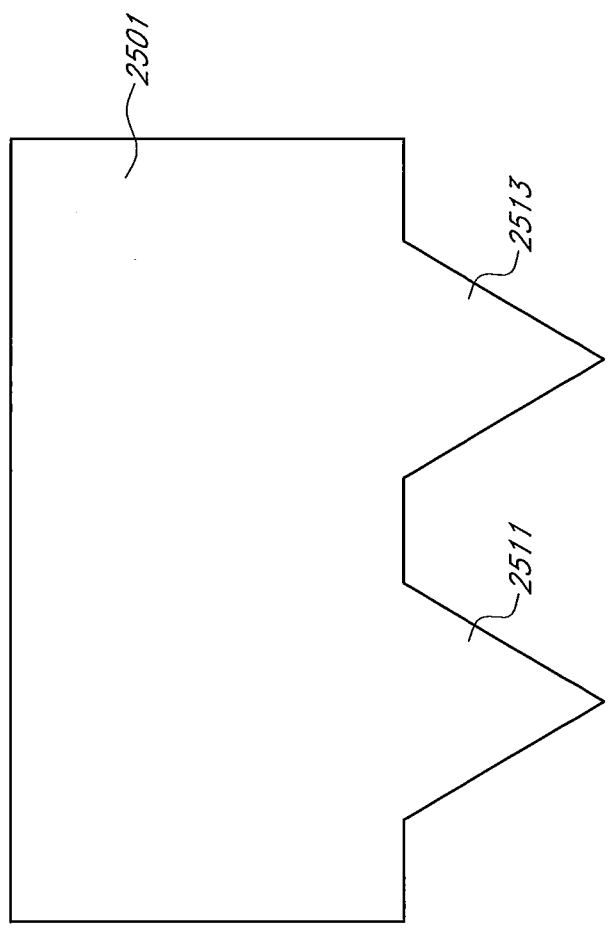

MEDICAL COMPONENTS WITH MICROSTRUCTURES FOR HUMIDIFICATION AND CONDENSATE MANAGEMENT

CROSS-REFERENCE TO RELATED APPLICATIONS

This application claims the benefit of U.S. Provisional Application No. 61/785,895, entitled "MEDICAL COMPONENTS WITH MICROSTRUCTURES FOR HUMIDIFICATION AND CONDENSATE MANAGEMENT," filed Mar. 14, 2013; International Application No. PCT/NZ2013/000113, entitled "MEDICAL COMPONENTS WITH MICROSTRUCTURES FOR HUMIDIFICATION AND CONDENSATE MANAGEMENT," filed Jun. 25, 2013; and U.S. Provisional Application No. 61/920,423, "MEDICAL COMPONENTS WITH MICROSTRUCTURES FOR HUMIDIFICATION AND CONDENSATE MANAGEMENT," filed Dec. 23, 2013, each of which is incorporated by reference herein in its entirety.

BACKGROUND

Field

This disclosure relates generally to components suitable for medical use and more specifically to components that suitable for providing humidified gases to and/or removing humidified gases from a patient, such as in positive airway pressure (PAP), respirator, anesthesia, ventilator, and insufflation systems.

Description of the Related Art

In medical circuits, various components transport naturally or artificially humidified gases to and from patients. For example, in some breathing circuits such as PAP or assisted breathing circuits, gases inhaled by a patient are delivered from a respiratory humidifier through an inspiratory tube to a patient interface, such as a mask. As another example, tubes can deliver humidified gas (commonly $CO_2$) into the abdominal cavity in insufflation circuits. This can help prevent "drying out" of the patient's internal organs, and can decrease the amount of time needed for recovery from surgery.

In these medical applications, the gases are preferably delivered in a condition having humidity near saturation level and at close to body temperature (usually at a temperature between 33° C. and 37° C.). Condensation or "rain-out" can form on the inside surfaces of components as high humidity gases cool. A need remains for components that allow for improved humidification and condensate management in medical circuits. Accordingly, an object of certain components and methods described herein is to ameliorate one or more of the problems of prior art systems, or at least to provide the public with a useful choice.

SUMMARY

Medical components with microstructures for humidification and/or condensate management and methods of manufacturing such components are disclosed herein in various embodiments.

In at least one embodiment, a component for use in a medical circuit comprises a first region that, in use, contacts liquid; a second region that is distinct from the first region; and a microstructured surface in communication with the first region and the second region configured, in use, to wick liquid from the first region to the second region, wherein the microstructured surface comprises a substrate having an equilibrium contact angle less than about $\pi/2$ radians.

In various embodiments, the foregoing component has one, some, or all of the following properties, as well as properties described elsewhere in this disclosure.

The second region, in use, can be exposed to higher velocity air and the first region, in use, can be exposed to lower velocity air. The second region can be configured to communicate with a heat source. The microstructured surface can be configured to communicate with a heat source. The microstructured surface can comprise generally parallel microchannels.

The microstructured surface can comprise generally inverse-trapezoid-shaped structures, each including a first ridge and a second ridge having similar dimensions that project from the surface and defining a first channel therebetween. The height of the first and second ridge can be in the range of about 30 and about 200 µm.

The generally inverse-trapezoid-shaped structures can comprise a second channel within the within the first channel and adjacent the first ridge and a third channel within the first channel and adjacent the second ridge, the second and third channels having similar dimensions and being recessed from the first channel. The depth of the second and third channel can be in the range of about 5 and about 10 µm. The height of the first channel can be in the range of about 2 and about 5 tunes taller than the depth of the second and third channels. The height of the first channel can be in the range of about 2 and about 3 times taller than the depth of the second and third channels. The height of the first channel can be in the range of about 3 and about 5 times taller than the depth of the second and third channels. The height of the first channel can be in the range of about 3 and about 5 times taller than the depth of the second and third channels.

The critical contact angle θ for the generally inverse-trapezoid-shaped structures can satisfy the equation:

$$\theta < \arccos\left(\frac{\lambda\cos\phi + 2\sin\phi}{\lambda\cos\phi + 2}\right)$$

where λ is the ratio of the cross-sectional width of the base of the first channel to the cross-sectional height of the ridges, measured from the base of the first channel, and φ is the angle between the vertical axis and a side of the first or second ridge.

The microchannels can be generally square-shaped. The critical contact angle θ for the microchannels can satisfy the equation:

$$\theta < \arccos\left(\frac{0.5}{0.5 + X}\right)$$

where X represents the height-to-width aspect ratio for the square shaped channels. The microchannels can be generally v-shaped. The critical contact angle θ of the microchannels can satisfy the equation:

$$\theta < \arccos\left(\sin\left(\frac{\beta}{2}\right)\right)$$

where β represents the angle of the v-shape. The microstructured surface can comprise micropillars. The micropillars can have substantially the same cross sectional dimensions. At least some of the micropillars can have different cross sectional dimensions from other micropillars. The microstructured surface can comprise inverted trapezoids bounded by microridges.

In various embodiments, the foregoing component can be incorporated in a mask. The mask can further comprise a drain in communication with the second region.

In various embodiments, the foregoing component can be incorporated in a conduit. The component can form at least a portion of an inner wall of the conduit. The component can be an insert in an inner lumen of the conduit. A wall of the conduit can be configured to communicate with a heat source.

In at least one embodiment, a component for use in a medical circuit comprises a reservoir portion configured to hold a liquid; an evaporator portion adjacent the reservoir portion configured to facilitate evaporation of the liquid; and a microstructured surface configured to transport liquid from the reservoir portion to the evaporator portion.

In various embodiments, the foregoing component has one, some, or all of the following properties, as well as properties described elsewhere in this disclosure.

The evaporator portion can be heatable. The microstructured surface can comprise microchannels having an aspect ratio that is lower near the reservoir portion and higher near the evaporator portion the aspect ratio increases along a gradient. The microstructured surface can comprise first microchannels extending generally horizontally near the reservoir portion and second microchannels extending generally vertically near the evaporator portion, wherein the first microchannels are configured to transport liquid to the second micro channels.

In various embodiments, the foregoing component can be incorporated in a mask.

In various embodiments, the foregoing component can be incorporated in a humidification chamber suitable for use with a humidifier. The component can form at least a portion of an inner wall of the humidification chamber. The humidification chamber can comprise walls configured to be heated by a heater base of the humidifier. The humidification chamber can comprise walls configured to be heated by a heating member distinct from the humidifier. The humidification chamber can further comprise insulation disposed at least on or over a wall of the humidification chamber near the evaporator portion.

The humidification chamber can further comprise at least one internal guide wall configured to guide a flow of gases within the humidification chamber. The at least one internal guide wall comprises a plurality of guide walls. The plurality of guide walls can be arranged concentrically. A flow channel can be defined between adjacent ones of the plurality of guide walls. The plurality of guide walls can define multiple flow channels, wherein at least some of the flow channels vary in size relative to one another. The guide wall or guide walls can be generally U-shaped and extend between an inlet port and an outlet port of the humidification chamber. The microstructured surface can form at least a portion of the guide wall or guide walls.

The humidification chamber can further comprise a mixing element within the humidification chamber that facilitates mixing of gaseous and liquid phases of the water. The mixing element can be movable in response to a flow of gas through the humidification chamber. The mixing element can be a turbine comprising a plurality of blades. The component can comprise at least one of the plurality of blades.

The humidification chamber can further comprise a dual valve arrangement that controls the entry of water into the humidification chamber through a water inlet, wherein at least one of the valves is not controlled by a float. A first valve can be controlled by a float and a second valve can be controlled by an actuator arrangement comprising a water level sensor and a valve actuator. The second valve can be normally biased to a closed position and can be moved to an open position by the valve actuator.

The humidification chamber can comprise a planar wall and the water level sensor can be located on the planar wall. The inlet port and the outlet port can be located adjacent the planar wall.

In various embodiments, the foregoing component can be incorporated in a conduit. The microstructured surface can form at least a portion of an inner wall of the conduit. The microstructured surface can be disposed on an insert in an inner lumen of the conduit. A wall of the conduit is configured to communicate with a heat source.

In at least one embodiment, a medical circuit component for use with humidified gas, comprises: a wall defining a space within and wherein at least a part of the wall comprises a surface including a plurality of microchannels in and on a substrate having an outward surface with an equilibrium contact angle less than about $\pi/2$ radians, the microchannels being configured, in use, to wick liquid from a first region holding liquid water to a second region exposed to an air flow to or from a patient, and the microchannels comprising first microchannels having side portions and a bottom portion lower than the outer surface of the substrate and second microchannels having side portions higher than the outer surface of the substrate, wherein the side portions of the second microchannels are formed by ridges around or between the first microchannels.

In various embodiments, the foregoing medical circuit has one, some, or all of the following properties, as well as properties described elsewhere in this disclosure.

The microstructures can be generally inverse-trapezoid-shaped structures, each including a first ridge and a second ridge having similar dimensions that project from the surface and defining a first channel therebetween. The height of the first ridge and the second ridge can be in the range of about 30 and about 40 μm. The generally inverse-trapezoid-shaped structures can comprise a second channel within the within the first channel and adjacent the first ridge and a third channel within the first channel and adjacent the second ridge, the second and third channels having similar dimensions and being recessed from the first channel. The depth of the second and third channel can be in the range of about 5 and about 10 μm. The height of the first channel can be in the range of about 2 and about 5 times taller than the depth of the second and third channels. The height of the first channel can be in the range of about 2 and about 3 times taller than the depth of the second and third channels. The height of the first channel can be in the range of about 3 and about 5 times taller than the depth of the second and third channels. The height of the first channel can be in the range of about 3 and about 5 times taller than the depth of the second and third channels.

The critical contact angle $\theta$ for the generally inverse-trapezoid-shaped structures can satisfy the equation:

$$\theta < \arccos\left(\frac{\lambda\cos\phi + 2\sin\phi}{\lambda\cos\phi + 2}\right)$$

where λ is the ratio of the cross-sectional width of the base of the first channel to the cross-sectional height of the ridges, measured from the base of the first channel, and φ is the angle between the vertical axis and a side of the first or second ridge.

The first microchannels can be generally square-shaped. The critical contact angle θ for the first microchannels can satisfy the equation:

$$\theta < \arccos\left(\frac{0.5}{0.5 + X}\right)$$

where X represents the height-to-width aspect ratio for the square shaped channels. The first microchannels can be generally v-shaped. The critical contact angle θ of the first microchannels can satisfy the equation:

$$\theta < \arccos\left(\sin\left(\frac{\beta}{2}\right)\right)$$

where β represents the angle of the v-shape.

In some embodiments, a component for use in a medical circuit comprises a generally horizontal, planar microstructured surface configured to disperse a liquid placed thereon. The microstructured surface can be placed in a path of a flowing gas and a liquid dispenser can be configured to dispense the liquid onto the microstructured surface.

In various embodiments, the microstructured surface comprises surface irregularities.

In various embodiments, the surface irregularities comprise at least one of the group consisting of granules, ridges, grooves, channels, and particles.

In various embodiments, the liquid dispenser comprises at least one dropper configured to dispense the liquid one drop at a time on the microstructured surface.

In various embodiments, the liquid dispenser comprises a substantially flat plate positioned a distance above the microstructured surface, the plate including a plurality of holes through which the liquid is able to fall onto the microstructured surface below.

In at least one embodiment, a component for use in a medical circuit comprises a generally horizontal, planar microstructured surface configured to disperse a liquid placed thereon, wherein the microstructured surface is placed in a path of a flowing gas; and a liquid dispenser configured to dispense the liquid onto the microstructured surface.

In various embodiments, the foregoing component has one, some, or all of the following properties, as well as properties described elsewhere in this disclosure.

The microstructured surface can comprise surface irregularities. The surface irregularities can comprise at least one of the group consisting of granules, ridges, grooves, channels, and particles. The liquid dispenser can comprise at least one dropper configured to dispense the liquid one drop at a time on the microstructured surface. The liquid dispenser can comprise a substantially flat plate positioned a distance above the microstructured surface, the plate including a plurality of holes through which the liquid is able to fall onto the microstructured surface below.

In at least one embodiment, a humidification chamber suitable for use with a humidifier comprises an exterior wall defining an interior space and at least one internal guide wall within the interior space and configured to guide a flow of gases within the humidification chamber.

In various embodiments, the foregoing humidification chamber has one, some, or all of the following properties, as well as properties described elsewhere in this disclosure.

The at least one internal guide wall can comprise a plurality of guide walls. The plurality of guide walls can be arranged concentrically. A flow channel can be defined between adjacent ones of the plurality of guide walls. The plurality of guide walls can define multiple flow channels, wherein at least some of the flow channels vary in size relative to one another. The guide wall or guide walls can be generally U-shaped and extend between an inlet port and an outlet port of the humidification chamber. A microstructured surface can form at least a portion of the guide wall or guide walls. The guide wall or guide walls can be attached to a top wall of the humidification chamber.

The humidification chamber can further comprises a mixing element within the humidification chamber that facilitates mixing of gaseous and liquid phases of the water.

In at least one embodiment, a humidification chamber suitable for use with a humidifier comprises an exterior wall defining an interior space; and a mixing element within the humidification chamber that facilitates mixing of gaseous and liquid phases of the water.

In various embodiments, the foregoing humidification chamber has one, some, or all of the following properties, as well as properties described elsewhere in this disclosure. The mixing element can be movable in response to a flow of gas through the humidification chamber. The mixing element can be a turbine comprising a plurality of blades.

The humidification chamber can further comprise a dual valve arrangement that controls the entry of water into the humidification chamber through a water inlet, wherein at least one of the valves is not controlled by a float. A first valve can be controlled by a float and a second valve can be controlled by an actuator arrangement comprising a water level sensor and a valve actuator. The second valve can be normally biased to a closed position and can be moved to an open position by the valve actuator.

The humidification chamber can comprises a planar wall and the water level sensor can be located on the planar wall. The inlet port and the outlet port can be located adjacent the planar wall.

A bottom surface of the turbine can comprise a projection that defines an axis of rotation. The turbine can comprise a base and the plurality of blades can be connectable to the base. The blades can be generally or substantially planar.

In at least one embodiment, a humidification chamber suitable for use with a humidifier comprises an exterior wall defining an interior space; a water inlet that permits water to enter the interior space; a primary valve that controls the entry of water into the humidification chamber through the water inlet, wherein the primary valve is controlled by a float; and a secondary valve that controls entry of water into the humidification chamber through the water inlet, wherein the secondary valve is not controlled by a float.

In various embodiments, the foregoing humidification chamber has one, some, or all of the following properties, as well as properties described elsewhere in this disclosure. The secondary valve can be controlled by an actuator arrangement comprising a water level sensor and a valve actuator. The second valve can be normally biased to a closed position and can be moved to an open position by the valve actuator. The second valve can comprise a valve body assembly having unitary spring arms that normally bias the valve body assembly to a closed position of the second valve. The humidification chamber can comprise a planar wall and the water level sensor can be located on the planar wall. The inlet port and the outlet port can be located adjacent the planar wall.

These and other embodiments are described in greater detail below.

BRIEF DESCRIPTION OF THE DRAWINGS

Example embodiments that implement the various features of the disclosed systems and methods will now be described with reference to the drawings. The drawings and the associated descriptions are provided to illustrate embodiments and not to limit the scope of the disclosure.

FIG. 12A shows a schematic of water droplet formation on an interface surface that does not incorporate microstructures.

FIG. 12B shows a schematic of water spreading on an interface surface that does incorporate microstructures.

FIG. 13 schematically illustrates the effect of added heat on evaporation from microstructures.

FIGS. 18A through 18L show images of continuous and discrete microstructures.

FIGS. 25B and 25C show cutting blades suitable for use in the device of FIG. 25A.

Throughout the drawings, reference numbers frequently are reused to indicate correspondence between referenced (or similar) elements. In addition, the first digit(s) of each reference number indicates the figure in which the element first appears.

DETAILED DESCRIPTION

The following detailed description discloses new medical circuit components and methods for forming such components, such as insufflation, anesthesia, or breathing circuit components. As explained above, these components include microstructures for humidification and/or condensate management. The disclosed microstructures can be incorporated into a variety of components, including tubes (e.g., inspiratory breathing tubes and expiratory breathing tubes and other tubing between various elements of a breathing circuit, such as ventilators, humidifiers, filters, water traps, sample lines, connectors, gas analyzers, and the like), Y-connectors, catheter mounts, humidifiers, and patient interfaces (e.g., masks for covering the nose and face, nasal masks, cannulas, nasal pillows, etc.), floats, probes, and sensors in a variety of medical circuits. Medical circuit is a broad term and is to be given its ordinary and customary meaning to a person of ordinary skill in the art (that is, it is not to be limited to a special or customized meaning). Thus, a medical circuit is meant to include open circuits, such as certain CPAP systems, which can comprise a single inspiratory breathing tube between a ventilator/blower and a patient interface, as well as closed circuits.

Details regarding several illustrative embodiments for implementing the apparatuses and methods described herein are described below with reference to the figures. The invention is not limited to these described embodiments.

Medical Circuit

Figure 1:
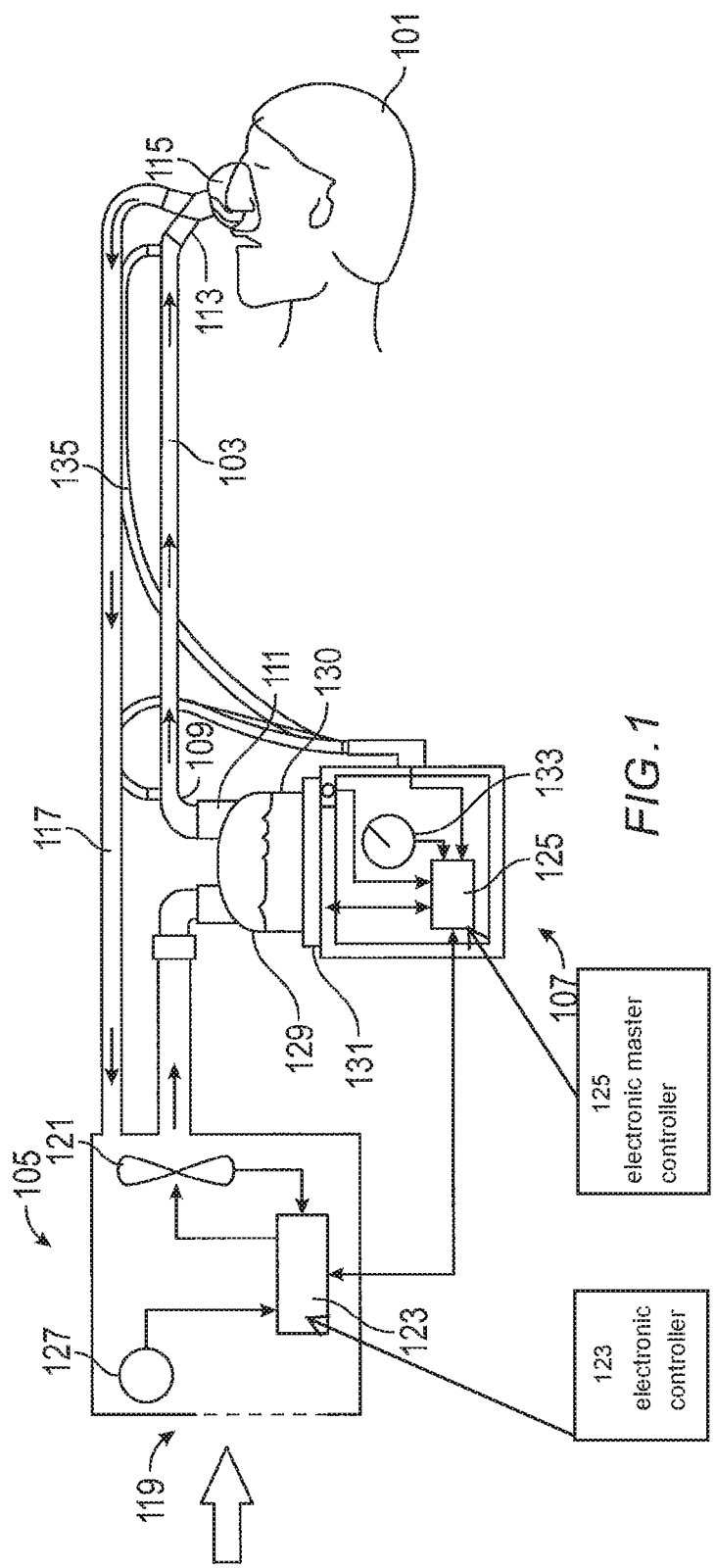
FIG. 1 shows a schematic illustration of a medical circuit incorporating one or more medical tubes, a humidification chamber, and a patient interface.

For a more detailed understanding of the disclosure, reference is first made to FIG. 1, which shows a medical circuit according to at least one embodiment. More specifically, FIG. 1 shows an example breathing circuit. Such a breathing circuit can be, for example, a continuous, variable, or bi-level positive airway pressure (PAP) system or other form of respiratory therapy. As explained below, the breathing circuit includes one or more medical tubes, a humidifier, and a patient interface. Any or all of these components, and other components, of the medical circuit can incorporate microstructures for humidification and/or condensate management. A microstructure generally may be defined as a structure having microscale dimensions in the range of 1 to 1000 microns (μm) (or about 1 to 1000 μm).

Gases can be transported in the circuit of FIG. 1 as follows. Dry gases pass from a ventilator/blower 105 to a humidifier 107, which humidifies the dry gases. In certain embodiments, the ventilator/blower 105 can be integrated with the humidifier 107. The humidifier 107 connects to an inlet 109 (the end for receiving humidified gases) of an inspiratory tube 103 via an outlet port 111, thereby supplying humidified gases to the inspiratory tube 103. An inspiratory tube is a tube that is configured to deliver breathing gases to a patient. The gases flow through the inspiratory tube 103 to an outlet 113 (the end for expelling humidified gases), and then to a patient 101 through a patient interface 115 connected to the outlet 113. In this example, the outlet 113 is a Y-piece adapter. An expiratory tube 117 also connects to the outlet 113. An expiratory tube is a tube that is configured to move exhaled humidified gases away from a patient. Here, the expiratory tube 117 returns exhaled humidified gases from the patient interface 115 to the ventilator/blower 105. The inspiratory tube 103 and/or expiratory tube 117 according to at least one configuration can comprise microstructures. These tubes (and others) are described in greater detail below.

In this example, dry gases enter the ventilator/blower 105 through a vent 119. A fan 121 can improve gas flow into the ventilator/blower 105 by drawing air or other gases through the vent 119. The fan 121 can be, for instance, a variable speed fan, where an electronic controller 123 controls the fan speed. In particular, the function of the electronic controller 123 can be controlled by an electronic master controller 125 in response to inputs from the electronic master controller 125 and/or a user-set value of pressure or fan speed via a dial 127.

The humidifier 107 comprises a humidification chamber 129 containing a volume of water 130 or other suitable humidifying liquid. Preferably, the humidification chamber 129 is removable from the humidifier 107 after use. Removability allows the humidification chamber 129 to be more readily sterilized or disposed. However, the humidification chamber 129 portion of the humidifier 107 can be a unitary construction. The body of the humidification chamber 129 can be formed from a non-conductive glass or plastics material. But the humidification chamber 129 can also include conductive components. For instance, the humidification chamber 129 can include a highly heat-conductive base (for example, an aluminum base) contacting or associated with a heater plate 131 on the humidifier 107. By way of example, the humidifier 107 may be a standalone humidifier, such as any of the humidifiers in the respiratory humidification range of Fisher & Paykel Healthcare Limited of Auckland, New Zealand. An example humidification chamber 129 is described in U.S. Pat. No. 5,445,143 to Sims, which is incorporated by reference in its entirety.

The humidification chamber 129 according to at least one embodiment can comprise microstructures and is described in further detail herein.

The humidifier 107 can also include electronic controls. In this example, the humidifier 107 includes the electronic master controller 125. Preferably, the electronic master controller 125 is a microprocessor-based controller executing computer software commands stored in associated memory. In response to the user-set humidity or temperature value input via a user interface 133, for example, and other inputs, the electronic master controller 125 determines when (or to what level) to energize the heater plate 131 to heat the water 130 within the humidification chamber 129.

Any suitable patient interface 115 can be incorporated. Patient interface is a broad term and is to be given its ordinary and customary meaning to a person of ordinary skill in the art (that is, it is not to be limited to a special or customized meaning) and includes, without limitation, masks (such as tracheal mask, face masks and nasal masks), cannulas, and nasal pillows. A temperature probe 135 can connect to the inspiratory tube 103 near the patient interface 115, or to the patient interface 115. The temperature probe 135 monitors the temperature near or at the patient interface 115. A heating filament (not shown) associated with the temperature probe can be used to adjust the temperature of the patient interface 115 and/or inspiratory tube 103 to raise the temperature of the inspiratory tube 103 and/or patient interface 115 above the saturation temperature, thereby reducing the opportunity for unwanted condensation.

The patient interface 115 according to at least one embodiment can comprise microstructures and is described in greater detail below.

In FIG. 1, exhaled humidified gases are returned from the patient interface 115 to the ventilator/blower 105 via the expiratory tube 117. The expiratory tube 117 can have a temperature probe and/or heating filament, as described above with respect to the inspiratory tube 103, integrated with it to reduce the opportunity for condensation. Furthermore, the expiratory tube 117 need not return exhaled gases to the ventilator/blower 105. Alternatively, exhaled humidified gases can be passed directly to ambient surroundings or to other ancillary equipment, such as an air scrubber/filter (not shown). In certain embodiments, the expiratory tube is omitted altogether.

As discussed above, the inspiratory tube 103, expiratory tube 117, humidification chamber 129, and/or patient interface 115 of the example medical circuit can comprise microstructures. A discussion of these components follows. The invention is not limited by these embodiments, however, and it is contemplated that the disclosed microstructures can be integrated into a variety of medical components that contact and/or transport humidified gases, such as humidified air.

Medical Tube with Microstructures

Figure 2:
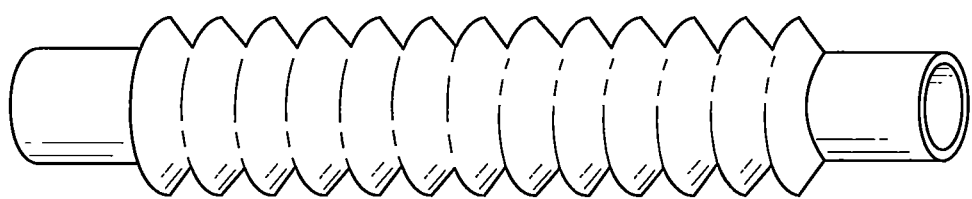
FIG. 2 shows a plan view of an example tube.

FIG. 2 shows a perspective view of a tube 201 suitable for use in a medical circuit, according to at least one embodiment. As shown in FIG. 2, the tube 201 can be corrugated, which advantageously improves the tube's flexibility. However, the tube 201 can have a relatively smooth, non-corrugated wall in certain embodiments.

In certain embodiments, the tube 201 can be used for transporting gases to and/or from infant or neonatal patients. In certain embodiments, the tube 201 can be used for transporting gases to and/or from standard patients, such as older children and adults. Some example dimensions of "infant" and "standard" medical tubes described herein, as well as some preferred ranges for these dimensions, are described in commonly owned U.S. Provisional Patent Application Nos. 61/492,970, filed Jun. 3, 2011, and 61/610,109, filed Mar. 13, 2012, and in commonly owned International Publication No. WO 2011/077250 A1, each of which is incorporated by reference in its entirety. An example length for infant and standard tubes can be 1 to 2 m (or about 1 to 2 m).

In at least one embodiment, the tube 201 is formed from an extrudate comprising one or more polymers. Preferably the polymer is selected so that the resulting tube 201 is generally flexible. Preferred polymers include Linear Low Density Polyethylene (LLDPE), Low Density Polyethylene (LDPE), Polypropylene (PP), Polyolefin Plastomer (POP), Ethylene Vinyl Acetate (EVA), Plasticized Polyvinylchloride (PVC), or a blend of two or more of these materials. The polymer(s) forms at least 98.4 (or about 98.4), 98.5 (or about 98.5), 98.6 (or about 98.6), 98.7 (or about 98.7), 98.8 (or about 98.8), 98.9 (or about 98.9), 99.0 (or about 99.0), 99.1 (or about 99.1), 99.2 (or about 99.2), 99.3 (or about 99.), 99.4 (or about 99.4), 99.5 (or about 99.5), 99.6 (or about 99.6), 99.7 (or about 99.7), 99.8 (or about 99.8), or 99.9 (or about 99.9) weight percent (wt. %) of the total extrudate. In particular embodiments, the extrudate comprises 99.488 (or about 99.488) wt. % or about 99.49 (or about 99.49) wt. % LLDPE. In certain embodiments, the tube 201 is formed from a foamed polymer as described in commonly assigned International Publication No. WO 2001/077250 A1, which is incorporated by reference in its entirety.

In some embodiments, microstructures may be formed of soft metal materials, such as aluminum foil, brass, and copper. In some such embodiments, the materials selected can have a high surface energy. In some embodiments, the substrate materials can be coated and can include an additive that increases the surface energy of the substrate material. In some embodiments, the use of the metal alone without being formed into microstructures may be advantageous simply because of the high surface energy. But microstructures may be formed of the metals, for example, by first forming the soft metal into a film or a thin film and subsequently stamping the material to form microstructures. The stamped material may then be used to form any number of suitable components in the humidification devices of the present disclosure. For example, at least an interior portion of the tube 201 may formed of a metal that may or may not have been stamped to form microstructures. And in some embodiments, a stamped metallic film may form a surface on any number of structures (walls, towers, fins, base, etc.) within a humidification chamber.

In certain embodiments, the tube 201 can comprise one or more conductive filaments. In certain embodiments, the tube 201 can comprise two or four conductive filaments, and pairs of the conductive filaments can be formed into a connecting loop at one or both ends of the tube 201. The one or more filaments can be disposed on the outside of the tube 201, for example, spirally wound around the outside of the tube 201, or disposed on the inner wall of the tube 201, for example, spirally wound around along the lumen wall. Filaments are discussed in greater detail below.

Figure 3A:
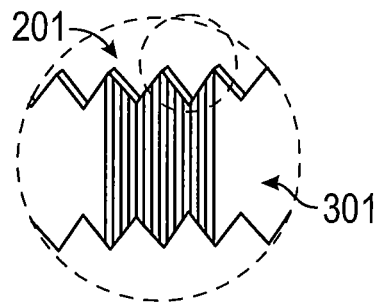
FIGS. 3A and 3B show first and second magnified longitudinal cross sections of an inner component for an example tube according to at least one embodiment.
Figure 3B:
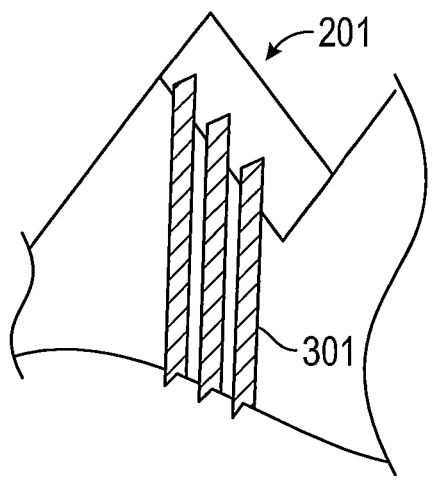

It was discovered that interaction between liquids and surfaces including purpose-built microstructures can result in spreading of the liquid onto the surface and inside or on the microstructures. This interaction was further discovered to increase the liquid-vapor interface area and reduce the thickness of the liquid layer on top of the surface. The combination of increased surface area and reduced thickness improve liquid evaporation, compared to liquid of the same volume of liquid on a flat surface. As discussed below, the combination of increased surface area, reduced thickness, and heating further improves liquid evaporation. Accordingly, in various embodiments, the inner walls of the tube 201 comprise microstructures 301, as shown in FIG. 3A (not to scale). A first magnified view of a portion of the microstructures 301 is shown in FIG. 3B. FIG. 3B shows the microstructures 301 at a greater magnification than FIG. 3A. In FIGS. 3A and 3B, the microstructures 301 are axially disposed along the tube 201 (that is, the microstructures extend in a direction perpendicular to longitudinal length of the tube 201).

Polymers generally have a low surface energy, resulting in poor wettability. In order to improve the water spreading capabilities of the microstructures 301 on a polymer tube 201, it can be advantageous to treat the one or more polymers with a material or materials for increasing the surface energy. Surfactants, such as cationic surfactants, can be particularly desirable additive materials. Suitable surface modifying agents include glycerol monostearate (GMS), ethoxylated amine, alkanesulphonate sodium salt, and lauric diethanolamide and additives comprising these substances. MLDNA-418 supplied by Clariant (New Zealand) Ltd. and under the product name "418 LD Masterbatch Antistatic" is a surface modification agent master batch with 5 (±0.25)% glycerol monostearate (CAS No. 123-94-4) as an active ingredient. Preferably the surface modifying agent comprises at least about 0.05 (or about 0.05), 0.1 (or about 0.1), 0.15 (or about 0.15), 0.2 (or about 0.2), 0.25 (or about 0.25), 0.3 (or about 0.3), 0.35 (or about 0.35), 0.4 (or about 0.4), 0.45 (or about 0.45), 0.5 (or about 0.5), 1.1 (or about 1.1), 1.2 (or about 1.2), 1.3 (or about 1.3), 1.4 (or about 1.4), or 1.5 (or about 1.5) wt. % of the total extrudate. For example, in at least one embodiment, the tube extrudate comprises 0.25 wt. % (or about 0.25 wt. %) of surface modifying agent.

As another example, in at least one embodiment, the tube extrudate comprises 0.5 wt. % (or about 0.5 wt. %) of surface modifying agent.

Other materials, such as other surfactants or other hydrophilizing agents, could also be utilized to improve the water spreading capabilities of the tube 201 or other embodiments. For example, any suitable anionic, cationic or non-ionic surfactants or other hydrophilizing agents, or combinations of such surfactants or hydrophilizing agents can be used. Suitable hydrophilizing agents can be any agent or agents generally capable of increasing the hydrophilic character of a composition. In some configurations, the surfactant or hydrophilizing agent can comprise an ethoxylized fatty alcohol, such as those described in EP 0 480 238 B1, the entirety of which is incorporated by reference herein. In some configurations, the surfactant or hydrophilizing agent can comprise a non-ionic surface-active substance, such as the nonylphenolethoxylates, polyethylene glycol-monoesters and diesters, sorbitan esters, polyethylene glycol-monoethers and diethers and others described in EP 0 268 347 B1, or a non-ionic perfluoralkylated surface-active substance, such as those described in WO 87/03001, the entireties of which are incorporated by reference herein. In some configurations, the surfactant or hydrophilizing agent can contain silicon moieties. In some configurations, the surfactant or hydrophilizing agent can comprise a wetting agent, such as hydrophilic silicon oils as described in the above-mentioned WO 87/03001 and EP 0 231 420 B1, the entirety of which is incorporated by reference herein. In some configurations, the surfactant or hydrophilizing agent can comprise polyether carbosilanes, such as those described in WO 2007/001869, particularly at pages 13 and 14, the entirety of which is incorporated by reference herein. Other such suitable agents are described in U.S. Pat. Nos. 5,750,589, 4,657,959 and EP 0 231 420 B1, as referenced in WO 2007/001869, the entireties of which are incorporated by reference herein. In some configurations, the surfactant or hydrophilizing agent can comprise ethoxylated surfactants containing a siloxane solubilizing group, such as those described in the above-mentioned U.S. Pat. No. 4,657,949 and WO2007/001869. Examples of such ethoxylated surfactants are the SILWET® line of surface active copolymers (e.g., SILWET® L-77) available from Momentive Performance Materials, Inc. of Albany, N.Y. USA and the MASIL® SF19 available from Emerald Performance Materials, LLC of Cuyahoga Falls, Ohio USA.

In certain embodiments, one or more hydrophilizing agents are applied to a microstructured surface after the microstructures are formed. For example, the microstructured surface can be dipped in, sprayed with, or otherwise applied with a suspension of ELVAMIDE® nylon multi-polymer resin (E. I. du Pont de Nemours & Co., Wilmington, Del.) in a volatile solvent, such as methanol or ethanol. The volatile solvent is then allowed to evaporate. After the volatile solvent evaporates, a thin (in the range of 1 µm and 10 µm or in the range of about 1 µm and about 10 µm) layer of ELVAMIDE® resin coats the microstructures, improving the surface hydrophilicity.

Other methods can also be used to increase surface energy. Suitable methods include physical, chemical, and radiation methods. Physical methods include, for example, physical adsorption and Langmuir-Blodgett films. Chemical methods include oxidation by strong acids, ozone treatment, chemisorption, and flame treatment. Radiation methods include plasma (glow discharge), corona discharge, photoactivation (UV), laser, ion beam, electron beam, and gamma irradiation.

By selecting a suitable surface modification method or agent, it is possible to provide a tube wall having surface property contact angles of less than 50 (or about 50), 45 (or about 45), 40 (or about 40), 35 (or about 35), 30 (or about 30), 25 (or about 25), 20 (or about 20) degrees)(°, as measurable by an angle measurement device such as a goniometer. For instance, tube walls having surface property contact angles of less than 35° (or about 35°) provide useful results. Desirably, the contact angle is less than $\pi/2$ (or about $\pi/2$). More desirably, the contact angle is 0° or about 0°.

TABLE 1 below shows contact angle measurements for various LLDPE samples, including a sample treated with a surface-modifying agent and a sample treated with radiation. The contact angle measurements were based on static drop shape testing methods conducted in accordance with ASTM Standard D7334, 2008, "Standard Practice for Surface Wettability of Coatings, Substrates and Pigments by Advancing Contact Angle Measurement."

TABLE 1

| Description of Surface | Liquid | Average Contact Angle (degrees) |
|---|---|---|
| Linear Low-density Polyethylene (LLDPE), as manufactured | Water | 97.39 |
| Linear Low-density Polyethylene (LLDPE), fluorinated, washed | Water | 67.56 |
| Linear Low-density Polyethylene (LLDPE), plasma-treated, 10% $O_2$, 300 Watts, 30 seconds | Water | 44.98 |
| Linear Low-density Polyethylene (LLDPE), with 5% MLDNA-418 as surface modification agent additive | Water | 33.09 |

The sample with 5% MLDNA-418 surface modifying agent produced the lowest measured contact angle compared to other surface modification methods tested.

As discussed above, in certain embodiments, the additive material is added to the bulk polymer extrudate. It can be desirable to add the material in the polymer matrix so that the additive material replenishes the surface for the useful life of the tube. In certain configurations, the material can be added as a surface treatment on the polymer, for example, by coating a surface of the polymer with the material. For example, a microstructured surface can be brushed, sprayed, or otherwise coated with additive material such as HYDRON anti-fog coating (MXL Industries, Lancaster, Pa.), EXXENE anti-fog coatings such as HCAF-100 (Exxene Corporation, Corpus Christi, Tex.), and MAKROLON anti-fog (Bayer Corporation) to produce a thin (e.g., 1 µm or thereabout) coating of additive material. A surface coating can be desirable because of low costs and ease of manufacture.

In certain configurations, a thin film of hydrophilic material such as breathable polyurethanes, for example, ESTANE 58245 (Lubrizol Corporation, Wickliffe, Ohio), breathable polyesters, for example, ARNITEL VT3108 (DSM Engineering Plastics, Sittard, Netherlands), or breathable polyamides, for example PEBAX (Arkema, Colombes, France) can be cast as a surface modifying agent. These hydrophilic materials can absorb moisture and become very wettable. An example method of implementing the hydrophilic thin film includes dissolving the breathable polymer in a solvent, casting the mixture, and allowing the solvent to evaporate, thus leaving a thin film of the breathable material on the microstructures. For instance, ESTANE 58245 pellets can be dissolved in a tetrahydrofuran (THF) of dimethylformamide (DMF) solvent and cast onto microstructures machined from brass or aluminum using a micromilling process. Typical dimensions for the thin film are in the range of 1 to 10 μm (or about 1 to 10 μm). Preferably, the solvent, breathable material, and microstructure material combination is selected such that the microstructure shape and quality is not substantially influenced, for example, by dissolving the microstructures with the solvent.

Certain embodiments include the realization that the perpendicular configuration shown in FIGS. 3A and 3B can advantageously improve humidification and condensate management. As shown in FIG. 1, a tube (e.g., the inspiratory tube 103 or expiratory tube 117) generally extends in a horizontal direction, although certain portions can extend vertically, particularly near the ends of the tube, and some portions can be sloped. Under the action of gravity, condensate tends to run down the vertical and sloped portions of the tube and pool at the lowest points of the generally horizontal tube. When microstructures are perpendicular to the generally horizontal tube bottom, the microstructures will move pooled condensate vertically, against gravity. This action increases the amount of condensate on the tube walls and, thus, the surface area of condensate exposed to the air stream. Exposing a greater surface area of condensate to the air stream increases the likelihood that the condensate will evaporate into the air stream. Therefore, the perpendicular configuration reduces the condensate pooled in the tube and improves the likelihood that the air flowing through the tube maintains a desired level of humidity near saturation.

This configuration can be advantageous because it causes minimal disruption to the airflow within the tube lumen, as there are no structures extending into the lumen. At least one embodiment includes the realization that microstructures do not have to extend into or cover the lumen in order to enhance evaporation.

Figure 19A:
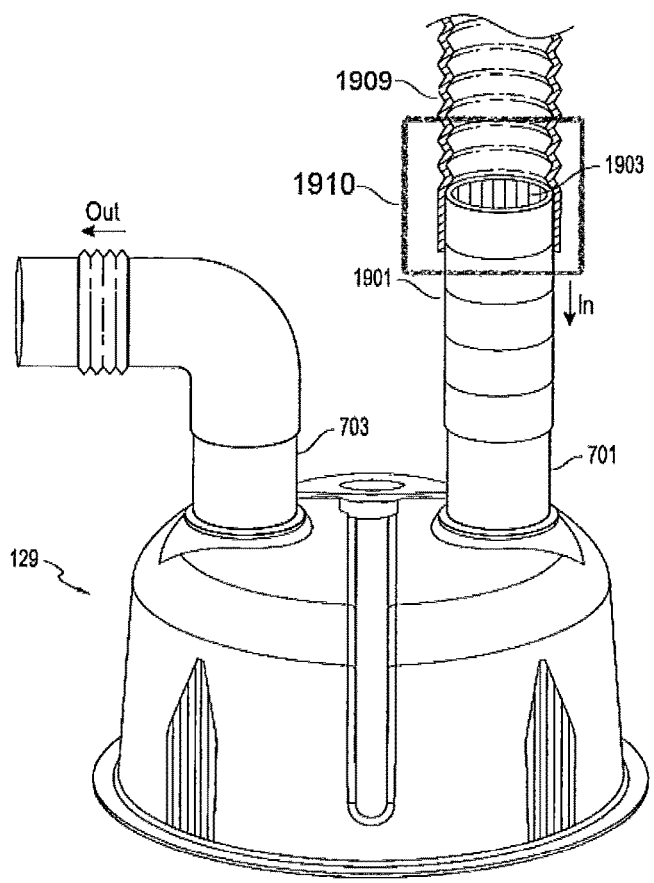
FIG. 19A illustrates a perspective view of a humidification chamber having an inlet tube incorporating microstructures.

FIG. 19A illustrates an embodiment of the humidification chamber 129 to which is attached at an inlet port 701 a tube 1901 incorporating microstructures 1903. The other end of the tube 1901 is connected to a corrugated dry line 1909 leading from a ventilator/blower (not shown). Air flows from the ventilator/blower, into the dry line 1909, through the tube 1901, into the inlet port 901, and then into the humidification chamber 129. Tube 1901 has a non-corrugated wall. A liquid, such as water, can be dispensed into the tube 1901 some distance above the inlet port 701 so that the water runs through and along the microstructures 1903 in the direction of the humidification chamber 129. According to some embodiments, and as shown in FIG. 19A, the microstructures 1903 may be oriented longitudinally in the direction of the tube. The microstructures 1903 may alternatively be oriented in a circumferential direction along the tube wall. The tube 901 of FIG. 19A can advantageously be used to pre-humidify gas flowing into the humidification chamber 129.

In some configurations, the liquid can be metered onto the inner surface of the tube 1901 such that a controlled introduction spreads the liquid around the circumference and, through the use of the microstructures and gravity, along the inner surface of the tube 1901. The introduction of liquid can be controlled using any suitable rate limiting device, such as a flow restrictor. The rate of water flowing into the tube 1901 may be regulated using the rate limiting device to maximize the interplay between the water and the microstructures 1903 in the tube 1901. For example, increasing the amount of water in the tube 1901 may increase the amount of evaporation that occurs. However, the microstructures 1903 may be most effective if not completely covered or coated in water. It has been found that evaporation occurs on a rough surface primarily along the edges of the water and the surrounding structure. Accordingly, it may be desirable to control the amount of water flowing through the tube 1901 so as to maximize the number of edges against the water.

Figure 19B:
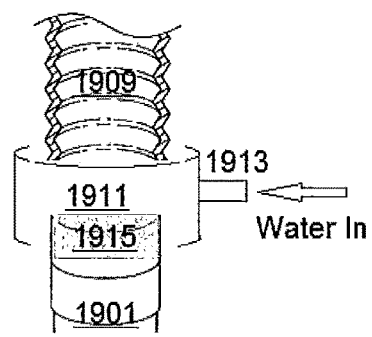
FIG. 19B illustrates a side plan view of a pre-humidification collar for use with the inlet tube.

FIG. 19B shows an example means for delivering liquid to the tube 1901 in the region of box 1910 of FIG. 19A. A liquid supply tube (not shown) provides liquid to a collar 1911 via input 1913, and the collar 1911 supplies liquid to the tube 1901. An optional rate limiting device (not shown), as described above, can be used to regulate the flow of liquid to the collar 1911. For example, in some embodiments, the liquid supply tube can extend between the rate limiting device and the collar 1911. The collar 1911 optionally can include microchannels on an outer surface of a sleeve 1915, which microchannels can be in fluidic communication with the microchannels on the tube 1901. Moreover, the collar 1911 can include a port to which the dry line 1909 can connect. Air flowing down or through the tube 1901 toward the humidification chamber 129 begins to evaporate and carry away the water from the inner surface of the tube 1901. Thus, the air reaching the humidification chamber 129 has already acquired at least some water vapor.

In some embodiments, a heater wire 1907 can be incorporated onto or into the tube 1901. The heater wire 1907 of FIG. 19A is shown in schematic representation on the outside (or outer surface) of the tube 1901. Alternatively (or in addition), the heater wire 1907 can be disposed within the tube 1901 (e.g., within the tube lumen or on the lumen wall) and/or embedded in the tube 1901 wall. A heat jacket (not shown) may also be incorporated into, or may surround, at least a portion of the tube 1901. The heat jacket can further enhance the evaporation of the water or liquid into the flowing gas. In some embodiments, rather than having a heat jacket or in addition to having a heat jacket, the tube 1901 can have heaters printed onto one or more portion of the tube 1901. In some embodiments, the tube 1901 can include structures such as thick film heating elements, etched foil or wire elements to provide a heating element.

The tube 1901 with the microstructures 1903 may be formed in any suitable manner and using any suitable materials. In some embodiments, the tube 1901 can be formed of a corrugated sheet formed from a hydrophilic polymer. Once formed, the corrugated material can be wrapped to form the tube 1901 with the microstructures 1903 running at least a portion of the length of the inner surface of the resulting structure. In some embodiments, the microstructures 1903 are V-shaped trenches. In some embodiments, the V-shaped trenches comprise troughs that are about 30 μm apart from neighboring troughs when the sheet is laid out flat. In some configurations, the sheet, and therefore the resulting tube 1901, may be about 150 mm long and, once folded to form the tube 1901, may have a diameter of about 20 mm.

Figure 37A:
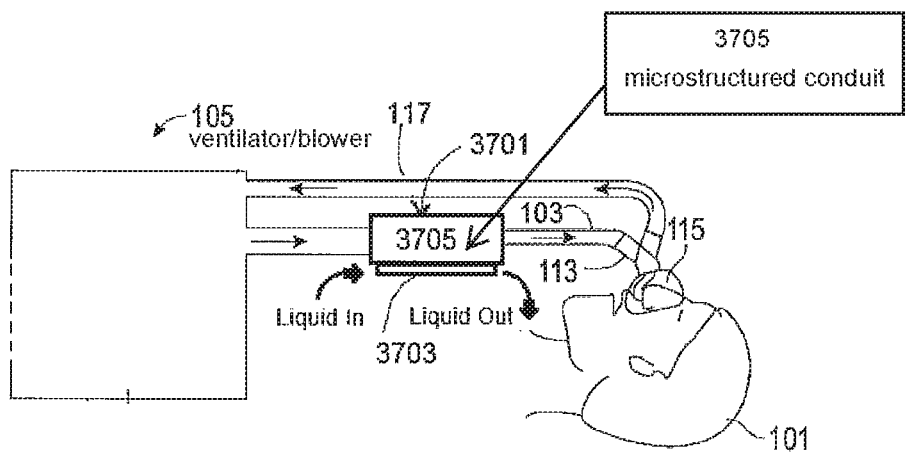
FIG. 37A shows a schematic illustration of a medical circuit incorporating one or more medical tubes, a humidifier tube, and a patient interface.

FIG. 37A illustrates an alternative configuration of the system of FIG. 1 that eliminates the humidifier 107 of FIG. 1. Dry gases pass from a ventilator/blower 105 to a humidifier tube 3701, which humidifies the dry gases. The humidifier tube 3701 connects to an inspiratory tube 103, which delivers the humidified gas to the patient 101 via an outlet 113 (in this example, a Y-piece adapter). An expiratory tube 117 also connects to the outlet 113. Here, the expiratory tube 117 returns exhaled humidified gases from the patient interface 115 to the ventilator/blower 105. The inspiratory tube 103 and/or expiratory tube 117 according to at least one configuration can comprise microstructures, as described in this disclosure. The humidifier tube 3701 comprises a microstructured conduit 3705. The inner wall (adjacent the lumen)

of the microstructured conduit comprises microstructures as described herein. The microstructures can be disposed circumferentially. The microstructures alternatively can be disposed longitudinally. The microstructured conduit 3705 is desirably non-corrugated. Nevertheless, the microstructured conduit 3705 can be corrugated in certain embodiments.

Figure 37B:
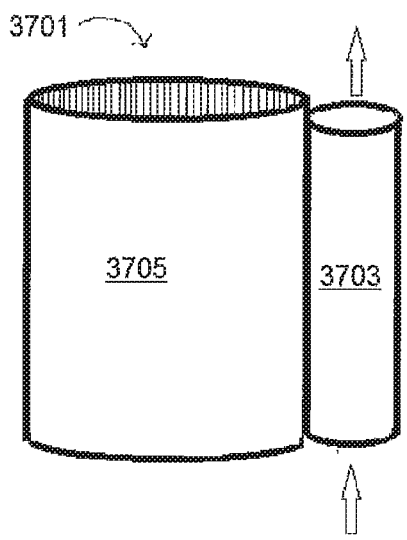
FIGS. 37B and 37C show side and front plan views of an example humidifier tube.
Figure 37C:
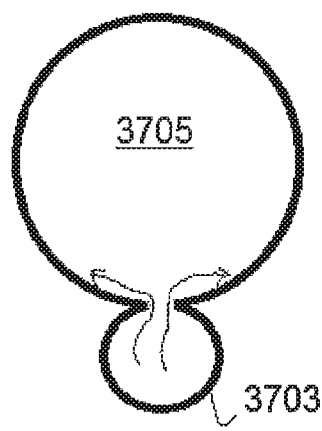

As shown in greater detail in FIG. 37B, a liquid supply conduit 3703 can be disposed adjacent the microstructured conduit 3705. The liquid supply conduit 3703 provides the humidifying liquid to the humidifier tube 3701. The liquid flowing through the liquid supply conduit 3703 can be delivered as a flow-through system. Alternatively, the liquid can be delivered via a recirculator. Desirably, the introduction of liquid is controlled using a suitable rate limiting device, such as a flow restrictor. The lumen of liquid supply conduit 3703 is in fluidic communication with the lumen of microstructured conduit 3705. For example, the lumens can communicate via a plurality of small or capillary-size holes, via a small or capillary-size channel, via a semi-permeable membrane, or via a liquid-permeable material such as nylon. The diameter of liquid conduit 1905, the size of the holes or channel, the permeability of the membrane, and/or the density of the material can be selected to further control the rate of at which liquid is provided onto the inner surface of the tube 1901. As shown in FIG. 37C, a front-plan view of the microstructured conduit 3705 and liquid supply conduit 3703 of FIGS. 37A and 37B, when in use, a liquid in the liquid supply conduit 3703 passes into the microstructured conduit 3705. The liquid is wicked up and spreads over the surface of the microstructured conduit 3705, and the air flowing through the microstructured conduit 3705 takes up the liquid, thereby humidifying the air.

As an alternative to a liquid supply conduit, a collar can be disposed on a forward end of the microstructured conduit 3705 (that is, on the end nearer the ventilator/blower 105). The collar can be essentially similar to the collar 1911 described in the context of FIG. 19B.

Figure 4:
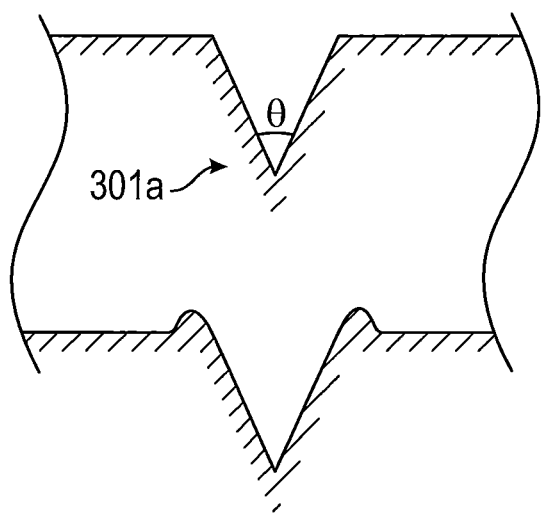
FIG. 4 shows a cross section of an example microstructure.

FIG. 4 illustrates a cross section of an example microstructure 301a. In this example embodiment, the microstructure 301a is a continuous microchannel with a wedge-like structure. A continuous microchannel generally may be defined as a continuous channel having dimensions of 1000 µm (or about 1000 µm) or smaller. In at least one embodiment, the microchannel has a depth d of 20-40 µm (or about 20-40 µm), a maximum width w of 20 µm (or about 20 µm), and an angle θ of 30-60° (or about 30-60°). In certain embodiments, a tube surface has a microchannel-to-solid ratio of 1:1 (or about 1:1). The foregoing dimensions are not limiting, and additional suitable dimensions are discussed in greater detail below. Because of the scale differences between these example embodiments and the example tube dimensions discussed above, microstructured surfaces can reside and operate in an open system, rather than a closed system, such as a lab-on-a-chip.

Figure 16:
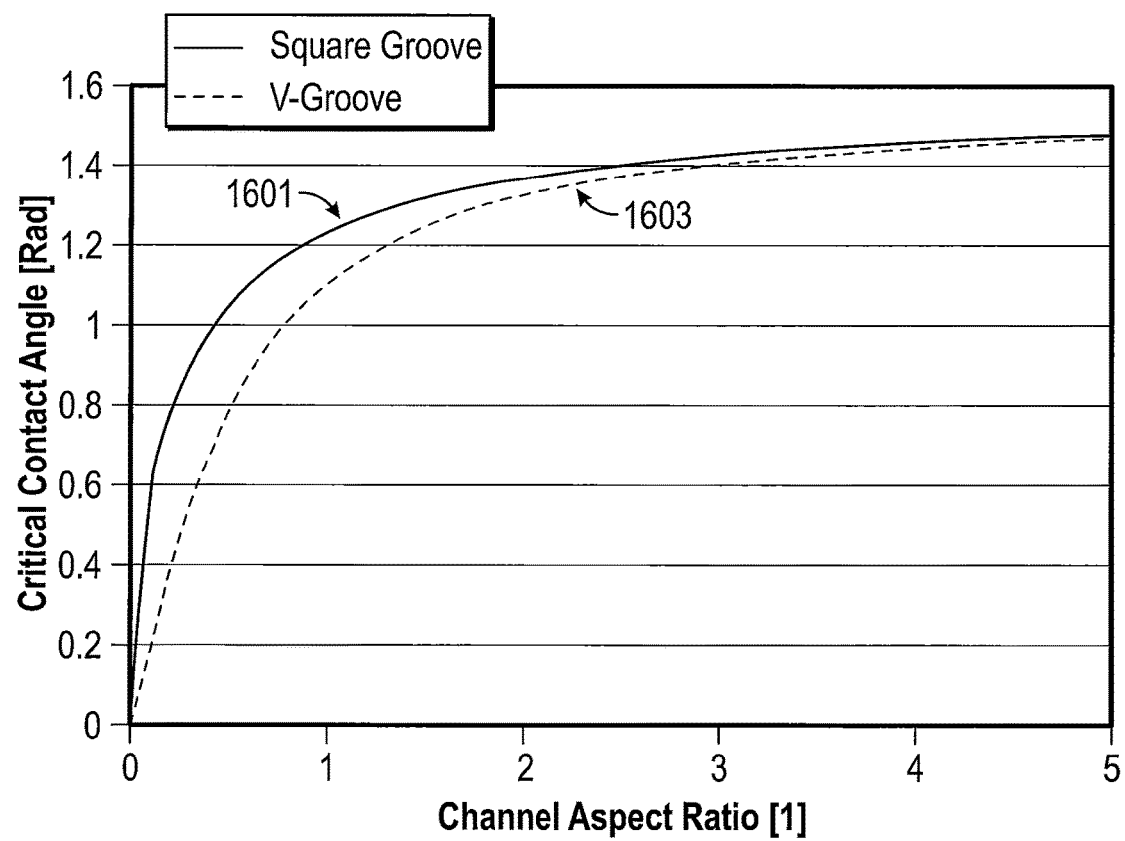
FIG. 16 is a graph of example conditions for wicking in continuous microchannels.

Certain embodiments include the realization that movement of liquid in a microchannel is primarily based on surface forces, rather than inertial forces or gravitational forces. Certain embodiments also include the realization that surface forces generally dominate if the characteristic dimension of the microstructure is smaller than the capillary length ($L_c$), defined as $$L_c = \sqrt{\frac{\sigma}{\rho g}}$$

where σ represents surface tension, ρ represents the fluid density, and g represents the gravitational acceleration constant (9.8 m/s$^2$). For water at room temperature, capillary length is about 2.3 mm. In accordance with the foregoing realizations, microscale dimensions less than about 2.3 mm can result in observable surface phenomena for water at room temperature. It was discovered, however, that the size of microstructures does not always dictate whether there is observable capillary wicking, an increase in surface area, and/or or reduction in film thickness. Accordingly, in certain embodiments, the microstructures includes a base substrate having an equilibrium contact angle less than π/2 (or about π/2). Under isothermal (or nearly isothermal) conditions and on a length scale smaller than capillary length, a criterion for wicking can be defined that depends on the aspect ratio of the microstructure and a critical equilibrium contact angle. For a square trench, the relation can be expressed as $$\theta_{crit} = \arccos\left(\frac{0.5}{0.5 + X}\right)$$

where X is the height to width aspect ratio. For a v-shaped groove, the relation can be expressed as $$\theta_{crit} = \arccos\left(\sin\left(\frac{\beta}{2}\right)\right)$$

where β is the angle of the groove's wedge. FIG. 16 is a graph of example conditions for wicking in continuous microchannels, specifically square (1601) and v-shaped (1603) grooves. In the area below the curves, wicking into the channels tends to occur. In the area slightly above the curves, droplet stretching into a number of meta-stable equilibria is observed, but wicking tends not occur. In the area well above the curves, droplet stretching is not observed and wicking does not occur. Different combinations of surface wettability and channel aspect ratio will result in liquid wicking into the microchannels, provided that the characteristic dimension is smaller than the capillary length for the liquid (so that surface tension forces dominate over viscous forces). In general, however, liquid will wick into the channels if conditions are such that $\theta_{crit}$ is below the curves.

In accordance with the above realizations, it was determined that, to promote wicking, structures with high aspect ratios and/or high surface energy (low contact angles) are desirable. Surfactants, such as those discussed above, can result in contact angles near 0°, so wicking can take place with ease. The equilibrium contact angle over most polymer surfaces is greater than about 0.87 rad (about 50°), so deeper channels can be implemented to facilitate wetting.

Figure 17:
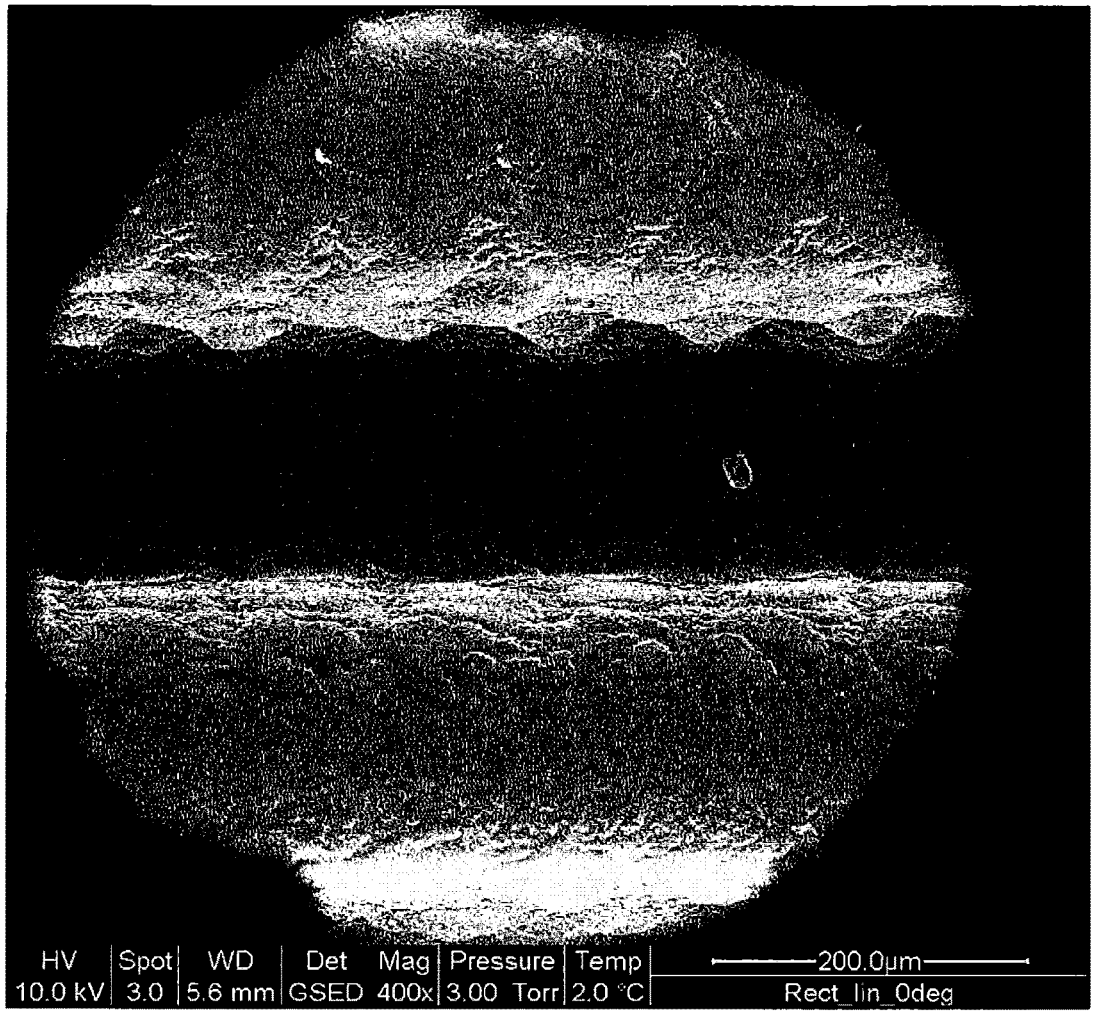
FIG. 17 shows an image of a continuous microstructure.

Surface roughness or microstructures (e.g., regular microstructures) can promote the dispersion of liquid droplets and, therefore, can reduce the thickness/depth of the droplets, which increases the liquid/vapor surface area when the equilibrium contact angle is less than about 90°. The surface roughness of microchannels also can play a role in wicking. It is believed that microstructured or nanostructured bumps within the microchannels could act to pin the solid/liquid/vapor contact line, increase surface area, and/or act as nucleating sites for condensation. FIG. 17 shows microchannels similar to those shown in FIG. 18C, but viewed using an environmental scanning electron microscope. Roughness can clearly be seen on the surface. In some configurations, surface roughness can have a detrimental effect on spreading and evaporation if the contact angle is greater than about 90° because the liquid droplets will spread less, which will reduce the liquid/vapor surface area. For at least this reason, constructions having an equilibrium contact angle of less than about 90° are generally preferred.

Many different shapes of microstructures can achieve desirable results. For example, the continuous microchannel profile can be sinusoidal or a sharp trench. In certain embodiments, the microchannel has an aspect ratio that increases with distance, for example, a chemical or physical gradient. In some embodiments, a channel depth gradient is used to control movement of a liquid in a particular direction. It has been found that liquids tend to move in the direction of the deeper channels. A gradient can be desirable because, provided that hysteresis is slow, the substrate can force a droplet to move toward an area of higher energy in order to lower it. Gradients can also speed up or otherwise improve the wicking of liquid. For example, in some embodiments, a channel depth gradient is used to move liquid toward a region of higher air flow thereby increasing evaporation. In some embodiments, larger channels are used along vertical walls of a structure to direct water from the bottom of the structure to the top of the corrugated structure thereby bringing the water closer to a heating element for evaporation.

Furthermore, the microstructure need not be continuous. Discrete microstructures help liquid to disperse thereby accelerating evaporation. It has been found that on a rough surface, most evaporation happens around the transition of the solid structure and the liquid (i.e., at the edges of the liquid). Accordingly, increasing the roughness of the overall structure increases the transition areas and improves evaporation. For example, a surface can comprise discrete features such as cylindrical, pyramidal, or cube-shaped posts or pillars. Microstructures can also comprise a hierarchy of the foregoing features. In some embodiments, discrete features are uniform or partially uniform. In some embodiments, the discrete features are randomly distributed on a surface. For example, some embodiments utilize crystals having irregular shapes spread across or adhered to a surface. In some embodiments, an irregular surface (i.e., not smooth) can advantageously improve evaporation.

Figure 20:
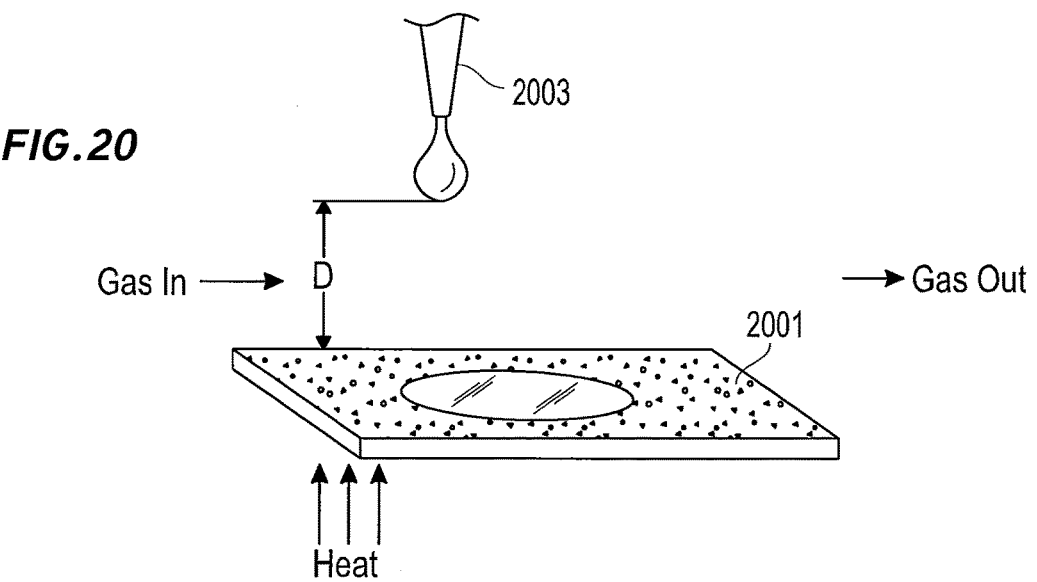
FIG. 20 illustrates an embodiment in which a rough surface can be used to enhance evaporation.
Figure 21:
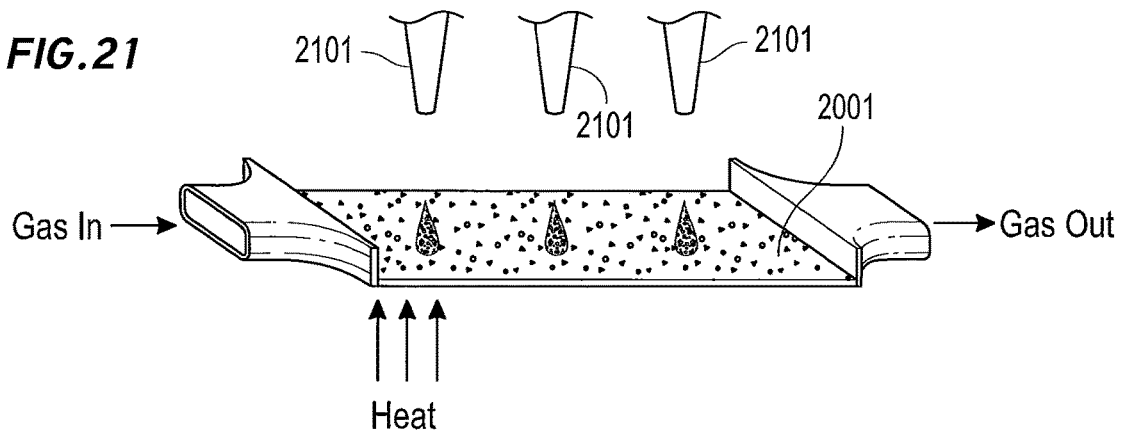
FIG. 21 illustrates another embodiment in which a rough surface can be used to enhance evaporation.

FIGS. 20 and 21 illustrate embodiments that utilize irregular or rough surfaces to enhance evaporation of a liquid. FIG. 20 illustrates that a liquid may be applied to a rough surface 2001 using a liquid dispenser 2003 located some distance D from the rough surface 2001 that outputs small amounts of the liquid. In some configurations, the drops are emitted as one drop at a time. In some configurations, the drops can splash upon contact, which results in smaller droplets.

Each drop may contact the rough surface 2001 and quickly spread across the rough surface 2001 thereby enhancing the evaporation of the liquid into a gas that flows over the rough surface 2001. In some embodiments, the rough surface 2001 is heated to further enhance the evaporation of the liquid into the passing gas. While the embodiment in FIG. 20 has been shown with only a single liquid dispenser 2003, or dropper, some embodiments may comprise more than one liquid dispenser 2003. As shown in FIG. 21, multiple liquid dispensers 2101 can be located at various locations over the rough surface 2001 to increase the coverage of the liquid on the rough surface 2001. In some embodiments (not shown), a surface comprising a plurality of holes serves as the liquid dispenser 2101. A liquid, such as water, is allowed to flow over the surface. The liquid then drips or falls through the plurality of holes in the surface down to the rough surface 2001 below. A gas may flow between the two surfaces (i.e., the first surface and the rough surface 2001) and evaporates the liquid as it falls and after is disperses among the microstructures of the rough or irregular surface 2101. FIG. 21 further illustrates that in some embodiments, the flow of a gas, such as air that is to be humidified, can be channeled or shaped to form a relatively flat stream over the rough surface 2001. Such a configuration may force more of the gas to interact with the rough surface 2001.

Figure 22:
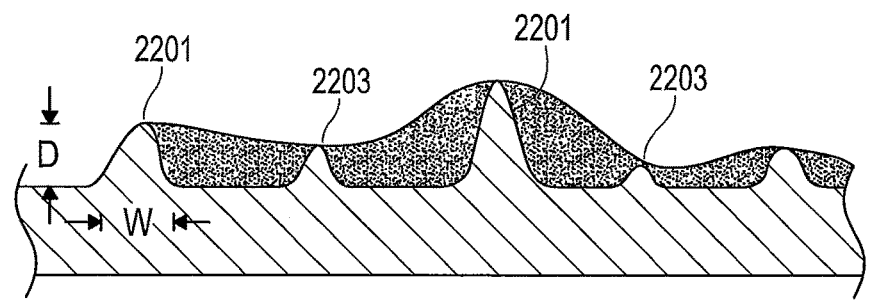
FIG. 22 illustrates the irregularity of the some microstructures on a surface.

FIG. 22 illustrates one type of rough surface that includes a plurality of ridges 2201 having varying heights and widths. It is believed that rough surfaces having higher height to width ratios (e.g., steeper slopes) spread liquids and increase evaporation. In some configurations, having steeper slopes is believed to increase the number of contact lines. In some embodiments, increasing the number of contact lines between the liquid and the rough surface is believed to increase evaporation. In some embodiments, the presence of taller ridges 2201 may increase the number of contact lines between the liquid and the rough surface thereby increasing evaporation relative to a surface having shorter ridges 2203. In some embodiments, the use of heat applied to rough surface may increase the rate of evaporation particularly at the contact lines. In some embodiments, the use of a surface having integral microstructures, namely microstructures integrally connected to the underlying surface, may allow for better heat transfer if the underlying surface is heated. Such a configuration may improve the ability of heat to assist in the evaporation of the liquid.

Although the discussion above regarding FIGS. 20-22 refers to rough or irregular surfaces, a microstructured surface having a regular pattern may achieve similar results. Similar to droplets on a rough surface, droplets on a surface with microstructures will disperse and evaporate into a passing gas more quickly than a smooth surface having no microstructures or surface irregularities. In some embodiments, the microstructures are uniform. In some embodiments, the microstructures are sized and arranged according to a pattern if not every microstructure is the same.

If the wicking criteria discussed above are satisfied, then water will wick into the microchannels and/or micropillars with certain dynamics, termed Lucas-Washburn dynamics. The wicking length (L) increases proportional to the square root of time (t) ($L=A\sqrt{t}$), regardless of the shape of the channel or the aspect ratio, so long as it is of a uniform cross section. A is a function of surface tension, viscosity, the cross sectional area of the channel, and the contact angle. Thus, what determines the strength of this relationship (i.e., the value of A) depends on some or all of these parameters.

Certain embodiments include the realization that low contact angles, high aspect ratios, high surface tension, and low viscosity can lead to improved wicking. Because wicking length is proportional to the square root of time, the velocity of wicking is inversely proportional to length and inversely proportional to the square root of time. Stated another way, wicking slows down with distance and with the passage of time.

Figure 18D:
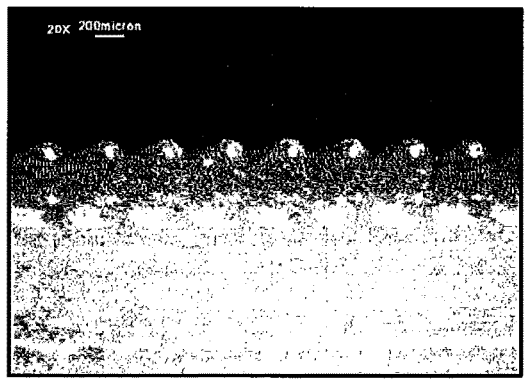

FIGS. 18A through 18L show images of continuous and discrete microstructures. The substrate material in FIG. 18A is polyethylene terephthalate (PET). The substrate material in the other figures is an acrylic.

Figure 18E:
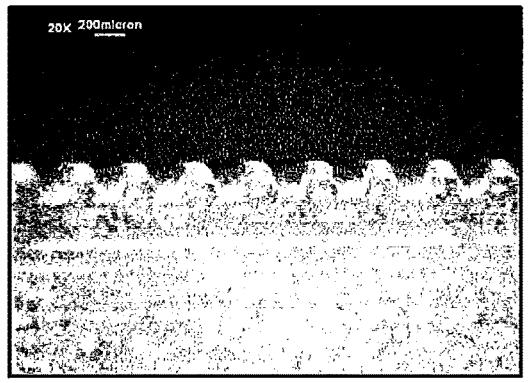
Figure 18F:
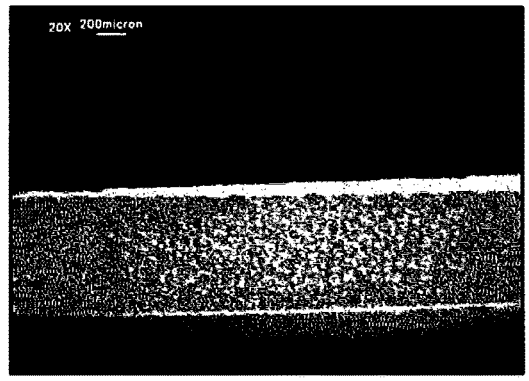
Figure 18G:
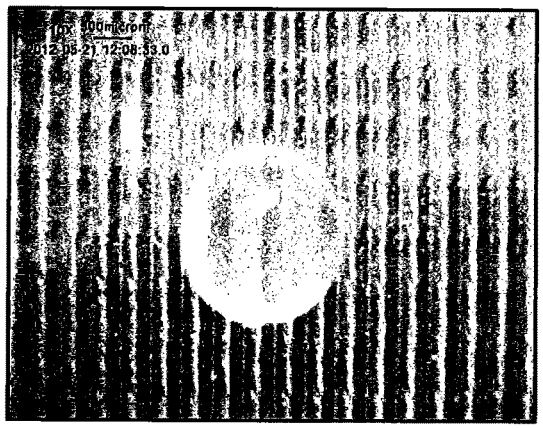
Figure 18H:
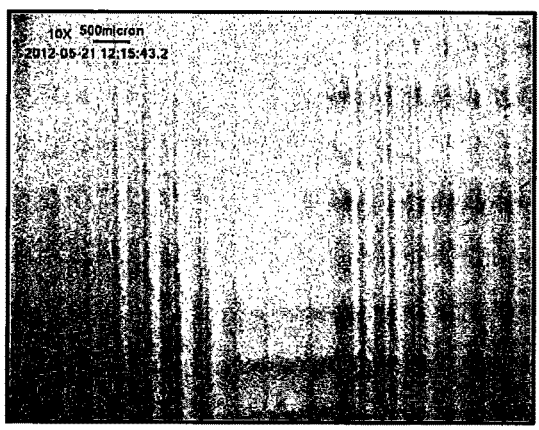
Figure 18I:
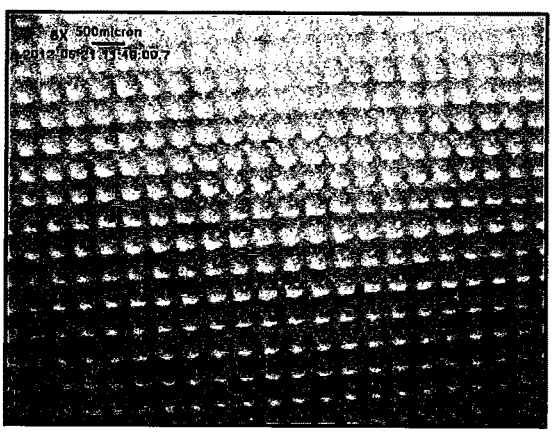
Figure 18J:
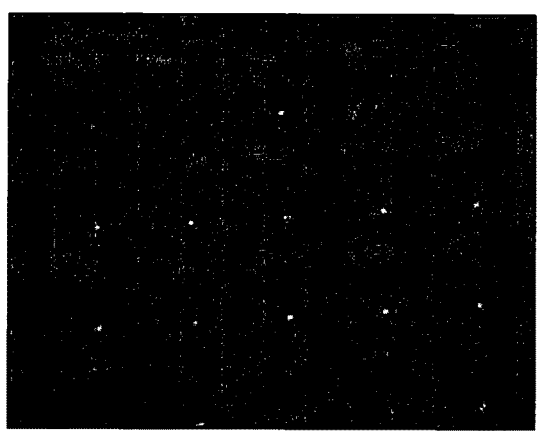
Figure 18K:

The v-shaped grooves in FIG. 18A were cut using a double-edge razor blade. The other microstructures were fabricated using a 3D printer (ProJet HD 3000). In some embodiments, microstructures or surfaces incorporating microstructures can be manufactured by direct injection molding or hot embossing. Although not shown in these figures, it is also possible to machine microstructures using a CNC (computer numerical control) machine equipped with micro-end mills, such as those sold by Performance Micro Tool (Janesville, Wis.). FIGS. 18B and 18C show square-shaped grooves. FIG. 18D shows a front view of a square microchannel array having a gradient in topography, and specifically shows the front view of the long end of the microchannels. FIG. 18E shows a front view of the short end of the microchannels of FIG. 18D. FIG. 18F shows a side view of a square microchannel array of FIG. 18D. As discussed herein, with a gradient in the topography, the dynamics of wicking (specifically, the speed-time relation) can potentially be modified by having microstructures that change in depth with distance. This topography can desirably influence the way that liquid evaporates and condenses on the surface. Such variable depth configurations can be achieved by embossing, machining, or casting. FIG. 18G shows a droplet on square grooves that have not been treated with a surfactant. FIG. 18H shows spreading of a droplet on square grooves that have been treated with a surfactant. FIGS. 18I and 18J show top-down views of a pillared surface at different magnifications. FIG. 18K shows a side view of the pillared surface.

Figure 18L:
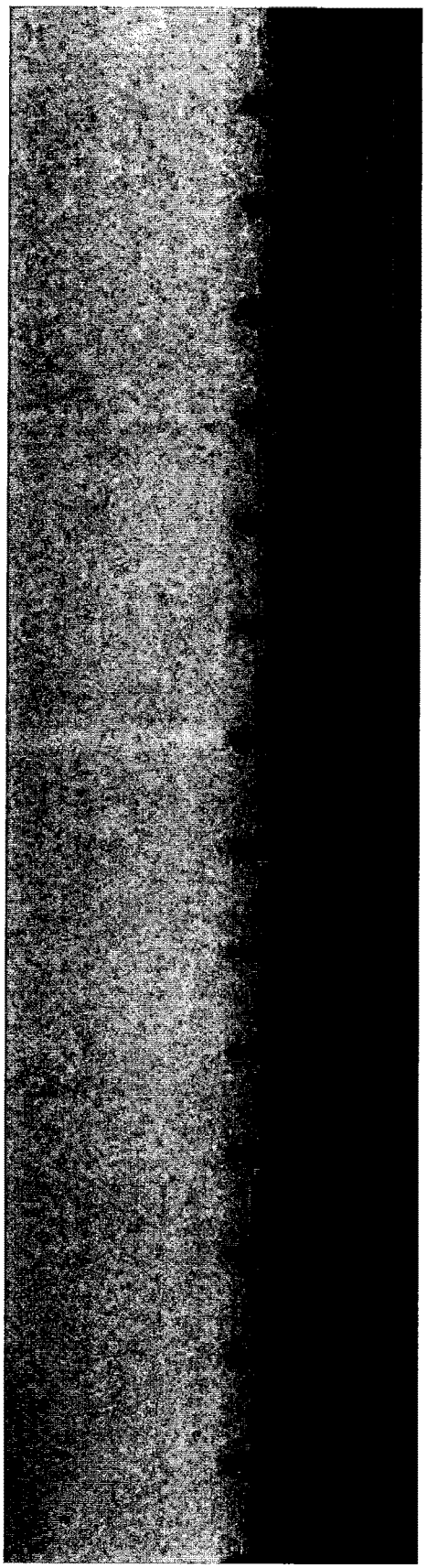

FIG. 18L shows another embodiment of a microstructure defining a surface shape that is an inverse of the shape of the microstructure of FIG. 18A. The microstructure of FIG. 18L comprises alternating taller ridges and shorter ridges, each of which are separated from one another by a small channel or first microchannel. Preferably, the taller ridges are substantially taller than the shorter ridges and may be 2-3 times as tall, or taller, than the shorter ridges. In the illustrated arrangement, the shorter ridges are substantially wider than the taller ridges, such as about 3-5 times wider, for example. In certain embodiments, the cross-sectional height of a small channel is in the range of 5 and 10 µm (or in the range of about 5 and about 10 µm), and the cross-sectional height of a ridge is in the range of 30 and 200 µm (or in the range of about 30 and 200 µm), such as 40 µm (or thereabout).

The small channels can be any suitable size, such as about the width of the taller ridges, for example. The cross sectional area of a small channel is approximately equal to one-half the cross sectional area of the adjacent taller ridge. In addition, the taller ridges define large channels (also referred to as second microchannels or main channels) therebetween, which can communicate with or be contiguous with the small channels. A depth of the large channels can be larger than a depth of the small channels, such as up to 2-3 times as large, or larger. The small channels can be generally triangular, square, or trapezoidal in cross-sectional shape, while the large channels can have a cross-sectional shape generally similar to an inverted trapezoid. Because the shorter ridges preferably define a significantly larger area than the taller ridges, the upper surfaces of the shorter ridges can be viewed as the outer surface of the material or substrate, with the small channels being recessed from the outer surface and the taller ridges projecting from the outer surface.

Figure 24A:
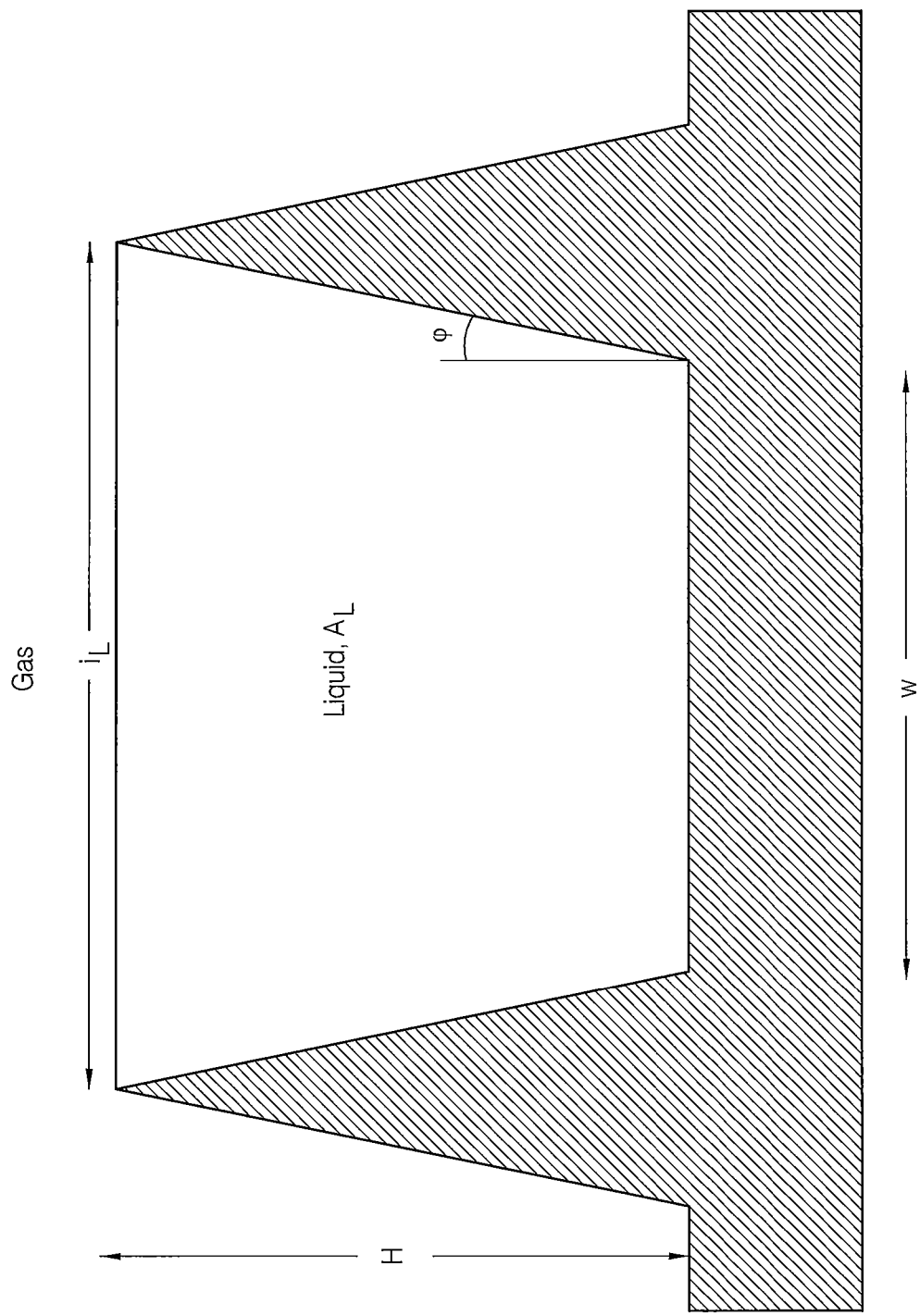
FIG. 24A illustrates a surface comprising inverse-trapezoidal microstructures.

The embodiment of FIG. 18L can be modeled as shown in FIG. 24A. Under isothermal (or nearly isothermal) conditions and on a length scale smaller than capillary length, a criterion for wicking can be defined that depends on the aspect ratio, channel geometry, and a critical contact angle. For the inverse trapezoidal shape of FIG. 18L and FIG. 24A, the relation can be approximated as $$\theta_{crit} = \arccos\left(\frac{\lambda\cos\phi + 2\sin\phi}{\lambda\cos\phi + 2}\right)$$

where $\lambda$ is the inverse of the height to width aspect ratio, that is, such that $\lambda = W/H$, and $\phi$ is the angle shown in FIG. 24A. Wetting will occur when the material's equilibrium contact angle is below the critical angle $\theta_{crit}$, and no wetting will occur when the material's equilibrium contact angle is above the critical angle $\theta_{crit}$.

In addition, in the embodiment of FIG. 24A, the relation between the capillary filling length (L) and capillary filling time (t) can be expressed as follows:

$$\frac{t\sigma}{\mu L_f} = -\tilde{M}\left(\frac{L}{L_f} + \ln\left[1 - \frac{L}{L_f}\right]\right)$$

where $$\tilde{M} = 24\left(\frac{l_c}{H}\right)^2 \frac{1 + (\lambda + \tan\phi)^2}{(2\lambda + \tan\phi)(\lambda + \tan\phi)}, \text{ and}$$

$$L_f = \frac{(\cos\theta_e - \cos\theta_{crit})c_L\sigma}{A_L\rho g} \text{ (that is, the final capillary height)}$$

$$l_c = \sqrt{\frac{\sigma}{\rho g}} \text{ (that is, the capillary length for the fluid)}$$

$$c_L = \frac{H}{\cos\phi}(2 + \lambda\cos\phi) \text{ (that is, the liquid-solid contact length)}$$

$$A_L = H^2(\lambda + \tan\phi) \text{ (that is, the cross-sectional area)}$$

and $\sigma$ represents the surface tension of the fluid, $\mu$ represents viscosity of the fluid, $\rho$ represents density of the fluid, $\theta_e$ represents the contact angle of the fluid, g is the gravitational constant, and the remaining variables (H and $\phi$), represent the channel geometry shown in FIG. 24A. The approximate time to reach the equilibrium height can be expressed as follows:

$$t_f = \frac{\tilde{M}\mu L_f}{2\sigma}$$

If the capillary is not vertical, then the foregoing model is modified by multiplying $L_f$ by sin $\alpha$, where $\alpha$ is the inclination angle from the horizontal axis with respect to the flow direction.

Figure 24B:
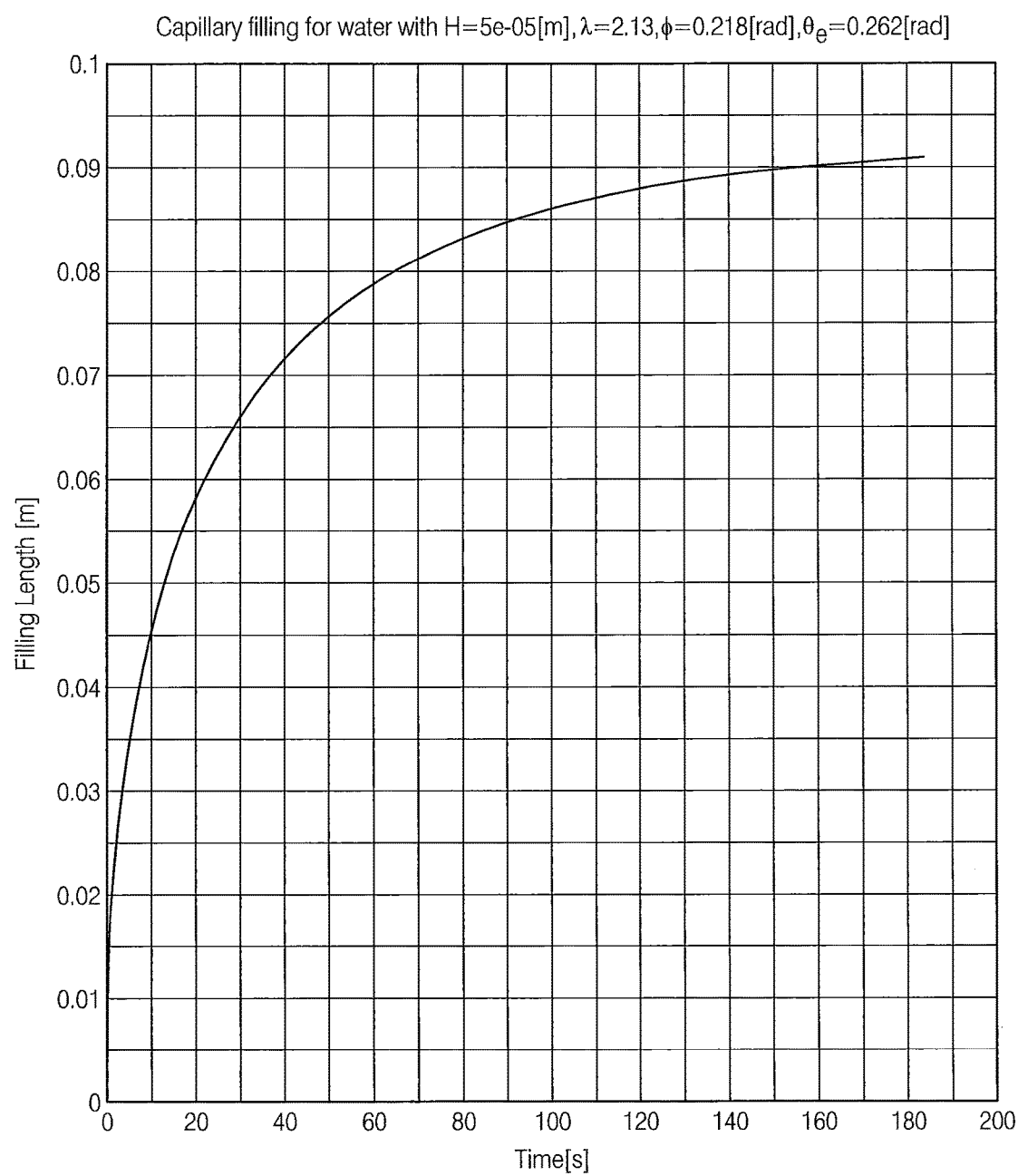
FIG. 24B is a graphical representation of the relationship between capillary filling length and capillary filling time in an inverse-trapezoidal microstructure.

FIG. 24B is a graphical representation of the foregoing relationship between capillary filling length (L) and capillary filling time (t) in an inverse trapezoidal microstructure for water, where $H=5\times10^{-5}$ m, $\lambda=2.13$, $\phi=0.218$ rad, and $\theta_e=0.262$ rad. It should be noted that the small channels shown in FIG. 18L can modify the critical angle for wetting, $\theta_{crit}$, below which wetting can occur).

It was observed that, when the small channels have an aspect ratio that is smaller than that needed to satisfy the critical contact angle formula for the respective geometry of the small channel (viz., triangular, square, or trapezoidal) and the wetting criteria for the main channel is met, the small channels promote wetting in the composite channel (which includes the space between the microridges and encompasses both the small channels and the main channel) by increasing the surface area of the structure. It was further observed that liquid will flow in the small channels and the main channel at the same rate.

It was also observed that, when the small channels have an aspect ratio that is larger than that needed to satisfy the critical contact angle formula for the respective geometry of the small channel and the wetting criteria for the main channel is met, liquid will flow in the small channels and main channel independently. This effect reduces the surface area available for the flow in the main channels, which can slow the flow in the main channel while liquid can flow more quickly in the small channels. The liquid in the small channels is typically a very thin film (in the range of 6 and 10 μm or in the range of about 6 and about 10 μm), which evaporates faster than the liquid in the main channel. Thus, small channels having a large aspect ratio can improve evaporation.

It was further observed that, when the small channels have an aspect ratio that is larger than that needed to satisfy the critical contact angle formula for the respective geometry of the small channel and the wetting criteria for the main channel is not met, liquid will flow in the small channels and will not flow in the main channel.

Returning again to FIG. 3A, the microstructures 301 can extend along the entire length of the tube 201 or along a portion of the length of the tube 201, such as a central portion that is likely to collect condensate. Alternatively, the microstructures 301 can extend along the tube 201 at regular or irregular intervals, separated by portions with no microstructures. The foregoing figures show the microstructures 301 encircling the inner circumference of the tube 201. The microstructures 301 need not encircle the entire inner circumference in all embodiments, however. For example, the microstructures 301 can be disposed around half or quarter of the circumference.

It was discovered that a single drop of liquid can spread many times its diameter and a very efficient evaporation of liquid can be achieved if heat is supplied to the substrate beneath the liquid. Accordingly, in certain embodiments, the one or more filaments discussed above comprise heating filaments. Heating filaments can be embedded or encapsulated in the wall of the tube 201. For example, the one or more filaments can be spirally wound in the wall of the tube 201 around the tube lumen. The one or more filaments can be disposed within the tube 201, for example, in a spirally-wound configuration as described in U.S. Pat. No. 6,078,730 to Huddard et al., which is incorporated in its entirety by this reference. The arrangement of heating filaments is not limited to one of the foregoing configurations. Furthermore, heating filaments can be arranged in a combination of the foregoing configurations.

Figure 5A:
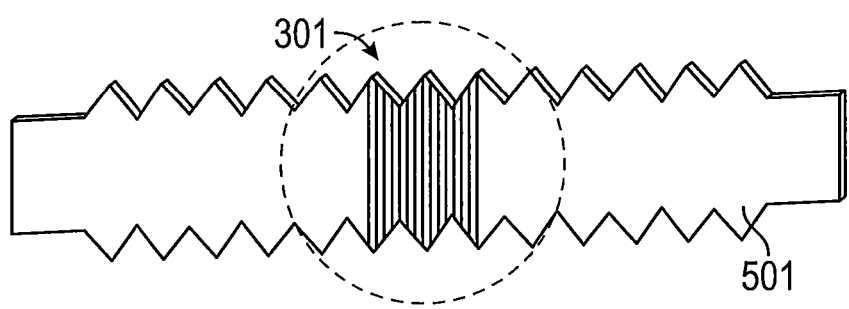
FIG. 5A shows a front perspective view of an inner component for a tube.
Figure 5B:
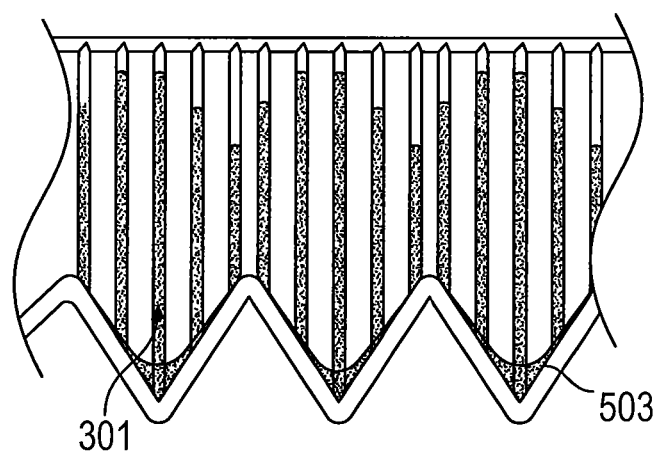
FIG. 5B shows a first magnified portion of the inner component of FIG. 5A shown in front perspective.

In certain embodiments, the tube 201 comprises an inner component comprising microstructures. An example inner component 501 is shown in FIG. 5A. The inner component 501 includes microstructures 301, as described above. A magnified view of the inner component 501 is shown in FIG. 5B. The example inner component 501 is a serrated strip. The inner component 501 is placed and configured within the tube (not shown) such that the bottom portion of the inner component 501 is exposed to liquid condensate 503 within the tube. The serrations in the inner component 501 can be sized and configured to complement the corrugations of the tube, such that the tube generally holds the inner component 501 in place. In FIG. 5B, the microstructures 301 extend vertically to cover both axial surfaces of the inner component 501 along the longitudinal length of the inner component 501. Alternatively, the microstructures 301 can cover one axial surface. In certain configurations, the microstructures 301 can extend along a portion of the longitudinal length or along regular or irregular intervals of the longitudinal length. The inner component 501 can comprise more than one serrated strips. For example, an inner component can comprise two serrated strips and resembles a plus-sign having serrations along the longitudinal length. These embodiments are not limiting. A larger number of strips can be incorporated. However, it can be advantageous to have a lower number of strips to improve the airflow through the tube lumen and/or improve tube flexibility.

Figure 6:
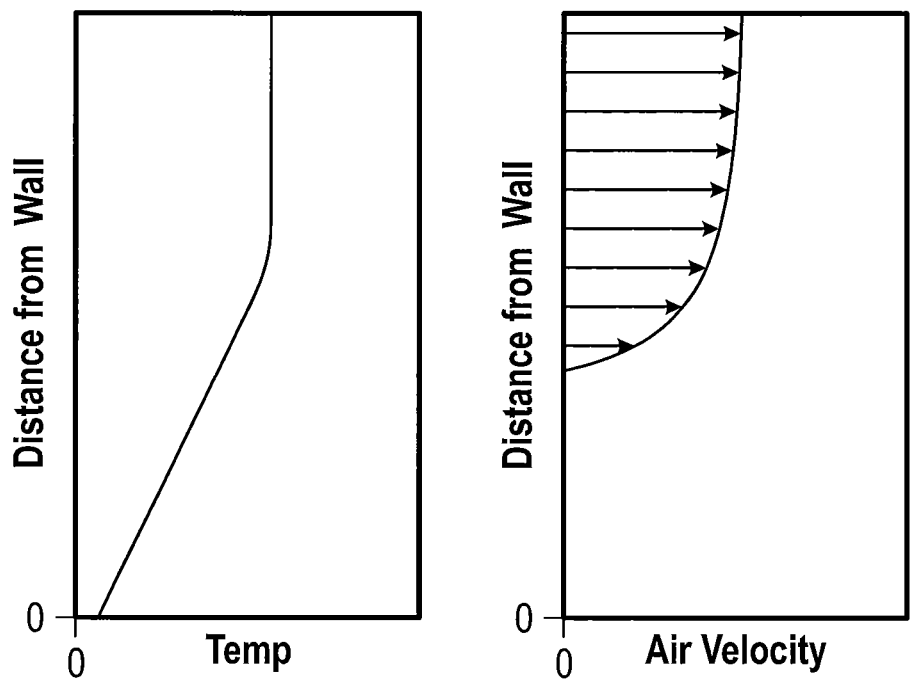
FIG. 6 shows a schematic illustration of airflow velocity and temperature profiles within a tube.

Inclusion of the inner component 501 can be advantageous because the inner component 501 can allow the microstructures 301 to extend into the tube lumen and reach the center of the tube 201 lumen. As shown in FIG. 6, airflow velocity increases from the tube wall to the center of the tube lumen (centerline) and reaches a maximum at the centerline. Thus, water rising up the microstructures 301 in FIGS. 5A and 5B is exposed to the warm, higher velocity air flow. Exposing the condensate to the higher air velocity near the center of the tube increases the likelihood that the condensate will evaporate into the air stream.

Alternative configurations are possible for the inner component 501. For example, the inner component 501 can be wound inside the tube 201. This configuration can be desirable because it allows the microstructures to extend a distance into the tube 201 lumen, which is exposed to higher airflow velocity than the tube 201 walls. In at least one embodiment, the inner component 501 is wound so that at least a portion of the inner component 501 crosses the center of the tube lumen.

As noted above, it was discovered that the addition of heat to a microstructured surface can dramatically improve evaporation rates. Accordingly, the inner components 501 of any of the foregoing embodiments can incorporate a heating filament, which can improve heating of the airflow along the tube and, thus, the likelihood that condensate in the microchannels will evaporate into the airflow. Incorporating one or more heating filaments into the inner component 501 also decreases the likelihood that condensation will occur on the warm inner component. It was discovered that evaporation is highest at the contact region, where the solid surface, liquid droplet, and evaporated vapor meet. This is due to the proximity to the heated surface. The closer to the solid, the higher the mass transfer. Accordingly, certain embodiments include the realization that it can be desirable to have a larger number of narrower channels. For example, higher evaporation rates can be achieved on a surface having ten 100 μm channels than on a surface having five 200 μm channels.

In should be noted that the above-described configuration of microstructures can be advantageous because it may be used to convey liquids without the use of a pump or pumps. Furthermore, certain embodiments include the realization that microstructured surfaces would not require pumps to direct liquids, as the liquid movement is driven by capillary action.

Additional Methods of Manufacturing Tubes

As noted above, a tube may be made from one or more extruded polymer components. The properties of the extrudate (including composition, surface-modifying agents, methods for increasing surface energy) are described above.

A first manufacturing method is described with reference to FIG. 14. The method comprises extruding an elongate conduit having a longitudinal axis, a lumen extending along the longitudinal axis, and a wall surrounding the lumen. Microstructures can be pressed or otherwise formed on the conduit during extrusion. Microstructures can also be molded, printed, cut, thermoformed, or otherwise formed on the conduit after extrusion. As shown in FIGS. 4, 8D, and 9D, it was observed that cutting microchannels into a surface using a sharp object could result in raised edges around the top portion of the microchannel. Accordingly, in some methods, it can be desirable to grind or polish the surface after microchannel formation to improve surface uniformity. The method can also involve corrugating the elongate conduit, such as with a corrugating die. More specifically, the process involves mixing or providing of a master batch of extrudate material (i.e., material for extrusion), feeding the master batch to an extrusion die head, extruding the extrudate as described above, and (optionally) feeding the elongate conduit into a corrugator using an endless chain of mold blocks to form a corrugated tube.

Figure 14:
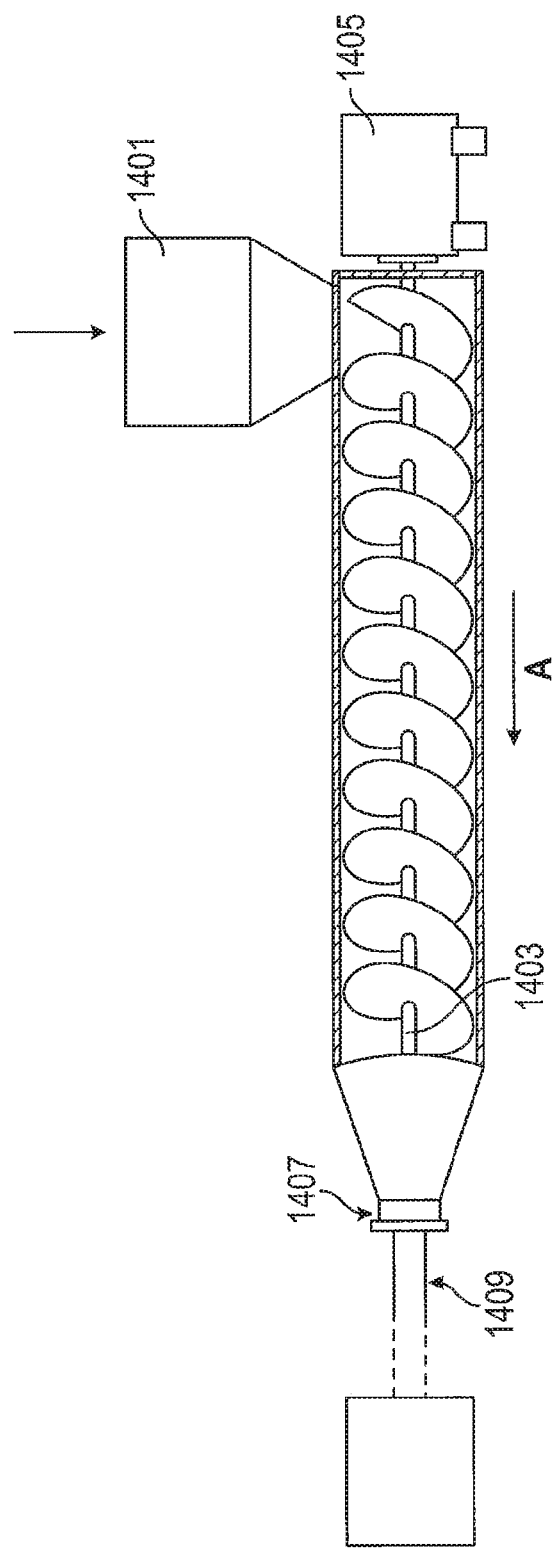
FIG. 14 is a schematic illustration of a manufacturing method of medical tube, including a hopper feed, screw feeder to a die head, and terminating with a corrugator.

FIG. 14 generally illustrates a setup where there is provided a feed hopper 1401 for receiving raw ingredients or material (e.g., master batch and other materials) to be passed through a screw feeder 1403 driven by a motor 1405 in direction A toward a die head 1407. A molten tube 1409 is extruded out of the die head 1407. Conductive filaments can optionally be co-extruded on or in the molten tube 1409.

An extruder such as a Welex extruder equipped with a 30-40 mm diameter screw and, typically, a 12-16 mm annular die head with gap of 0.5-1.0 mm has been found to be suitable for producing low cost tubes quickly. Similar extrusion machines are provided by American Kuhne (Germany), AXON AB Plastics Machinery (Sweden), AMUT (Italy), and Battenfeld (Germany and China). A corrugator such as those manufactured and supplied by Unicor® (Hassfurt, Germany) has been found to be suitable for the corrugation step. Similar machines are provided by OLMAS (Carate Brianza, Italy), Qingdao HUASU Machinery Fabricate Co., Ltd (Qingdao Jiaozhou City, P.R. China), or Top Industry (Chengdu) Co., Ltd. (Chengdu, P.R. of China).

During manufacture, the molten tube 1409 is passed between a series of rotating molds/blocks on the corrugator after exiting the die head 1407 and is formed into a corrugated tube. The molten tube is formed by vacuum applied to the outside of the tube via slots and channels through the blocks and/or pressure applied internally to the tube via an air channel through the center of the extruder die core pin. If internal pressure is applied, a specially shaped long internal rod extending from the die core pin and fitting closely with the inside of the corrugations may be required to prevent air pressure escaping endways along the tube.

The tube may also include a plain cuff region for connection to an end connector fitting. Thus, during manufacture, a molded-plastic end connector fitting can be permanently fixed and/or air tight by friction fit, adhesive bonding, over molding, or by thermal or ultrasonic welding.

Figure 15:
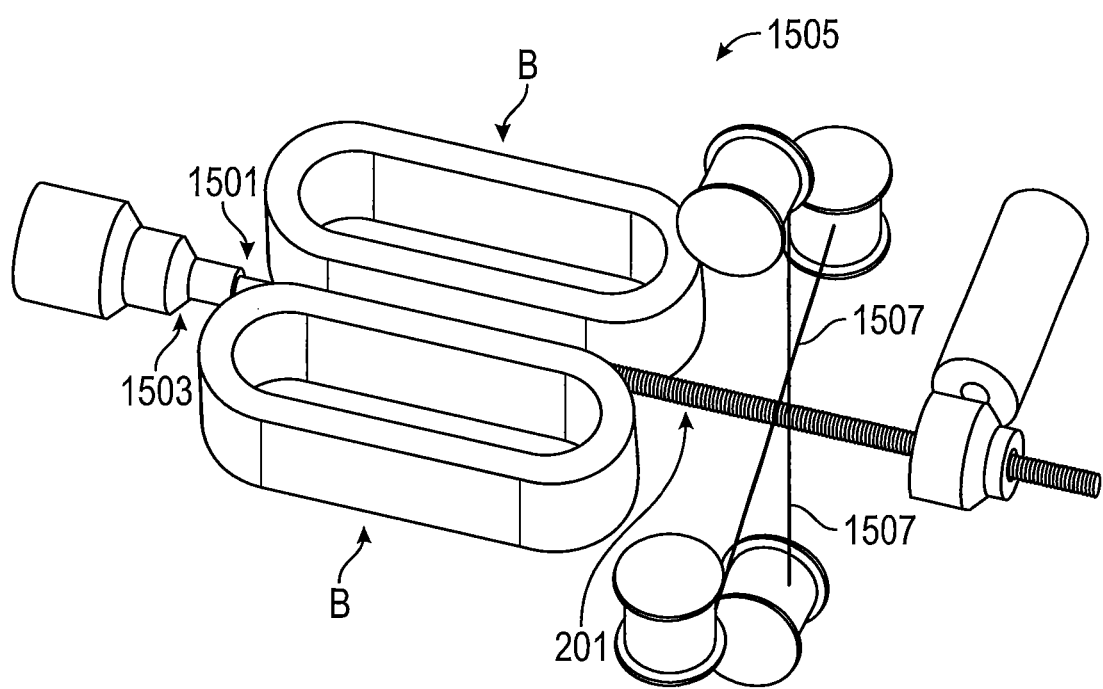
FIG. 15 is a schematic illustration of a spiral-forming manufacturing method for medical tubing.

Another suitable method for manufacturing a tube according to the embodiments described here involves spiral forming, as shown in FIG. 15. In general, the method comprises extruding a tape and spirally winding the extruded tape around a mandrel, thereby forming an elongate conduit having a longitudinal axis, a lumen extending along the longitudinal axis, and a wall surrounding the lumen. The method can also include optionally corrugating the elongate conduit. Microstructures can be pressed or otherwise formed on the tape during extrusion. Microstructures can also be molded, printed, cut, thermoformed or otherwise formed on the tape after extrusion. In addition, microstructures can also be molded, printed, cut, thermoformed or otherwise formed on the assembled conduit. In some methods, it can be desirable to grind or polish a surface after microchannel formation to improve surface uniformity.

The extrusion process involves mixing or providing of a master batch of extrudate material (i.e. material for extrusion), feeding the master batch to an extrusion die head, extruding the extrudate into a tape.

Then, the extruded or pre-formed tape is wound helically. In some embodiments, a reinforcing bead overlays turns of tape. The bead may provide a helical reinforcement against crushing for the tube and may also provide a source of heat, chemical or mechanical adhesive for fusing or joining the lapped portions of tape.

Shown in FIG. 15 is a molten extruded tube 1501 exiting the die 1503 of an extruder before passing into a corrugator 1505. On exiting the corrugator 1505, a heater wire 1507 is wound about the exterior of the formed tubular component.

One advantage of the preferred type of the tube manufacture described above with reference to FIG. 15 is that some of the mold blocks B can include end cuff features that are formed at the same time as the tubular component. Manufacture speeds can be significantly increased by the reduction in complexity and elimination of secondary manufacturing processes. While this method is an improvement over separate cuff forming processes, a disadvantage of the prior art plain cuff is that the corrugator must slow down to allow the wall thickness of the tube in this area to increase (the extruder continues at the same speed). The cuff thickness is increased to achieve added hoop strength and sealing properties with the cuff adaptor fitting. Further, the heat of the molten polymer in this thicker region is difficult to remove during the limited contact time with the corrugator blocks and this can become an important limiting factor on the maximum running speed of the tube production line.

Additional Methods of Manufacturing Planar Micro Structured Surfaces

Microstructures having a size in the range of 5 µm and 30 µm (or in the range of about 5 µm and about 30 µm) can be formed on planar surfaces, including humidification chamber walls and the like. As used herein, a planar surface broadly refers to a non-tubular surface. The term "planar surfaces" encompasses curved surfaces, such as the walls of a humidification chamber and turbine-type impeller blades. The term "planar surfaces" also encompasses substantially flat surfaces such as paddle-type impeller blades.

Figure 25A:
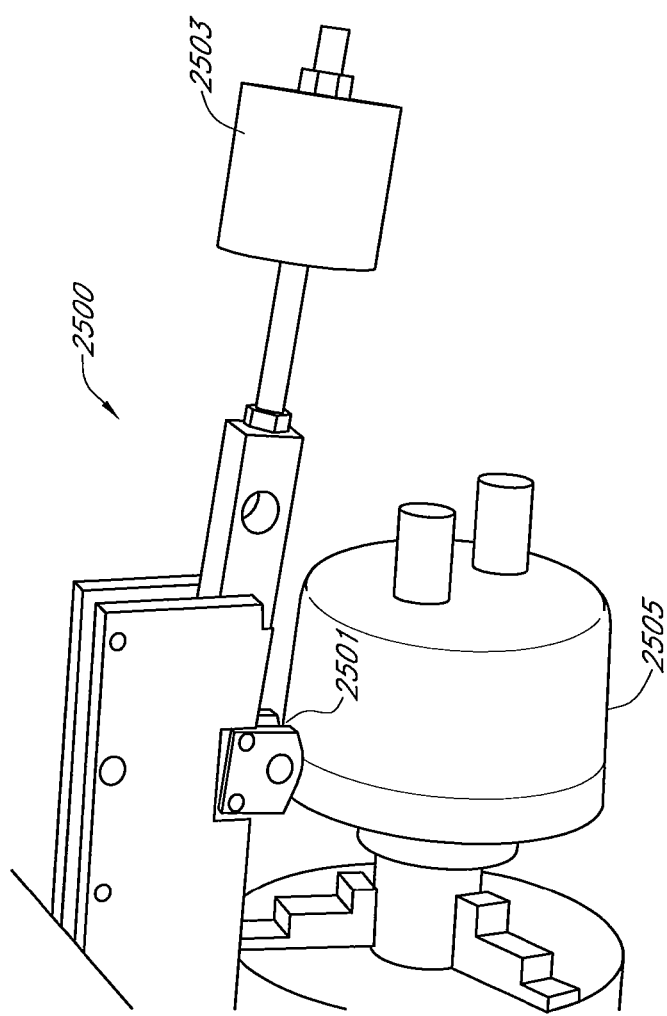
FIG. 25A illustrates a device suitable for use in a method for forming microstructures on a planar surface.
Figure 25B:
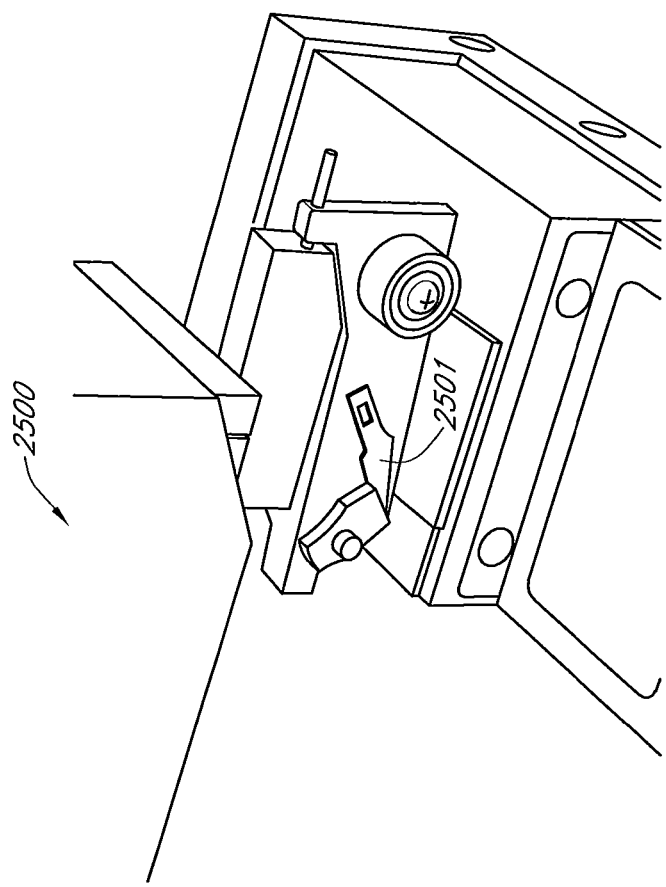

At least one method for forming microstructures comprises providing a device comprising a fine cutting blade. FIG. 25A shows a suitable device 2500. The device 2500 of FIG. 25A comprises a fine cutting blade 2501, such as a razor blade, and an adjustable weight 2503 at one end. The device 2500 is shown cutting a template for a humidification chamber 2505. FIG. 25B shows a detail of an example of the cutting blade 2501 suitable for use in the device 2500 of FIG. 25A. FIG. 25C shows a cross section of another example of the cutting blade 2501 suitable for use in the device 2500 of FIG. 25A. The cutting blade 2501 of FIG. 25C is discussed in greater detail below. The device can be attached to a CNC machine capable of drawing the device over a planar surface. The force applied by the cutting blade can be in the range of 1 N and 2 N (or in the range of about 1 N and about 2 N). Suitable materials for the planar surface include plastics such as acrylic and polypropylene and metals such as aluminum. The device cuts the surface at a selected spacing and produces V-shaped grooves, channels, or trenches. The weight can be adjusted to alter the depth of the grooves or trenches. A hierarchy of grooves, channels, or trenches (e.g., groove-in-groove, channel-in-channel, or trench-in-trench) can be formed with this method, particularly when a hard surface material, such as acrylic, is used.

It was discovered that, when a hard surface material such as acrylic is cut, the resulting grooves, channels, and/or trenches have rough sidewalls. Accordingly, it can be desirable to provide a means for smoothing the sidewalls of a microstructured groove, channel, or trench. A smoothing means includes heating the cutting blade 2501 during cutting. A smoothing means can also include heating the surface material after cutting. Yet another smoothing means includes exposing the surface material to a solvent suitable for dissolving imperfections in the sidewall, such as a chlorinated solvent.

Figure 26A:
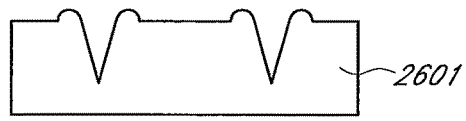
FIGS. 26A-26H illustrate a method for forming microstructures on a planar surface.
Figure 26B:
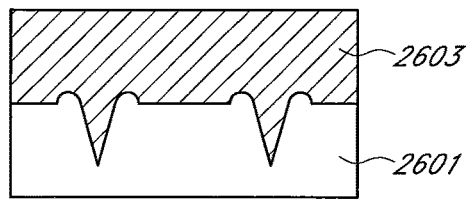
Figure 26C:
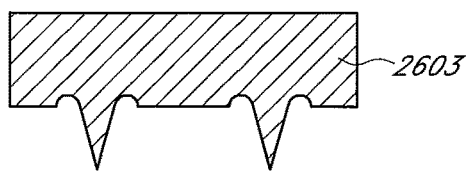

The device is also suitable for use in a method for forming microstructures similar to those shown in FIG. 18L on a planar surface. Turning first to FIG. 26A, the method comprises drawing the blade of the device over a template material 2601, such as a metal or plastic as discussed above, to form a grooved surface on the template material 2601. As shown in FIG. 26B, the method further comprises applying a first impression material 2603 over the grooved surface of the template material 2601. Elastomeric impression materials (e.g., polyethers, polyvinyl siloxanes (PVSs), polyether-PVS hybrids, alginates, silicone, and silicone rubbers) are particularly suitable for this purpose. The first impression material 2603 can be allowed to cure for a period of time, such as 5 minutes (or about 5 minutes). In FIG. 26C, the template material 2601 is removed, leaving the first impression material 2603 with a pattern inverted from that of the template material 2601.

Figure 26D:
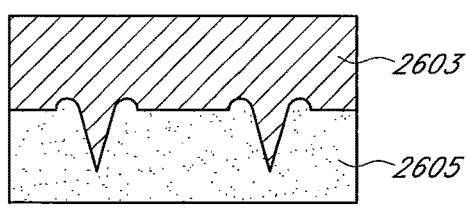
Figure 26E:
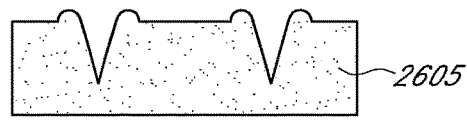

In FIG. 26D, a second impression material 2605 is applied to the first impression material 2603. Again, elastomeric impression materials, such as those identified above, are suitable for the second impression material. The second impression material 2605 can be allowed to cure for a period of time, such as 5 minutes (or about 5 minutes). In FIG. 26E, the first impression material 2603 is removed, leaving the second impression material 2605 with a pattern inverted from that of the first impression material 2603. In other words, the original pattern in the template material 2601 (FIG. 26A) is replicated in the second impression material 2605 (FIG. 26E).

Figure 26F:
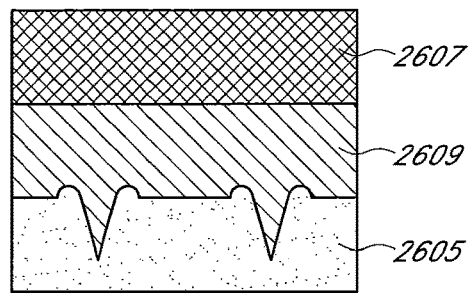
Figure 26G:
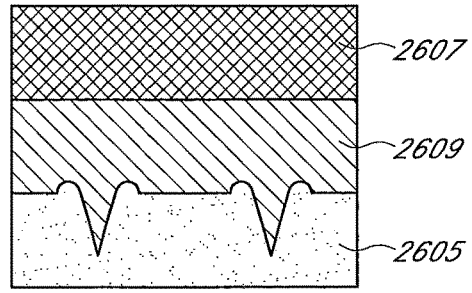
Figure 26H:
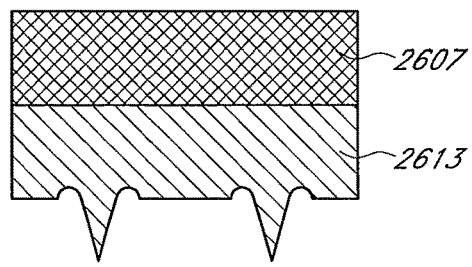

As shown in FIG. 26F, a curable material 2609 is applied between the second impression material 2605 and a target surface 2607. Examples of the target surface 2607 include plastics, such as acrylonitrile butadiene styrene or polycarbonate or metals such as aluminum. For example, the curable material 2609 can be applied to a plastic humidification chamber target surface 2607, and the second impression material 2605 can be overlaid on the curable material 2609. The surface of the target surface 2607 can be roughened, e.g., by sanding, prior to application of the second impression material 2605 to improve adhesion. Suitable materials for the curable material 2609 include UV curable acrylic and heat curable epoxy or heat curable acrylic. When the curable material 2609 is UV curable, either or both of the second impression material 2605 and the target surface 2607 should preferably be permeable to UV (e.g., transparent to light). In FIG. 26F, the target surface 2607 is a transparent plastic, for example. In FIG. 26G, UV light 2611 passes through the target surface 2607 and cures the curable material 2609 to form a hardened overlayer on the target surface 2607. Alternatively, the target surface 2607—curable material 2609—second impression material 2605 complex can be heated, thereby curing the heat curable material 2609. In FIG. 26H, the second impression material 2605 is removed to reveal the target surface 2607 with the hardened overlayer 2613 having a microstructured surface.

Figure 27A:
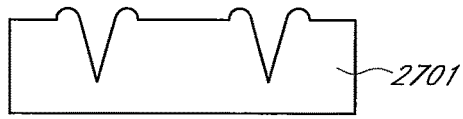
FIGS. 27A-27F illustrate another method for forming microstructures on a planar surface.
Figure 27B:
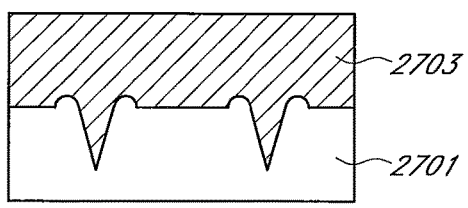
Figure 27C:
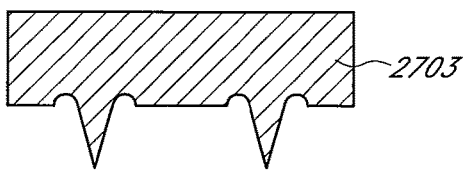

FIGS. 27A-27F show the materials involved in a method similar to that described above with respect to FIGS. 26A-26H. The materials of FIGS. 27A-27F are suitable for forming microstructures similar to those in FIG. 18A on a planar surface. Turning first to FIG. 27A, the method comprises drawing the blade of the device over a template material 2701, such as a metal or plastic as discussed above, to form a grooved surface on the template material 2701. As shown in FIG. 27B, the method further comprises applying an impression material 2703 (such as an elastomeric impression material as discussed above) over the grooved surface of the template material 2701. In FIG. 27C, the template material 2701 is removed, leaving the impression material 2703 with a pattern inverted from that of the template material 2701.

Figure 27D:
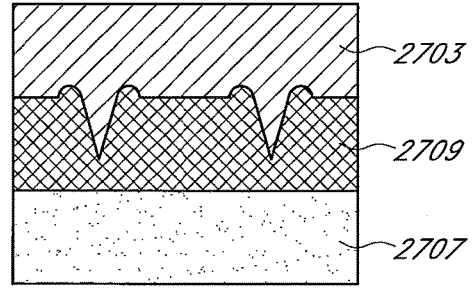

As shown in FIG. 27D, a curable material 2709 (such as a UV-curable or heat curable material as discussed above) is applied between the impression material 2703 and a target surface 2707, such as a metal or plastic planar surface. The surface of the target surface 2707 can be roughened, e.g., by sanding, prior to application of the impression material 2703 to improve adhesion.

Figure 27E:
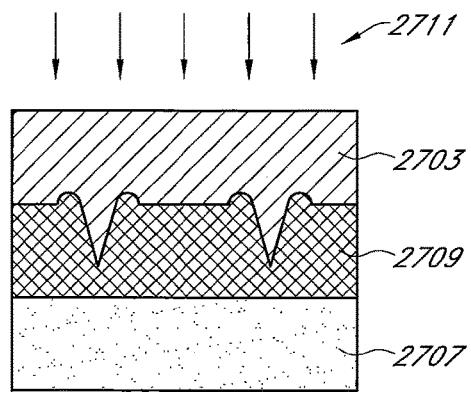
Figure 27F:
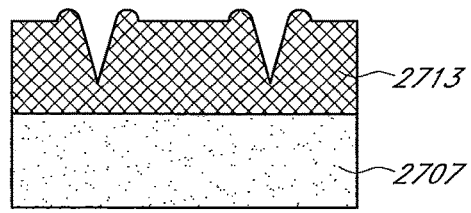

As shown in FIG. 27E, UV light 2711 passes through the impression material 2703 and cures the curable material 2709 to form a hardened overlayer on the target surface 2707. Alternatively, the UV light 2711 can pass through the target surface 2707, if desired. The surface passing the UV light is preferably selected to be transparent to UV light. As discussed above, when the curable material 2709 is heat curable, the target surface 2707—curable material 2709—second impression material 2705 complex can be heated to harden the curable material 2709. In FIG. 27F, the impression material 2703 is removed to reveal the target surface 2707 with the hardened overlayer 2713 having a microstructured surface.

Figure 28A:
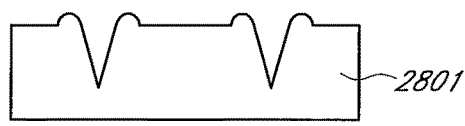
FIGS. 28A-28D illustrate another method for forming microstructures on a planar surface.
Figure 28B:
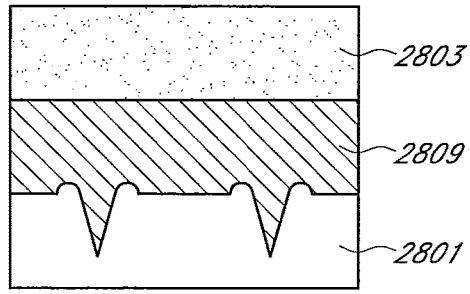
Figure 28C:
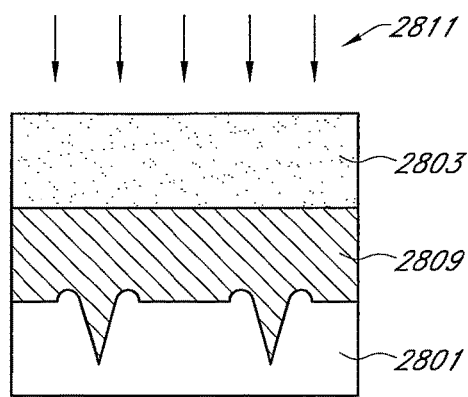
Figure 28D:
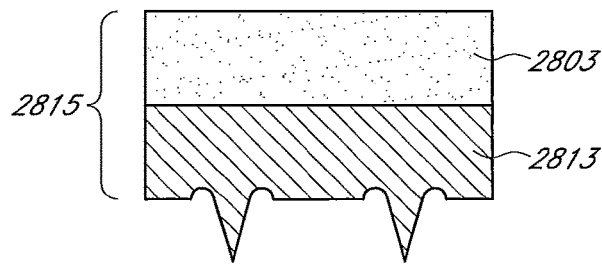

FIGS. 28A-28D show another method for forming microstructures on a planar surface. Turning first to FIG. 28A, the method comprises drawing the blade of the device over a template material 2801, such as a metal or plastic as discussed above, to form a grooved surface on the template material 2801. As shown in FIG. 28B, a curable material 2809 (such as a UV-curable acrylic) is applied between the template material 2801 and an elastomeric molding material 2803, such as silicone. In FIG. 28C, UV light 2811 passes through the molding material 2803 and cures the curable material 2809. In FIG. 28D, the template material 2801 is removed to reveal a mold 2815 comprising a microstructured overlayer 2813 on the molding material 2803. The mold 2815 can then be used to transfer the microstructured pattern to a desired surface.

It should be noted that the relative sizes of the features shown in the figures associated with the foregoing methods are not drawn to scale.

At least one method for forming microstructures comprises providing a cutting blade having a wheel shape, similar to a wheel-type pizza cutter. The cutting blade is similar to the cutting blade 2501 of FIG. 25B, except that the straight fine cutting blade is replaced with the wheel-shaped cutting blade. A schematic cross section of the wheel-shaped cutting blade 2501 is shown in FIG. 25C. The dimensions are not shown to scale. Such a cross section shows dual cutting surfaces 2511, 2513 suitable for forming inverted trapezoidal microstructures in a planar surface. It was further discovered that the wheel-shaped cutting blade 2501 can produce smoother edges and side walls than the straight blade, particularly when cutting metal surfaces. Thus, the inverted trapezoids formed by the cutting blade 2501 of FIG. 25C can lack small channels within the large channels.

The wheel-shaped fine cutting blade 2501 can be used in the foregoing methods. The wheel-shaped cutting blade 2501 is also useful in a method for forming a metal mold suitable for use in injection molding, injection-compression molding, or hot embossing. The method comprises drawing the wheel-shaped cutting blade 2501 of the device over the surface of a mold tool, thereby deforming the surface of the mold tool. The resulting microstructures are thus imprinted in the surface of the mold tool, and the microstructures can be later replicated by injection molding, injection-compression molding, and/or hot embossing, in which a negative shape is reproduced on a surface.

Hot embossing can be particularly desirable, as this process was observed to improve the fidelity of reproduction with a high aspect ratio. For hot embossing amorphous polymers, an advantageous embossing temperature is 30° C. (or about 30° C.) above the glass transition temperature. For hot embossing semi-crystalline polymers, a temperature above the crystalline melt temperature of 10° C. or less (or about 10° C. or less) can be advantageous. An advantageous embossing pressure is 10 MPa (or about 10 MPa).

As discussed above with reference to FIG. 18L, an inverse-trapezoid microstructured surface can comprise small channels within a main channel and taller ridges defining the width of the main channel. The small channels can develop within a main channel as the gap between the taller ridges increases. As shown with reference to FIG. 26A, a precursor step to forming an inverse-trapezoid microstructured surface can include drawing a blade over the template material 2601 to form a grooved surface on the template material 2601. It was unexpectedly discovered that spacing the grooves farther apart together results in shallower grooves and larger displacement bumps, while spacing the grooves closer together results in deeper grooves and smaller displacement bumps. It is believed that, when the grooves are spaced closer together, at least some of the displaced material moves in the direction of maximum sheer stress and flows downward, rather than upward to form the displacement bumps. It was further discovered that the effect is diminished, however, when a harder template material, such as acrylic (M90) or bakelite (M95), rather than a softer template material, such as aluminum or polycarbonate (M70), is selected.

Figure 29A:
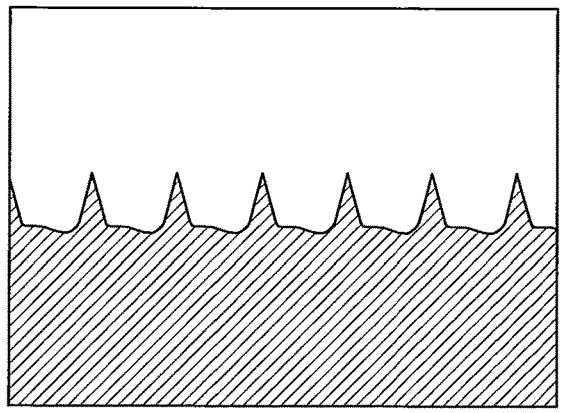
FIGS. 29A-29C illustrate inverted-trapezoid microstructures.
Figure 29B:
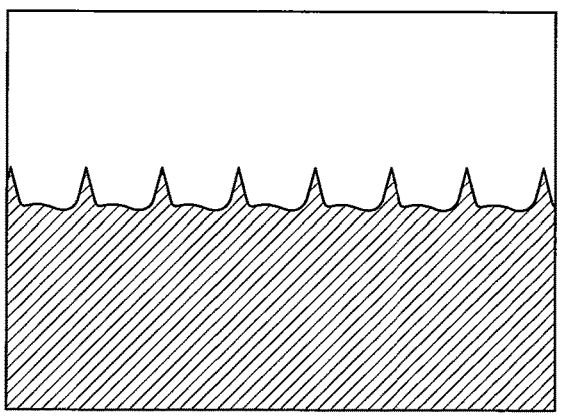
Figure 29C:
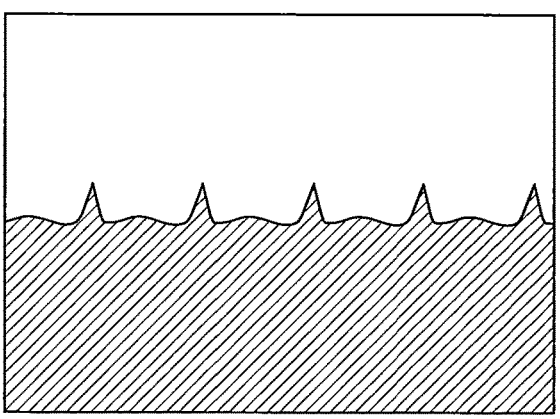

FIGS. 29A-29C illustrate inverted-trapezoid microstructures obtained after inverting the pattern on the template material. The dark portions represent solid microstructures, and the lighter portions represent empty space. The spacing in FIG. 29A is 50 µm; the spacing in FIG. 29B is 70 µm; and the spacing in FIG. 29C is 110 µm. FIGS. 29A-29C illustrate that closer spacing between the taller ridges (corresponding to the grooves of the template material) decreases the height of the shorter ridges, while wider spacing between the taller ridges increases the height of the shorter ridges.

Thus, when small channels are desired, it can be advantageous to space the grooves of the template farther apart to encourage formation of displacement bumps on the template material. It can also be advantageous to select a harder template material to encourage formation of displacement bumps on the template material. To increase the height of the taller ridges, the grooves on the template material can be spaced closer together. It can also be advantageous to select a softer template material to promote greater height of the taller peaks.

A rotating lathe is also useful in a method for forming microstructures. With the lathe, it is possible to form a continuous, microstructured spiral on a flexible surface, such as a plastic surface, wrapped around the lathe. The plastic surface can be removed from the lathe and flattened into the desired shape. If desired, the spiral can be transferred to another surface, as described above.

Flexible Sheet with Microstructures

Figure 30A:
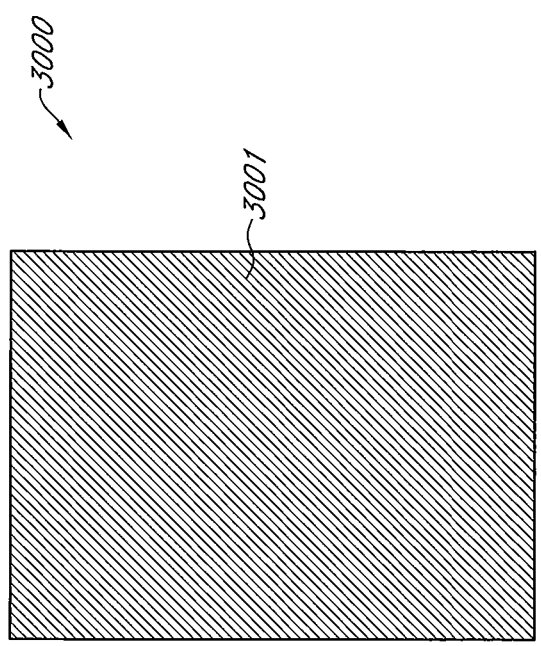
FIG. 30A illustrates a schematic of a microstructured sheet.

Turning next to FIG. 30A, certain embodiments include a flexible planar sheet 3000 comprising microstructures 3001. Any of the microstructures disclosed herein are suitable for use with such a sheet 3000. In FIG. 30A, the microstructures 3001 are shown on a diagonal, as they were formed using a rotating lathe, as described above.

The sheet 3000 can comprise a flexible plastic such a polyester, polyurethane, or polyamide. The plastic can be thermally conductive. For example, the plastic can be dispersed with one or more thermally conductive filler materials, such as graphite, carbon black, carbon nanotubes, carbon fibers, ceramic (e.g., boron nitride, aluminum nitride, beryllium oxide, and/or aluminum oxide) particles, or metal (e.g., copper, silver, gold, aluminum, and/or nickel) particles. One or both outside surfaces of the sheet 3000 can comprise the microstructures 3001. The microstructures 3001 can be formed using a suitable method, such as those described above. One or more conductive filaments, such as a heating filament and/or a sensing filament can be can be disposed in or on the sheet 3000. Preferably, the one or more conductive filaments are disposed within the sheet 3000 such that the one or more conductive filaments do not interfere with the flow of liquid in the microstructures 3001. Nevertheless, other configurations are suitable. For example, the microstructures 3001 can be disposed on one outside surface of the sheet 3000, and a heating filament can be disposed on the other outside surface of the sheet 3000. In certain embodiments, one of the outside surface's comprises a prefixed adhesive to facilitate attachment to a structure, such as a humidification chamber or a patient interface. Alternatively, an adhesive can be applied to an outside surface prior to attachment.

In embodiments comprising heating filaments, it can be desirable to place a large surface area of the microstructures 3001 proximal a heating filament. Accordingly, the heating filament can be arranged in a generally sinuous pattern. However, a variety of configurations are possible, such as a grid-shaped configuration, a coil, or a ring.

Figure 30B:
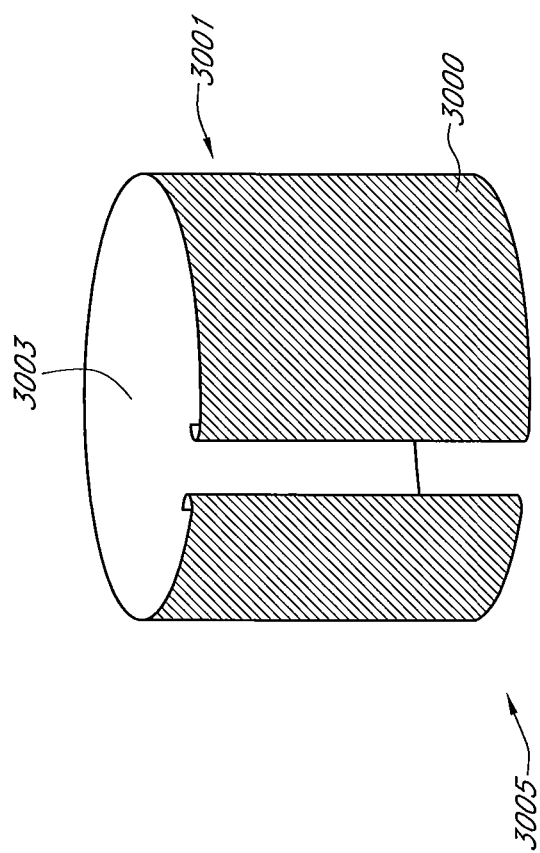
FIG. 30B illustrates a schematic of an insert for use in a humidification chamber comprising the microstructured sheet of FIG. 30A.

Certain embodiments include the realization that microstructures can increase water uptake of gases in a humidification chamber. Microstructures can increase the surface area of a humidification chamber available for vaporization of water. The liquid water is wicked through the microstructures and gas flowing over the microstructures takes up the water as water vapor. Accordingly, the foregoing sheet 3000 can be suitable for use in a humidification chamber insert 3005, as shown in FIG. 30B. The insert 3005 can comprise the flexible, plastic planar sheet 3000 comprising the microstructures 3001 on one or both surfaces. As shown in FIG. 30B, the insert can further comprise a thermally conductive plastic backing 3003 disposed on a surface of the sheet 3000. The backing 3003 is configured to transmit heat from a heating element near the bottom of a humidification chamber and thereby improve evaporation from the microstructures 3001 on the sheet 3000 contacting the backing 3003. The insert 3005 can further comprise one or more conductive filaments, such as one or more heating filaments, in embodiments with or without the backing 3003. The one or more conductive filaments can be arranged as described above.

Humidification Chamber with Microstructures

As discussed above, certain embodiments include the realization that microstructures can increase water uptake of gases in a humidification chamber. Microstructures can increase the surface area of a humidification chamber available for vaporization of water. The liquid water is wicked through the microstructures and gas flowing over the microstructures takes up the water as water vapor.

Figure 7:
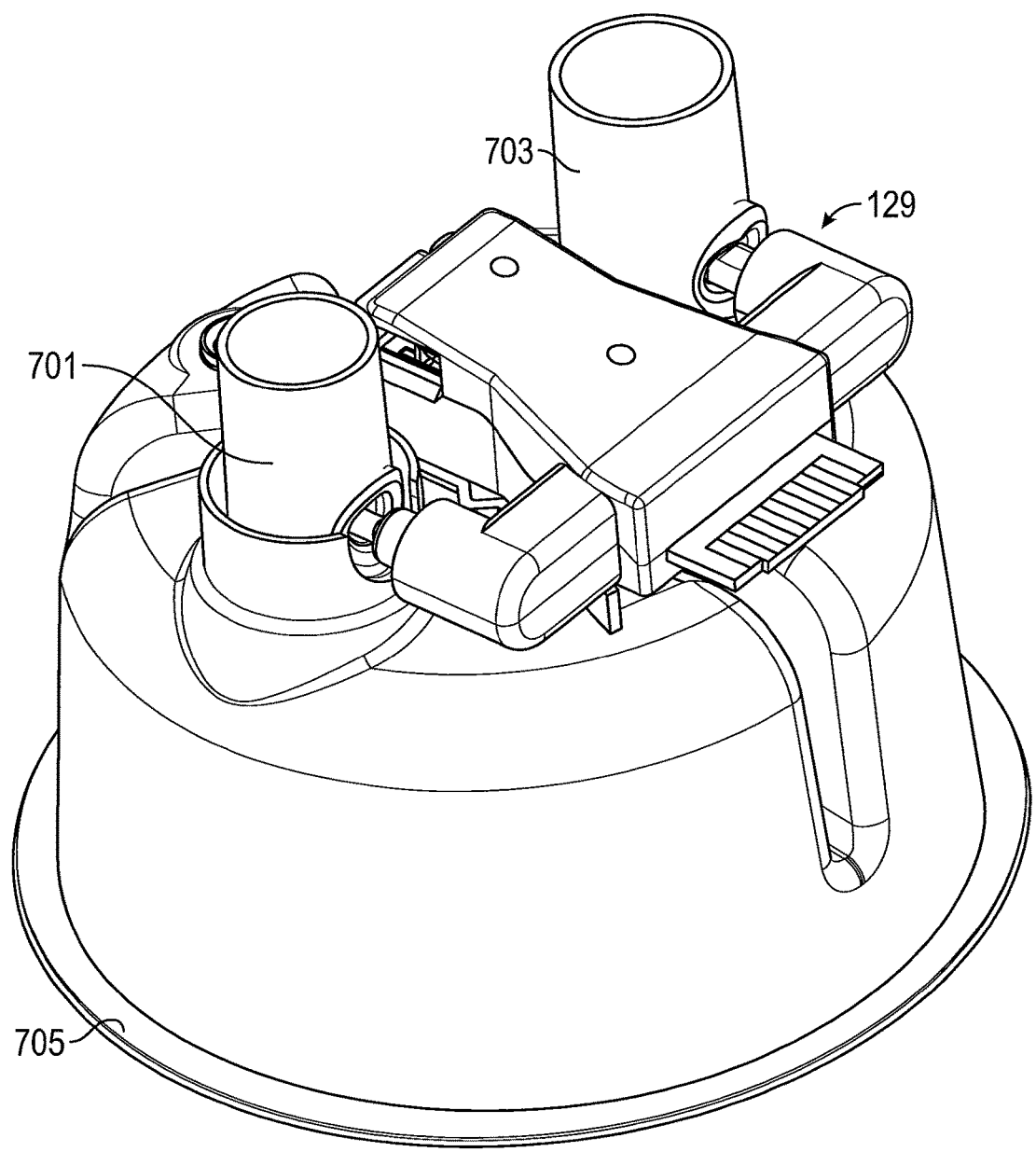
FIG. 7 shows a perspective view of an example humidification chamber.

Reference is next made to FIG. 7, which shows the humidification chamber 129 according to at least one embodiment. The humidification chamber 129 generally comprises the inlet port 701 and an outlet port 703. The humidification chamber 129 is configured to be installed on a heater plate (discussed above as the heater plate 131 of FIG. 1), such that a base 705 of the humidification chamber 129 contacts the heater plate 131. The base 705 preferably comprises a metal with good thermal conductivity, such as aluminum and copper. The humidification chamber 129 is further configured to hold a volume of a liquid, such as water. In use, the liquid contacts a substantial portion of the base 705. The heater plate 131 heats the base 705 of the humidification chamber 129, thereby causing at least some of liquid in the humidification chamber 129 to evaporate. In use, gases flow into the humidification chamber 129 via the inlet port 701. The gases are humidified within the humidification chamber 129 and flow out of the humidification chamber 129 through the outlet port 703.

Figure 8A:
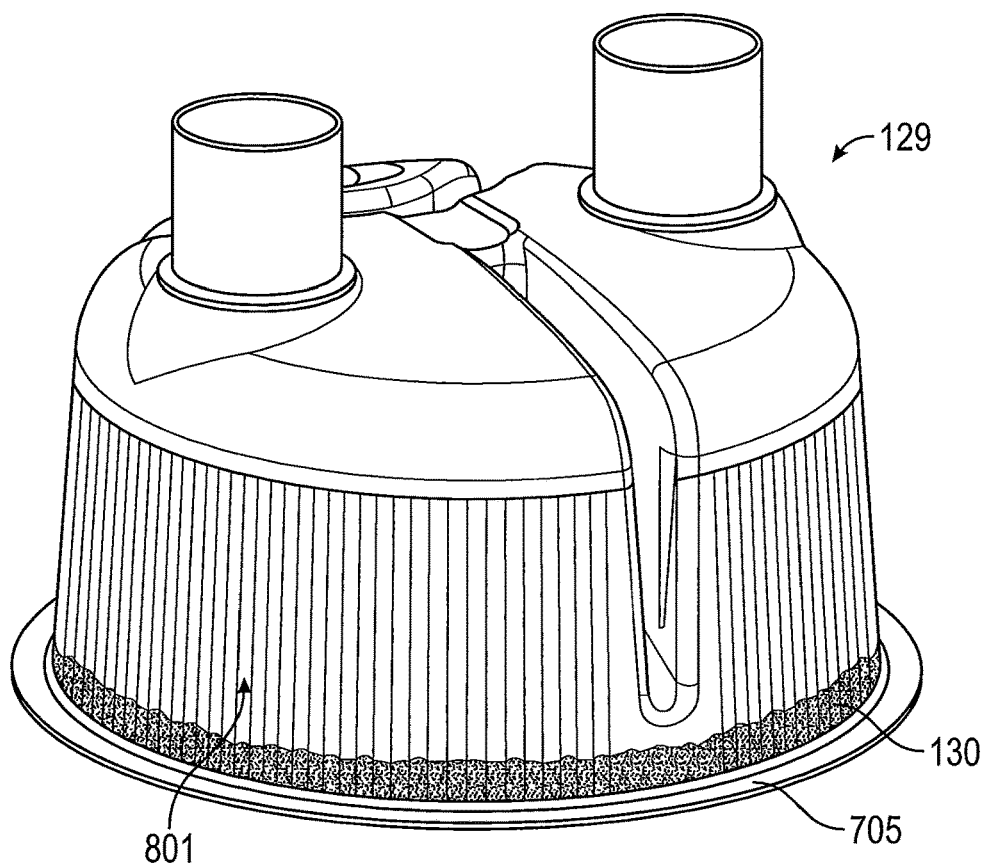
FIG. 8A shows a perspective view of an example humidification chamber, including a first configuration of microstructures.

FIG. 8A shows an example configuration for microstructures 801 of the humidification chamber 129. The properties of the microstructures 801 discussed in the preceding section are incorporated by reference. As shown in this example, the microstructures 801 are arranged vertically around a circumference of the humidification chamber 129 on the interior wall. In other words, the microstructures 801 are perpendicular (or generally perpendicular) to the base 705 of the humidification chamber 129. The microstructures 801 in FIG. 8A are shown larger than actual size for illustrative purposes only. The vertical microstructures 801 carry the water 130 up the sides of the humidification chamber 129 so that a greater surface area of the water 130 is exposed to the air flow within the humidification chamber 129. In at least one embodiment, the microstructures 801 extend from the base of the humidification chamber 129 to a distance of 100%, 99%, 95%, between 95-99%, 90%, or between 90-95% (or thereabout) of the height of the humidification chamber 129. The humidification chamber 129 height can be 50 mm (or about 50 mm). In certain configurations, one or more additives, such as SILWET surfactant (Momentive Performance Materials, Inc. of Albany, N.Y. USA) can be included in the water 130 to enhance uptake by the microstructures 801.

Although in FIG. 8A, the microstructures 801 are arranged around the entire circumference of the humidification chamber 129, it should be understood that, in certain embodiments, the microstructures 801 are arranged in less than the entire circumference. For example, the microstructures 801 can be arranged in a single portion of the humidification chamber 129 or in random or fixed intervals around the humidification chamber 129.

Figure 8B:
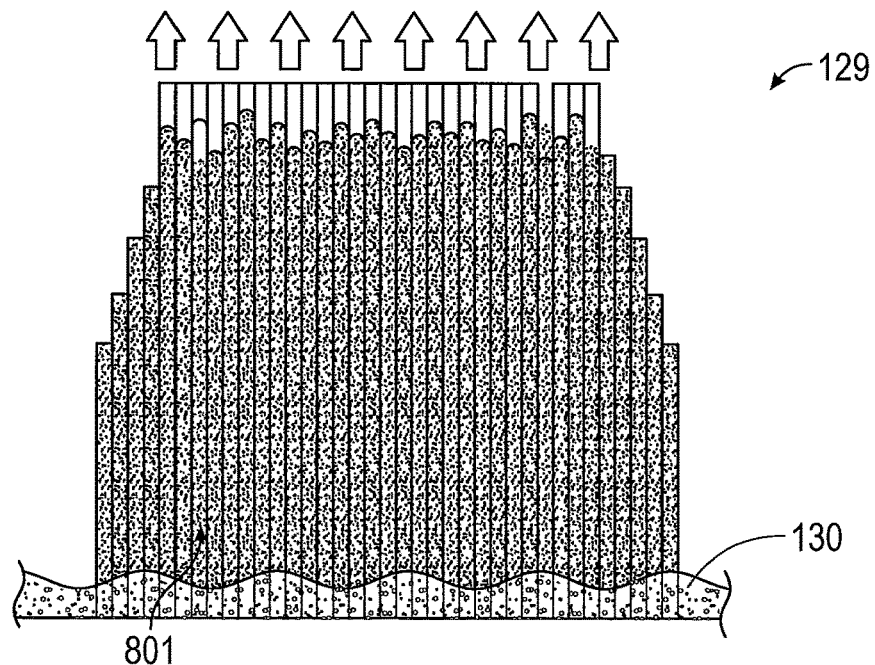
FIGS. 8B and 8C show front plan views of first and second magnified portions of the microstructures in FIG. 8A.
Figure 8C:
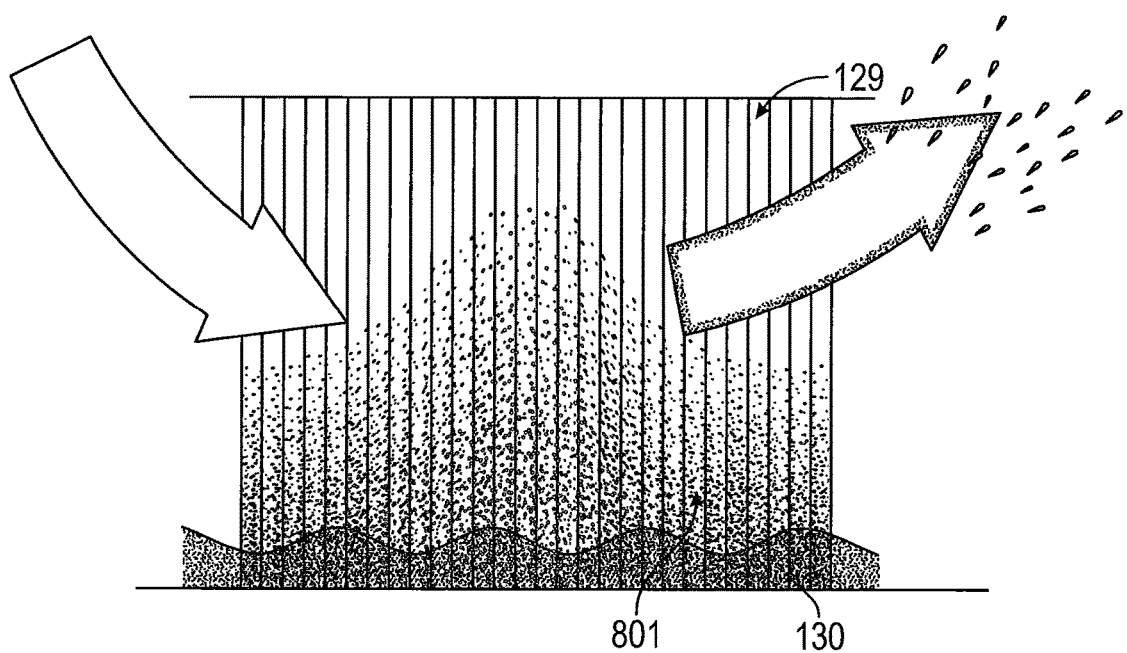

FIG. 8B shows a first magnified view of a portion of the microstructures 801 of FIG. 8A. As shown in FIG. 8B, the water 130 travels up the vertical microstructures 801. Microscale water droplets in or on the microstructures 801 are exposed to the air flow within the humidification chamber 129. FIG. 8C shows a second magnified view of a portion of the microstructures 801 of FIG. 8A. As shown in FIG. 8C, air flows through the humidification chamber 129 and across the microstructures 801, causing at least some of the water droplets in the microstructures 801 to evaporate. The evaporated water from the microstructures 801 enters the air flow as a vapor.

As shown in the foregoing figures, the microstructures 801 expose a greater surface area of the water 130 in the humidification chamber 129 to the passing air flow, thereby increasing the efficiency of the humidification chamber 129, compared with a humidification chamber without any microstructures.

Figure 8D:
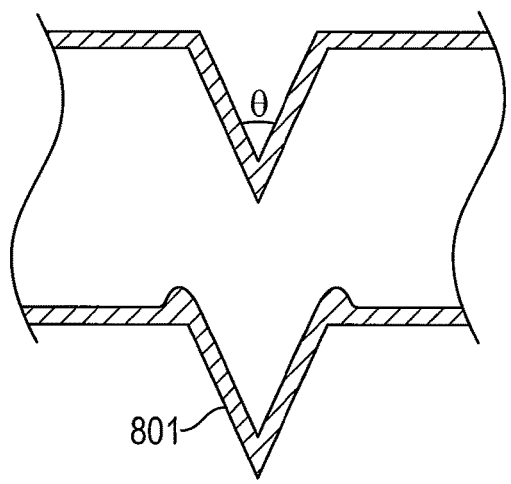
FIG. 8D shows a cross section of an example microstructure.

FIG. 8D illustrates a cross section of an example one of the microstructures 801. In this example embodiment, the one of the microstructures 801 is a wedge-shaped microchannel. The properties of other microstructures described herein can also be incorporated into the microstructures 801 for the humidification chamber 129 configuration.

Figure 9A:
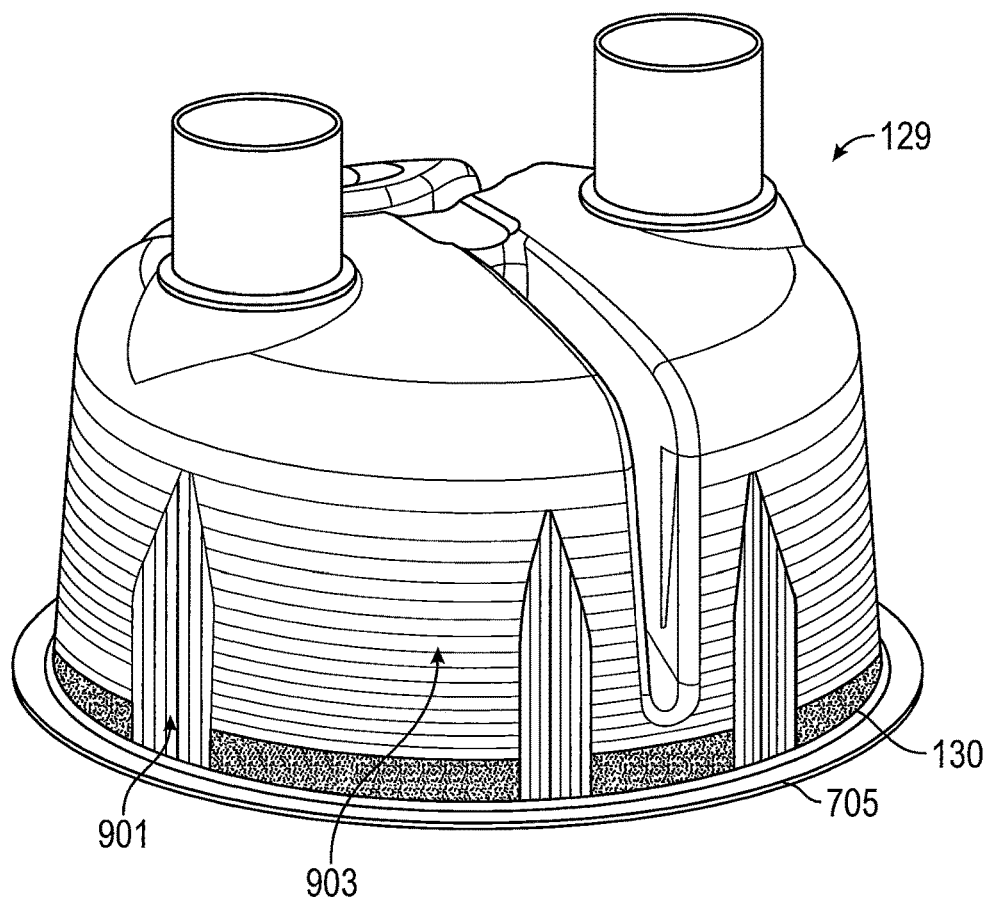
FIG. 9A shows a perspective view of an example humidification chamber, including a second configuration of microstructures.

FIG. 9A shows another example configuration for microstructures of the humidification chamber 129. As shown, microstructures can be arranged vertically and horizontally within the humidification chamber 129. The vertically-arranged microstructures are perpendicular (or generally perpendicular) to the base 705 and are designated 901, and the horizontally-arranged microstructures are parallel (or generally parallel) to the base 705 and are designated 903. Again, the microstructures 901 and 903 are shown larger than actual size for illustrative purposes only. In general, in the configuration of FIG. 9A, the vertically-arranged microstructures 901 carry the water 130 up the sides of the humidification chamber 129. The horizontally-arranged microstructures 903 spread the microscale water droplets from the vertically-arranged microstructures 901 around the top of the humidification chamber 129, exposing a greater surface area of water to the air flow compared to a humidification chamber without any microstructures. The microstructures 901 and 903 thereby increase the efficiency of the humidification chamber 129.

Figure 9B:
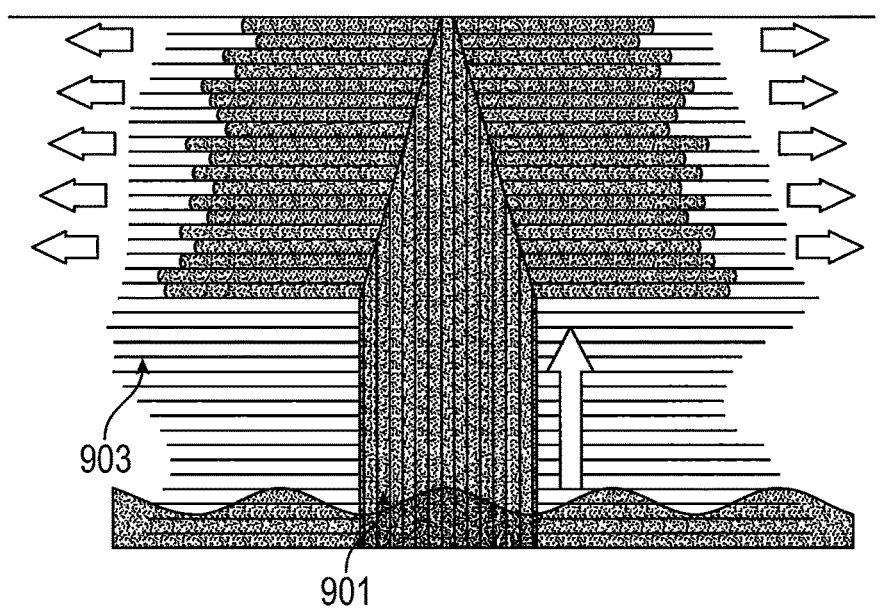
FIGS. 9B and 9C show front plan views of first and second magnified portions of the microstructures in FIG. 9A.
Figure 9C:
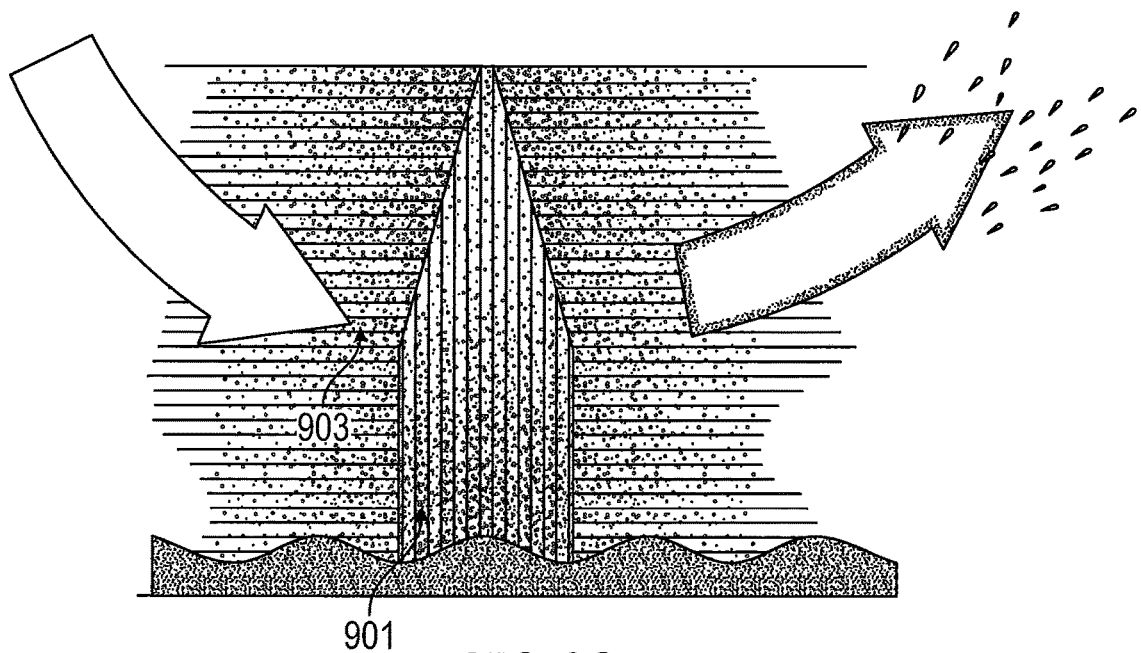

FIG. 9B shows a first magnified view of a portion of the microstructures 901 and 903 of FIG. 9A. As shown in FIG. 9B, water travels up the vertically-arranged microstructures 901. When a microscale water droplet reaches the top of its respective vertically-arranged microstructure 901, the water droplet then travels along its corresponding horizontally-arranged microstructure 903 (or group of microstructures). FIG. 9C shows a second magnified view of a portion of the microstructures 901 and 903 of FIG. 9A. As shown in FIG. 9C, air flows through the humidification chamber 129 and across the microstructures 901 and 903, causing at least some of the water droplets in the microstructures 901 and 903 to evaporate. The evaporated water from the microstructures 901 and 903 enters the air flow as a vapor. In an alternative configuration (not show), the humidification chamber 129 can be configured to let the water run down the microstructures with gravity, rather than against it. Moreover, a combination of channels and pins can direct the flow in any desired fashion.

Figure 9D:
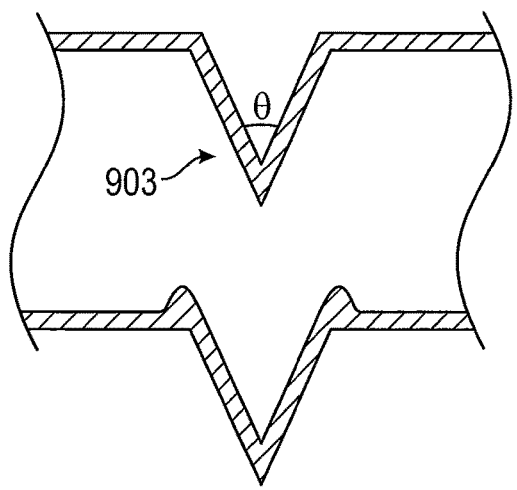
FIG. 9D shows a cross section of an example microstructure.

The vertical microstructures 901 can be similar to those shown above in FIG. 8D and elsewhere in this disclosure and the above discussion of their shapes and properties is incorporated by reference here. FIG. 9D illustrates a cross section of an example horizontal microstructure 903.

The shape and configuration of vertically-arranged microstructures 901 and the horizontally-arranged microstructures 903 in FIGS. 9A-9D is for illustrative purposes only. The invention is not limited to the disclosed embodiment.

For the reasons explained above with respect to the tube embodiments, it can be desirable to utilize microstructures in combination with a surface having a desirable surface energy, in order to improve the surface's wettability and water spreading characteristics. Metals and glass are known to have relatively high surface energies and good wettability. Accordingly, the inner surface of the humidification chamber 129 can comprise a metal or glass. A metal such as aluminum or copper can be desirable because these materials also readily conduct heat, which can improve evaporation rates within the humidification chamber 129. Glass can be desirable because its optical transparency can allow a user to visually inspect the liquid level within the humidification chamber 129. Plastics are particularly desirable materials for the humidification chamber 129 because of their low cost and ease of use in manufacture. As explained above, however, plastics have relatively low surface energies. Accordingly, it can be desirable to treat the plastic with an additive for increasing surface energy, as explained above. In at least one configuration, the humidification chamber 129 wall comprises poly(methyl methacrylate) plastic with the inner wall coated with a layer of conductive metal, such as gold. In another configuration, the inner surface of the humidification chamber 129 wall comprises a ceramic material, garnet, or a sintered material such as $TiO_2$.

As noted above, it was discovered that the addition of heat to a microstructured surface can dramatically improve evaporation rates. Accordingly, the humidification chamber 129 can incorporate a heating filament in the wall, which can improve heating of the wall and, thus, the likelihood that liquid in or on the microstructures will evaporate. In at least one configuration, a heating shroud can be placed around the humidification chamber 129 to improve heat transfer to the humidification chamber 129. In addition, an insulating jacket can be placed around the humidification chamber 129 to prevent heat loss and improve heat retention within the humidification chamber 129.

Figure 23:
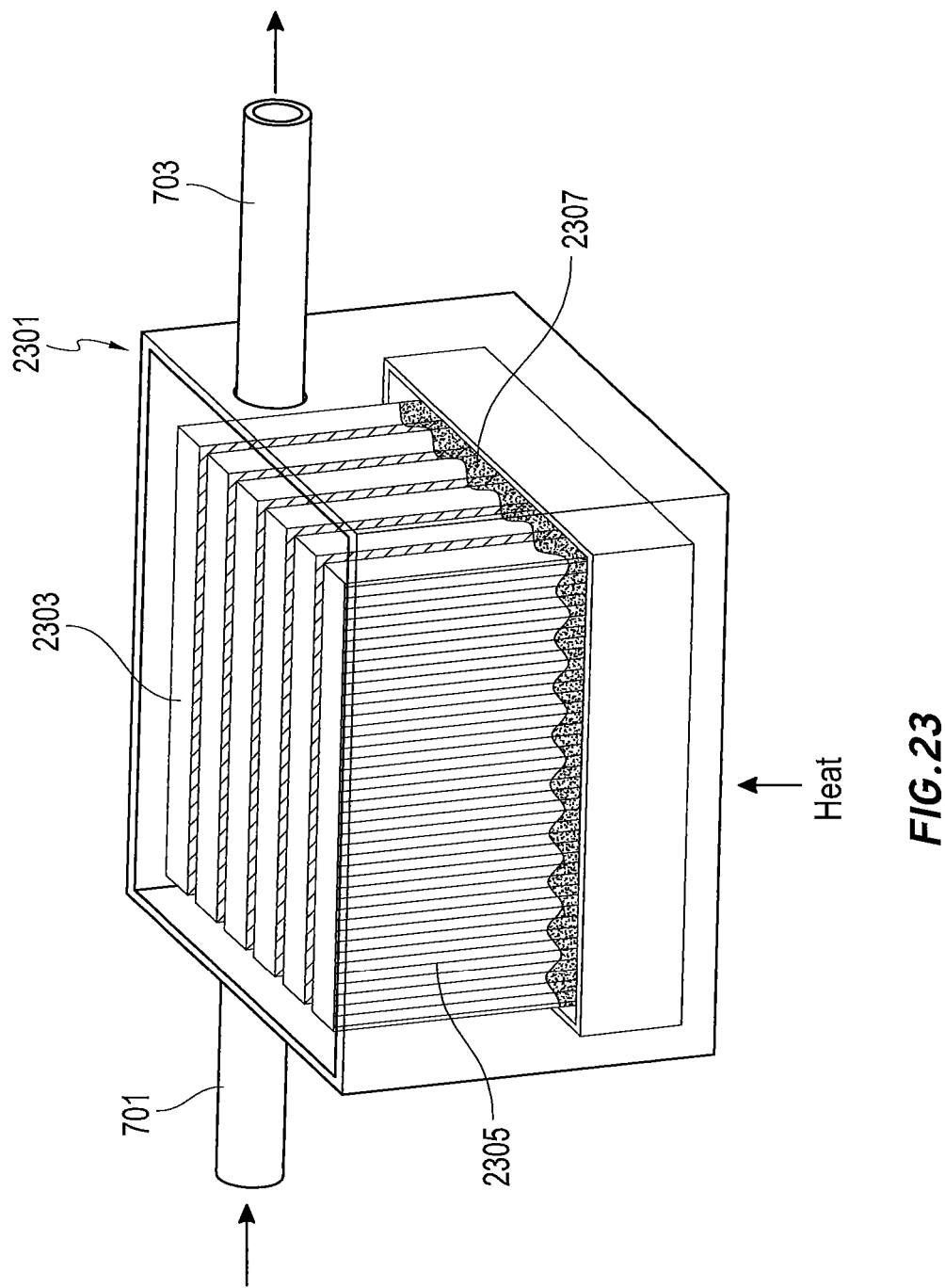
FIG. 23 illustrates an embodiment of a humidification chamber that includes evaporations stacks or towers.

FIG. 23 illustrates an embodiment of a humidification chamber 2301 that includes a number of stacks 2303 having microstructures 2305 on at least some of the surfaces of the stacks 2303. As illustrated, the stacks 2303 may be arranged as a number of fins or walls; however, other configurations can include towers, columns, or a combination of fins, towers, and columns. As shown, the stacks 2303 can be arranged as fins oriented in the direction of the air flow through the humidification chamber 2301. However, other configurations could also be used so as to extend into the flow through the humidification chamber 2301 and induce greater mixing and interaction with the microstructures 2305 and, therefore, evaporation. Moreover, in some embodiments, different stacks may have different heights so as to create irregular flow patterns or turbulent flow for the gas passing through the humidification chamber 2301.

In the illustrated embodiment, the humidification chamber 2301 may be heated. In some embodiments, one or more of the plurality of stacks 2303 may comprise a thermo-conductive material, such as a metal, to further enhance evaporation. In some embodiments all exposed surfaces of each one of the plurality of stacks 2303 may incorporate the microstructures 2305, which can draw water 2307 up from the bottom of the humidification chamber 2301 to portions of the humidification chamber 2301 having increased air flow or where the air is less humid and could, therefore, evaporate more of the water. The humidification chamber 2301 is illustrated as a square box; however, other shapes could be used, such as rectangles, cylinders, spheres, domes, etc.

Microstructures can be incorporated into any number of structures within a humidification system. One such structure is the base or bottom of a humidification chamber itself. In some embodiments, the use of microstructures or irregular surface features on the bottom of a humidification chamber can disperse a fluid and create a larger surface area for enhanced evaporation. In some embodiments, the use of microstructures may act to decrease the depth of the liquid thereby enhancing evaporation. In some embodiments, the microstructures can be configured into a pattern, such a lined or straight pattern or a circular pattern. In some embodiments, a lined or straight pattern increases the surface area better than a circular pattern. In some embodiments, there is no pattern and the surface comprises irregular protrusions or surface irregularities.

Guide Walls for Use in Humidification Chamber

Figure 31:
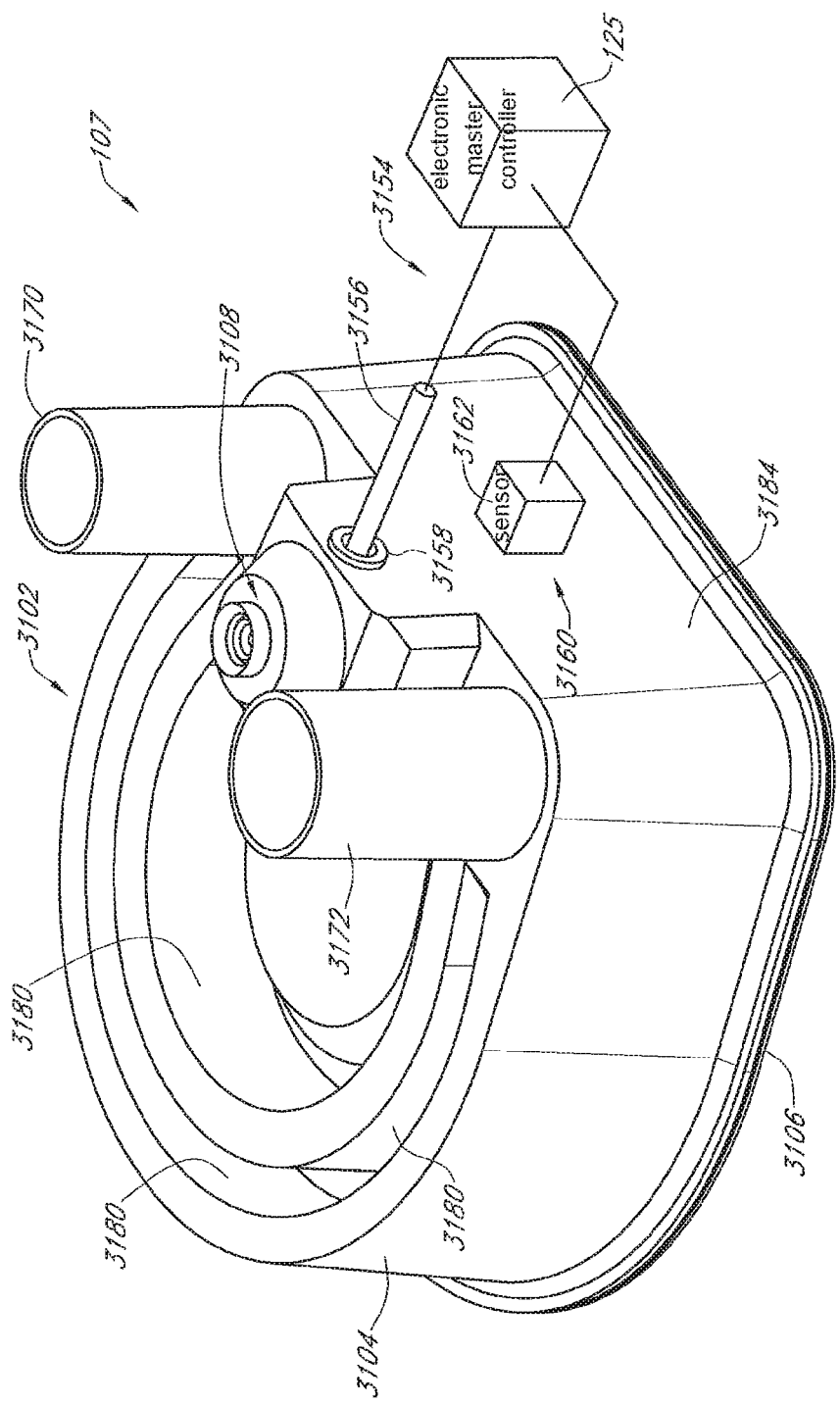
FIG. 31 illustrates a humidification chamber that includes guide features for guiding a flow of gases through the humidification chamber.
Figure 32:
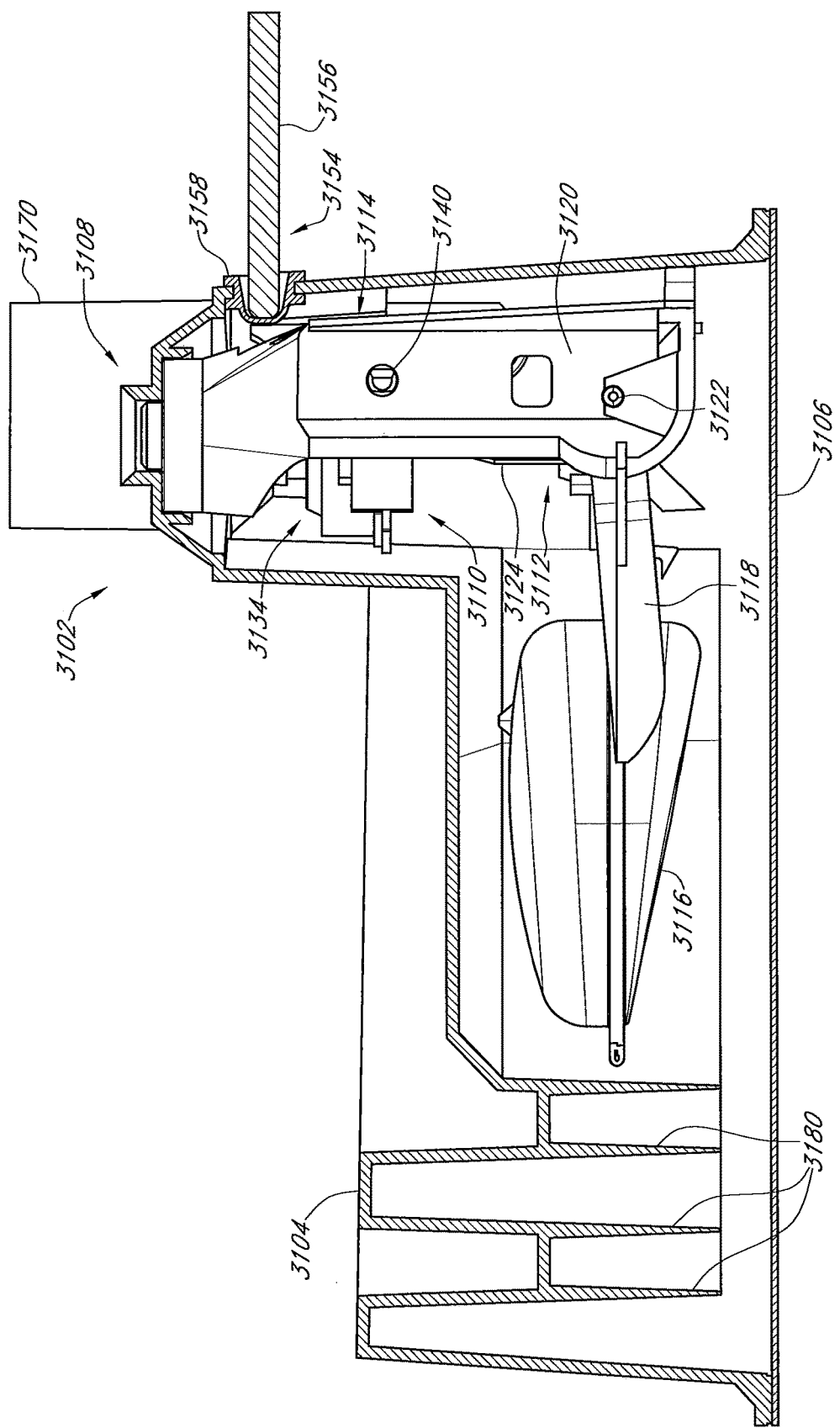
FIG. 32 is a partial sectional view of the humidification chamber of FIG. 31 illustrating the guide features, a dual valve arrangement and an actuator for a secondary valve of the dual valve arrangement.
Figure 33:
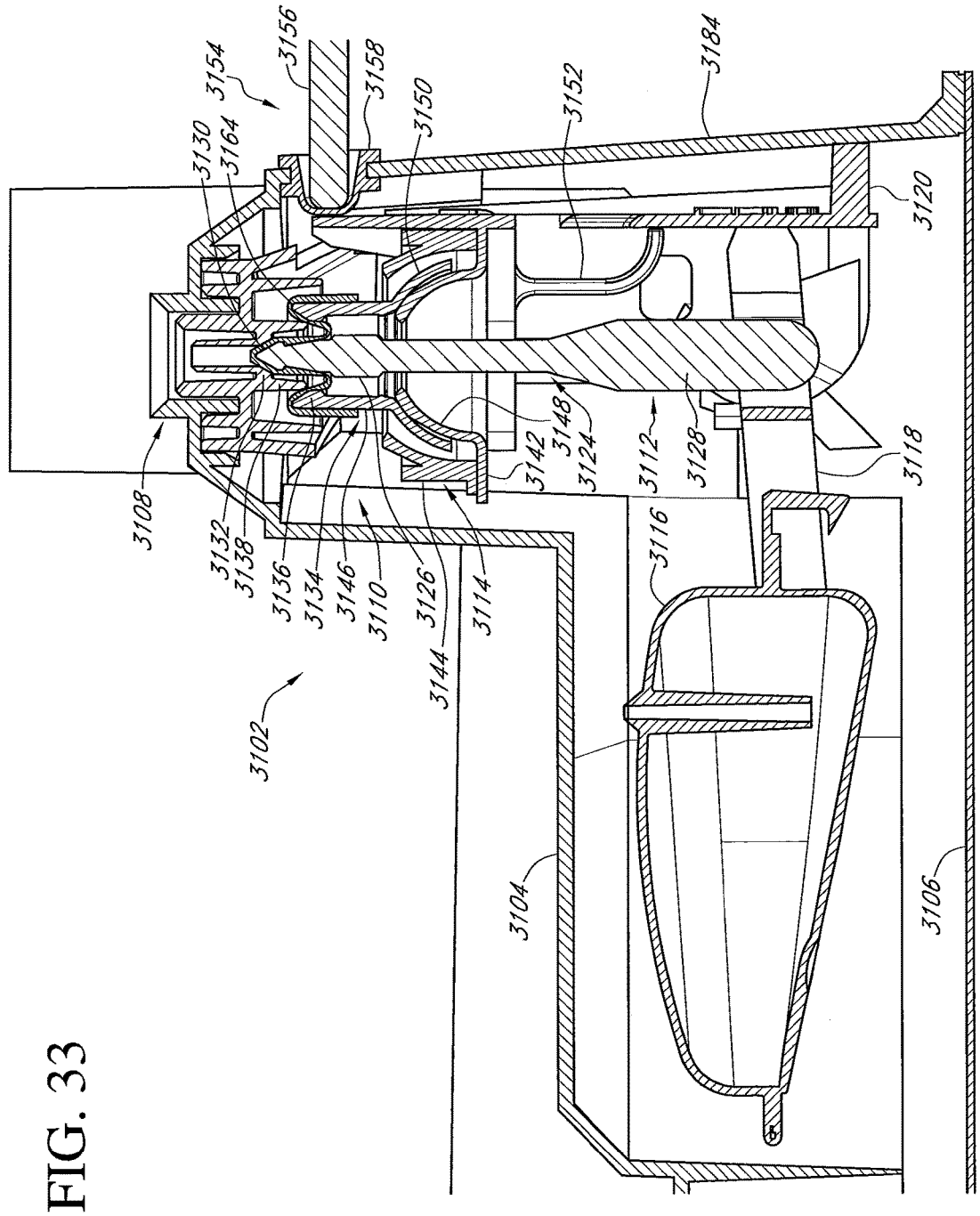
FIG. 33 is a sectional view of the dual valve arrangement of the humidification chamber of FIG. 31.
Figure 34:
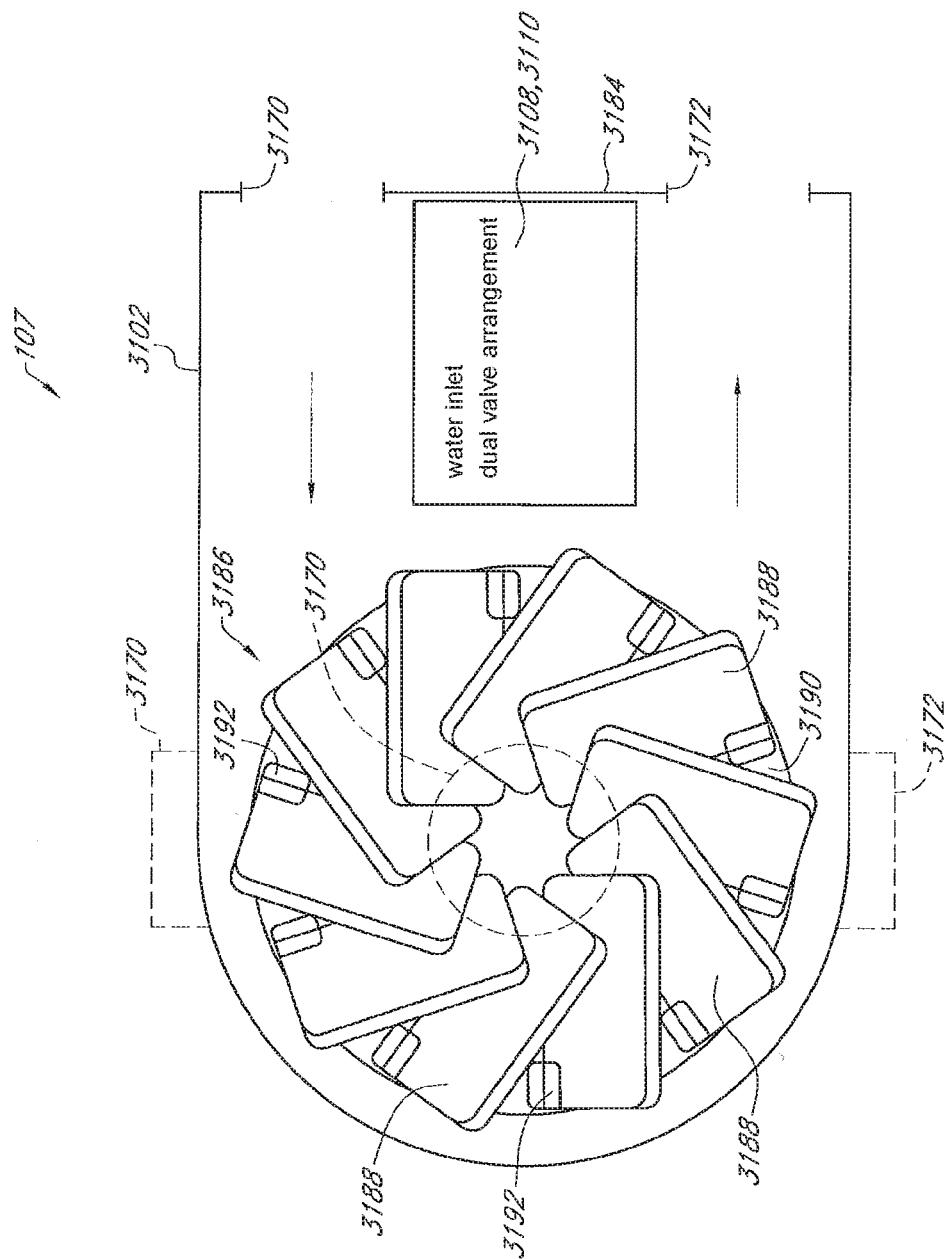
FIG. 34 is a schematic top view of a humidification chamber including a mixing element in the form of a turbine.
Figure 35:
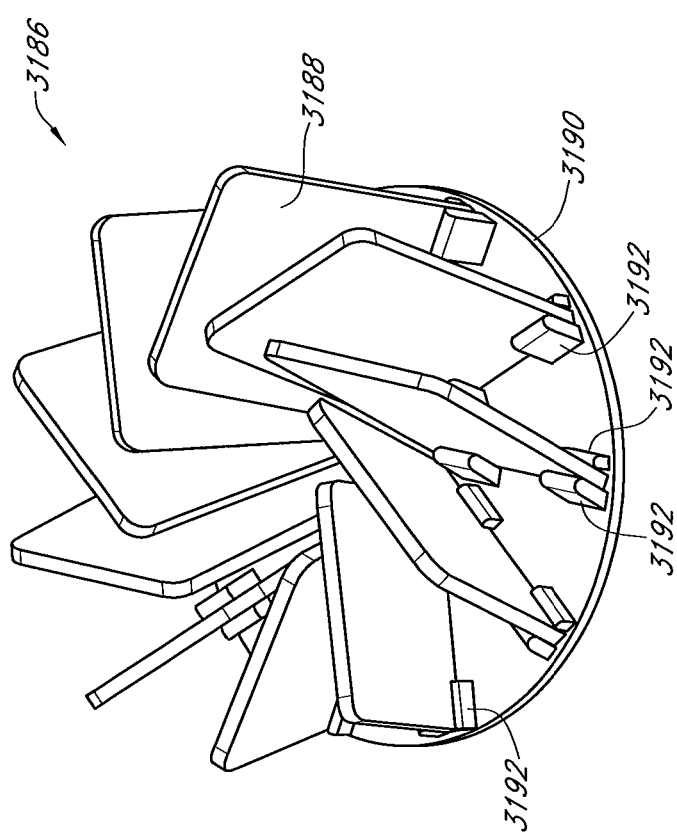
FIG. 35 is a perspective view of the turbine of FIG. 34 separate from the humidification chamber.
Figure 36:
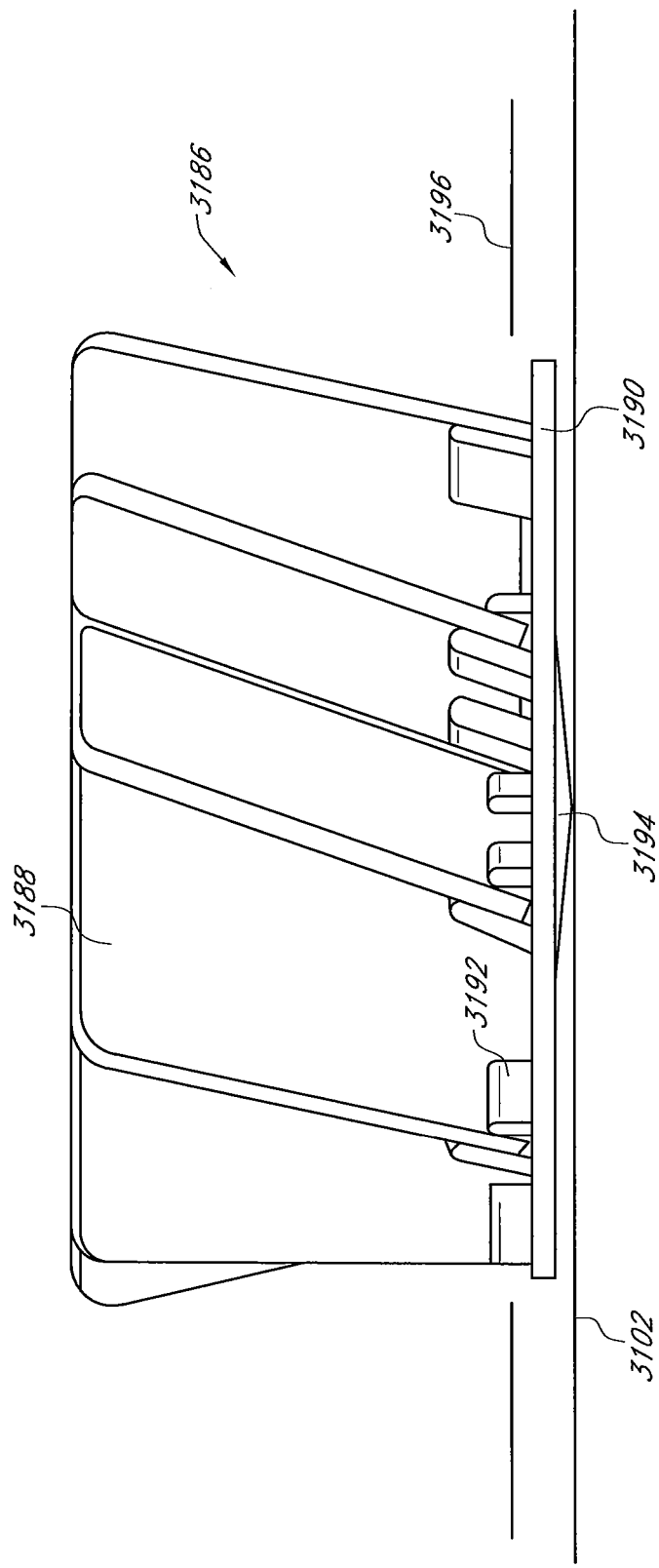
FIG. 36 is a side view of the turbine of FIG. 34 illustrating a friction-reducing feature on the bottom surface of the turbine.

With reference to FIGS. 31-33, a humidification chamber 3102 for fitting to the humidifier 107 (for example as shown in FIG. 1) preferably comprises a humidification chamber body 3104 coupled to a heat transfer base 3106 that is constructed from a heat-conductive material (e.g., aluminum) A water reservoir (not shown) supplies liquid water to the humidification chamber 3102 through a water inlet 3108 in use. The humidification chamber 3102 contains water in both liquid and vapor phases as a result of heat energy supplied through the heat transfer base 3106 by the heater plate 131 on the humidifier 107. The humidification chamber 3102 can be similar in many respects to the humidification chamber 129 disclosed herein. Features of the humidification chamber 3102 not described in detail can be similar to corresponding features of the humidification chamber 129 or can be of another suitable arrangement.

Liquid water enters the humidification chamber 3102 through the water inlet 3108 and rises to a level dependent on the amount of water allowed to enter the humidification chamber 3102 by a suitable control arrangement, such as one or more valves. In the illustrated arrangement, a dual valve arrangement 3110 controls the entry of liquid water from the water reservoir or other water supply into the humidification chamber 3102. The dual valve arrangement 3110 comprises a primary valve system 3112 and a secondary valve system 3114. In some configurations, at least one of the primary valve system 3112 and the secondary valve system 3114 is controlled by a float. In the illustrated arrangement, the primary valve system 3112 is controlled by a primary float 3116, which can be at least partially constructed of an air or gas-filled, sealed element or other buoyant structure which is able to rise and fall with the water level. Preferably, the secondary valve system 3114 is not controlled by a float, but is operated by an alternative arrangement so that the usual secondary float can be omitted thereby providing space for other advantageous features, as described hereinbelow. In some configurations, neither the primary valve system 3112 nor the secondary valve system 3114 is controlled by a float. Instead, each valve system 3112, 3114 is controlled by an alternative arrangement, such as a water level sensor and actuator arrangement. Thus, either or both of the primary valve system 3112 and the secondary valve system 3114 can be controlled by a float or by an alternative arrangement, such as a sensor-based actuator, for example. Float controlled valves are often normally open and are closed as a result of a rise in water level within the humidification chamber 3102. Sensors and valve actuators can be normally open or normally closed and can be moved to the other position by the actuator. An advantage of replacing float valves with a sensor and actuator valve is to avoid covering water surface area with a float to increase the surface area available to produce water vapor.

The illustrated first or primary float 3116 includes a coupling arrangement, such as a coupling arm 3118, which is pivotally connected to a hinge bracket 3120 by a pair of pivot members 3122 (only one shown), which together define an axis of rotation of the primary float 3116. The hinge bracket 3120 can be supported by the humidification chamber body 3104. For example, an upper portion of the hinge bracket 3120 can be coupled (e.g., fastened, snap-fit or bonded) to the water inlet 3108 portion of the humidification chamber body 3104 and, if desired, a lower portion of the hinge bracket 3120 can rest against a side surface of the humidification chamber body 3104. Thus, the primary float 3116 rises and falls along with the water level within the humidification chamber 3102.

The primary float 3116 actuates the primary valve system 3112. In particular, the primary float 3116 moves a push rod 3124, which includes a first portion or lower end portion 3128 pivotally coupled to the coupling arm 3118 of the primary float 3116 and a second portion or upper end portion 3126. The upper end portion 3126 includes a valve body 3130 that cooperates with a first valve seat 3132 of the dual valve arrangement 3110. The valve body 3130 and first valve seat 3132 form a portion of the first or primary valve system 3112. The valve body 3130 can engage the first valve seat 3132, directly or indirectly, to close the primary valve system 3112 and create at least a substantial seal that inhibits or substantially prevents water from entering the humidification chamber 3102 via the primary valve system 3112. The valve body 3130 can also be disengaged from the first valve seat 3132 to open the primary valve system 3112 and permit entry of water into the humidification chamber 3102. The primary float 3116, coupling arm 3118, push rod 3124 and first valve seat 3132 are sized, proportioned, arranged or otherwise configured to close the primary valve system 3112 once a desirable water level within the humidification chamber 3102 is reached and to open the primary valve system 3112 when the actual water level falls below the desirable water level thereby preferably maintaining the actual water level at or near the desirable water level.

The secondary valve system 3114 operates in conjunction with the primary valve system 3112 as a redundant or failsafe arrangement. Preferably, the primary valve system 3112 controls the entry of water into the humidification chamber 3102 under normal operating conditions. However, if the primary valve system 3112 should malfunction or, for whatever reason, the water level should rise above the desirable water level, the secondary valve system 3114 preferably closes to inhibit or stop water from entering the humidification chamber 3102. The secondary valve system 3114 can also open when the water level falls below the desirable water level to permit refill of water and continued use of the humidifier 107.

The secondary valve system 3114 includes a movable valve body assembly 3134 that is movable between a closed position, in which a valve body element 3136 directly or indirectly contacts a second valve seat 3138 of the secondary valve system 3114 to inhibit or stop water from entering the humidification chamber 3102 through the secondary valve system 3114, and an open position, in which the valve body element 3136 does not contact the second valve seat 3138 of the secondary valve system 3114 so that water is permitted to enter the humidification chamber 3102 through the secondary valve system 3114. The valve body assembly 3134 can be normally biased to one of the open or closed positions and can be moved to the other of the open or closed positions, as appropriate, by a suitable actuator. In some configurations, the valve body assembly 3134 is normally biased to the closed position and is biased to the open position under certain conditions, such as when the humidification chamber 3102 is appropriately assembled to the humidifier 107.

In the illustrated arrangement, the valve body assembly 3134 is pivotally connected to the hinge bracket 3120 by a pair of pivot members 3140 (only one shown). The illustrated valve body assembly 3134 includes a base 3142 and a retainer cap 3144 that support a secondary push tube 3146 therebetween. The base 3142 defines or carries the pivot members 3140. The secondary push tube 3146 defines or carries the valve body element 3136. Preferably, the base 3142 defines a hemispherical portion 3148 and the secondary push tube 3146 defines a complementary hemispherical portion 3150 that cooperate to form a ball-joint arrangement, which permits rotation of the secondary push tube 3146 relative to the base 3142 about two axes of rotation. Accordingly, a desirable orientation of the secondary push tube 3146 can be maintained throughout a range of pivotal movement of the base 3142. The retainer cap 3144 can be secured to the base 3142 by any suitable arrangement, such as a snap-fit arrangement, mechanical fasteners, adhesives or ultrasonic welding, for example and without limitation. Preferably, a space is provided between the retainer cap 3144 and the secondary push tube 3146 such that the retainer cap 3144 inhibits separation of the secondary push tube 3146 from the base 3142, while allowing for relatively free movement of the secondary push tube 3146 relative to the base 3142.

The illustrated valve body assembly 3134 is normally biased to a closed position by a biasing element or elements, such as one or more spring arms 3152. Preferably, a pair of laterally-spaced spring arms 3152 (only one shown) are provided that are unitarily-formed with the base 3142. The illustrated spring arms 3152 project downwardly from the hemispherical portion 3148 and contact the hinge bracket 3120. The spring anus 3152 can be curved, as illustrated, or can be relatively or substantially straight. Straight spring arms could be angled relative to the remainder of the base 3142 and project in downward and rearward directions to contact the hinge bracket 3120. The illustrated spring arms 3152 initially project generally straight down from the remainder of the base 3142 and curve in a rearward direction at the ends into contact with the hinge bracket 3120. Other biasing arrangements could also be used, including biasing elements that are separate from the base 3142, retainer cap 3144 or other illustrated components of the valve body assembly 3134. Regardless of the particular arrangement, preferably, the spring arms 3152 are configured to provide a biasing force tending to bias the valve body assembly 3134 toward the closed position.

Preferably, the humidifier 107 includes a mechanism for moving the valve body assembly 3134 into an open position against the biasing force of the spring arms 3152. In particular, the valve body assembly 3134 preferably is moved to the open position during normal operation of the humidifier 107, such as when the humidification chamber 3102 is positioned onto a base of the humidifier 107. In the illustrated arrangement, the humidifier 107 includes an actuator arrangement 3154 including an actuator body, such as an actuator rod 3156, that selectively moves the valve body assembly 3134 to the open position. The actuator rod 3156 preferably is operated by a control system of the humidifier 107 (e.g., the electronic master controller 125) to move the valve body assembly 3134 into the open position during normal operation of the humidifier 107. In the event of a malfunction of the primary valve 3112 or sensing of an undesirably high water level, the humidifier 107 can move the actuator rod 3156 to permit the valve body assembly 3134 to be moved to the closed position to close the secondary valve 3114. Preferably, when the secondary valve 3114 is in the closed position, no water is permitted to enter the humidification chamber 3102 through the dual valve arrangement 3110. In some configurations, a portion of the actuator rod 3156 is positioned outside of the humidification chamber 3102 and a portion that protrudes, in at least some positions of the actuator rod 3156, into the humidification chamber 3102. The humidification chamber body 3104 can include or carry a flexible membrane or seal element 3158 through which the actuator rod 3156 acts on the valve body assembly 3134. The seal element 3158 stretches to accommodate movement of the actuator rod 3156 toward the valve body assembly 3134. Thus, in such an arrangement, the actuator rod 3156 does not physically enter interior space of the humidification chamber 3102 because the seal element 3158 maintains a barrier between interior space of the humidification chamber 3102 and the actuator rod 3156. Although illustrated in a horizontal orientation, the actuator rod 3156 could be provided in other orientations, such as a vertical orientation, for example. In such an arrangement, the actuator rod 3156 could extend toward the valve body assembly 3134 from above.

Preferably, the humidifier 107 includes a water level sensing arrangement 3160 that senses a water level within the humidification chamber 3102. The humidifier 107 can use the water level information provided by the water level sensing arrangement 3160 to control the operation of the actuator arrangement 3154, in particular, the actuator rod 3156. In some configurations, the water level sensing arrangement 3160 includes a sensor 3162, which can be an optical sensor. The sensor 3162 can be configured to detect whether the water level is above or, alternatively, at or below a desired level. When the actual water level is above the desired water level, the sensor 3162 can provide a suitable signal (including the absence of a signal) to the control system of the humidifier 107, which can move the actuator rod 3156 (or other actuator arrangement 3154) to permit the valve body assembly 3134 to move to the closed position. If the actual water level is at or below the desired level, the sensor 3162 can provide a suitable signal (including the absence of a signal) to the control system of the humidifier 107, which can move the actuator rod 3156 (or other actuator arrangement 3154) to move the valve body assembly 3134 to the open position. In some configurations, the control system of the humidifier 107 moves the valve body assembly 3134 to the open position only if the humidifier 107 is provided with power or turned on, if the sensor 3162 is functional and if the water level is at or below the desired level. Suitable optical sensors can include, for example, LED or LDR sensors, or other sensor types that can detect the presence or absence of water within the humidification chamber 3102. Alternatively, the sensor 3162 can be or include a camera with a digital image processing, which can be incorporated in the control system of the humidifier 107, configured to detect the water level or determine a presence or absence of water at a particular level.

As described, the water inlet 3108 incorporates the dual valve arrangement 3110 which includes the first valve seat 3132 and the second valve seat 3138. The illustrated valve actuating mechanism includes the push rod 3124, which is situated within the co-axial outer cylindrical secondary push tube 3146. The push rod 3124 and secondary push tube 3146 are capable of moving freely and independently of one another. The end of the push rod 3124 facing the water inlet 3108 is tapered to a blunt point, which forms the valve body 3130. The valve body 3130 of the push rod 3124 and the valve body element 3136 of the secondary push tube 3146 are covered by a valve seal element 3164, which can be a flexible sealing membrane. Preferably, the valve seal element 3164 is configured to fit snugly over the rim of the secondary push tube 3146, thus coupling the secondary push tube 3146 to the push rod 3124 in a floating connection.

Thus, preferably, the valve seal element 3164 directly contacts the first valve seat 3132 and the second valve seat 3138 when the respective valve is in a closed position. In addition, the valve seal element 3164 can prevent water from entering the humidification chamber 3102 through the water inlet 3108 when the secondary valve system 3114 is closed regardless of the position of the primary valve system 3112. The valve seal element 3164 can be made of material that is supple but strong, for example, a medical grade silicone rubber material.

The humidification chamber 3102 is further equipped with an inlet port 3170 and an outlet port 3172. In the process of humidification, the heat transfer base 3106 of the humidification chamber 3102 is provided with heat from the humidifier 107, causing vapour to rise from the surface of the liquid water which mixes with the gases passing through the humidification chamber 3102. In humidifier designs utilizing a dual float arrangement, the secondary float is typically physically larger in size than the primary float and occupies a significant volume of a humidification chamber. The large size of the secondary float is useful in providing an increased closing force of the secondary valve. Elimination of the secondary float in the illustrated humidification chamber 3102 facilitates the provision of other advantageous features, at least some of which are described below.

In some configurations, the humidification chamber 3102 includes gas flow guiding features and/or surface area-enhancing features, such as one or more guide walls 3180 that can guide or direct a portion of the flow of gas within the humidification chamber 3102 between the inlet port 3170 and the outlet port 3172. In the illustrated arrangement, the humidification chamber 3102 comprises a plurality of guide walls 3180 spaced from one another to define one or more flow channels 3182. The guide walls 3180 can include internal guide walls and, in some configurations, the outer side walls of the humidification chamber body 3104 can form guide walls. In the illustrated arrangement, the guide walls 3180 are generally concentrically-arranged. In some configurations, the guide walls 3180 and/or flow channels 3182 can have varying heights/depths. In the illustrated arrangement, adjacent flow channels 3182 have different depths in an alternating fashion; with the shallow channels 3182 having about one-half the depth of the deep channels 3182. The widths of the flow channels 3182 can be generally the same or different depending on the desired flow characteristics. Preferably, the flow channels 3182 extend a substantial height of the interior space of the humidification chamber 3102 and can, but do not necessarily, contact the heat transfer base 3106 or other bottom surface of the humidification chamber 3102.

In the illustrated arrangement, the guide walls 3180 and flow channels 3182 are generally U-shaped when viewing the top of the humidification chamber 3102. The inlet port 3170 and the outlet port 3172 are located near respective ends of the U-shaped flow channels 3182. Preferably, the guide walls 3180 and flow channels 3182 extend along a substantial portion or a substantial entirety of a flow path between the inlet port 3170 and the outlet port 3172. The illustrated flow channels 3182 are configured to provide for parallel flow through the channels 3182. That is, a flow of gases entering the humidification chamber 3102 is divided amongst the available flow channels 3182. However, in other arrangements, the flow channels 3182 could be arranged in series such that a flow of gases through the humidification chamber 3102 passes through multiple or all of the available flow channels 3182 in serial fashion to increase residence time within the humidification chamber 3102. Thus, the guide walls 3180 can be configured to define a tortuous flow path through the humidification chamber 3102. Advantageously, the guide walls 3180 provide additional surface area for the placement of any of the microstructures described herein to increase the total surface area of water available to the flow of gas through the humidification chamber 3102. In addition, one or more walls of the humidification chamber 3102 (e.g., internal guide walls 3180 and/or external walls) can comprise walls configured to be heated by a heater base of the humidifier 107. The humidification chamber 3102 can comprise walls configured to be heated by a heating member distinct from the humidifier 107. The humidification chamber 3102 can further comprise insulation disposed at least on or over a wall of the humidification chamber 3102 near the evaporator portion. In some configurations, the walls 3180 can be provided primarily or entirely to increase the surface area for microstructures and provide little or no guiding of the gas flow.

As illustrated, the inlet port 3170 and the outlet port 3172 can be located on opposite sides of the dual valve arrangement 3110. The guide walls 3180 facilitate desired flow of the gases through the humidification chamber 3102 between the inlet port 3170 and the outlet port 3172 such that the inlet port 3170 and the outlet port 3172 can be positioned relative to the overall humidification chamber 3102 as desired, such as at or near a wall of the humidification chamber body 3104. For example, the inlet port 3170 and/or the outlet port 3172 can be positioned at or near, for example, a rear wall 3184 of the humidification chamber body 3104. In the illustrated arrangement, the rear wall 3184 is generally planar, which can facilitate, make practical or make possible the use of the optical (or other) sensor 3162. In addition, the provision of guide walls 3180 can make possible or practical the use of shapes for the humidification chamber body 3104 other than generally cylindrical, which can increase the available surface area of the water within the humidification chamber 3102 and/or can increase the surface area of the heat transfer base 3106 for more efficient heating of the water within the humidification chamber 3102.

Turbine for Use in Humidification Chamber

With reference to FIGS. 34-37, in the alternative of, or in addition to, the guide walls 3180, the humidification chamber 3102 can include other structures that increase surface area available for microstructures and/or facilitate mixing of the gas and liquid phases of the water within the humidification chamber 3102. For example, in some configurations, elimination of the secondary float provides room within the humidification chamber 3102 for a mixing element or structure 3186 that facilitates mixing of the gas and liquid phases of the water within the humidification chamber 3102. In the illustrated arrangement, the mixing element 3186 is a turbine that is rotatable within and relative to the humidification chamber 3102. In alternative arrangements, the turbine or other mixing structure 3186 could form a portion of or otherwise be integrated with a secondary float and/or could be stationary instead of movable. In other arrangements, as described above, any type or combination of valve actuation arrangements for the dual valve arrangement 3110 can be used, including float controlled valves and sensor/actuator controlled valves, for example and without limitation. Stationary mixing structures 3186 could be supported on a bottom surface of the humidification chamber 3102 or could be supported or made integral with the humidification chamber body 3104, such as extending downwardly from an upper wall of the humidification chamber body 3104, for example.

Preferably, the turbine 3186 comprises a plurality of blades 3188 secured to a base 3190. In the illustrated arrangement, the blades 3188 are separate from the base 3190 and held in place by a plurality of tabs 3192, which may provide a snap-fit arrangement with the blades 3188. Other suitable methods or mechanisms for securing the blades 3188 to the base 3190 can also be used, including forming the blades 3188 and base 3190 together as a unitary structure. The blades 3188 can be arranged radially on the base 3190 or can be offset from a radial alignment, as illustrated. In some configurations, the blades 3188 can be tilted or otherwise angled relative to an axis of rotation of the turbine 3186 in a vertical direction. The illustrated blades 3188 are generally or substantially planar, which can be advantageous in permitting the formation of microstructures, as described herein. However, in other configurations, the blades 3188 can be curved in a width and/or length direction.

In some configurations, the turbine 3186 can be rotatable in response to a flow of gas through the humidification chamber 3102. In other configurations, other types of movable mixing elements 3186 can be movable in response to a flow of gas through the humidification chamber 3102. In the illustrated arrangement, the turbine 3186 is positioned within a flow path of gases moving through the humidification chamber 3102. If desired, guide walls 3180 or other guide structures can also be provided to facilitate the flow of gas into or out of the turbine 3186. As described, the turbine 3186 can facilitate mixing of gaseous and liquid phases of water, which allows more moisture and heat to be extracted from the humidification chamber 3102 due to the more homogenous temperature mix. It is contemplated that even a low rotational speed of the turbine 3186 or other mixing element will result in advantageous mixing of the liquid and gas phases.

The inlet port 3170 and the outlet port 3172 can be positioned to facilitate or direct a desired flow path of gases moving through the humidification chamber 3102. For example, as illustrated, the inlet port 3170 and the outlet port 3172 can be positioned on opposing sides of the water inlet 3108 and the dual valve arrangement 3110 at or near a planar wall 3184 of the humidification chamber 3102. Although illustrated in a horizontal plane, the inlet port 3170 and the outlet port 3172 can be oriented in a vertical direction or other direction, as desired. In such an arrangement, the inlet port 3170 and the outlet port 3172 can be generally or substantially tangential with respect to the turbine 3186. In other arrangements, the inlet port 3170 and the outlet port 3172 can be generally or substantially radially oriented with respect to the turbine 3186, as illustrated in broken lines.

Alternatively, the inlet port 3170 can be positioned generally along the axis of rotation of the turbine 3186, such as positioned above the turbine 3186. In such an arrangement, the flow of gas enters the central portion of the turbine 3186 and flows outwardly between the blades 3188 to the outlet port 3172. In configurations with non-rotational mixing elements 3186, the flow of gas can be directed to a particular location (e.g., center) of the mixing element 3186 and dispersed as desired (e.g., outwardly) by the mixing element 3186.

Preferably, the turbine 3186 is supported for rotation relative to the humidification chamber 3102 in a manner to minimize resistance to rotation. For example, the turbine 3186 can be configured to float on the water within the humidification chamber 3102 at least slightly above the bottom surface of the humidification chamber 3102 (e.g., the heat transfer base 3106). The bottom surface of the turbine 3186 can be provided with a projection 3194 (e.g., a pointed or conical projection) to reduce or minimize friction in the event that the turbine 3186 contacts a surface of the humidification chamber 3102. In other arrangements, the turbine 3186 could be configured such that the projection 3194 intentionally contacts or rests upon a surface of the humidification chamber 3102.

Preferably, a desirable water level within the humidification chamber 3102 is above the base 3190 of the turbine 3186 such that liquid water is in contact with the lower portions of the blades 3188 to facilitate wicking of the water vertically on the blades 3188 via the microstructures, as described herein. To avoid significantly impeding rotation of the turbine 3186, the desirable or normal water level 3196 can be slightly above the upper surface of the base 3190, such as at or below the tabs 3192, for example and without limitation. Preferably, the desirable or normal water level 3196 is selected to be sufficiently high to facilitate or achieve a desirable amount of wicking of the water up the blades 3188 without unduly impeding rotation of the turbine 3186.

Patient Interface with Microstructures

Condensate management is an important issue in the design of patient interfaces design. Accordingly, certain embodiments include the realization that microstructures can be incorporated into patient interfaces, including, without limitation, masks (such as tracheal mask, face masks and nasal masks), cannulas, and nasal pillows.

Figure 10A:
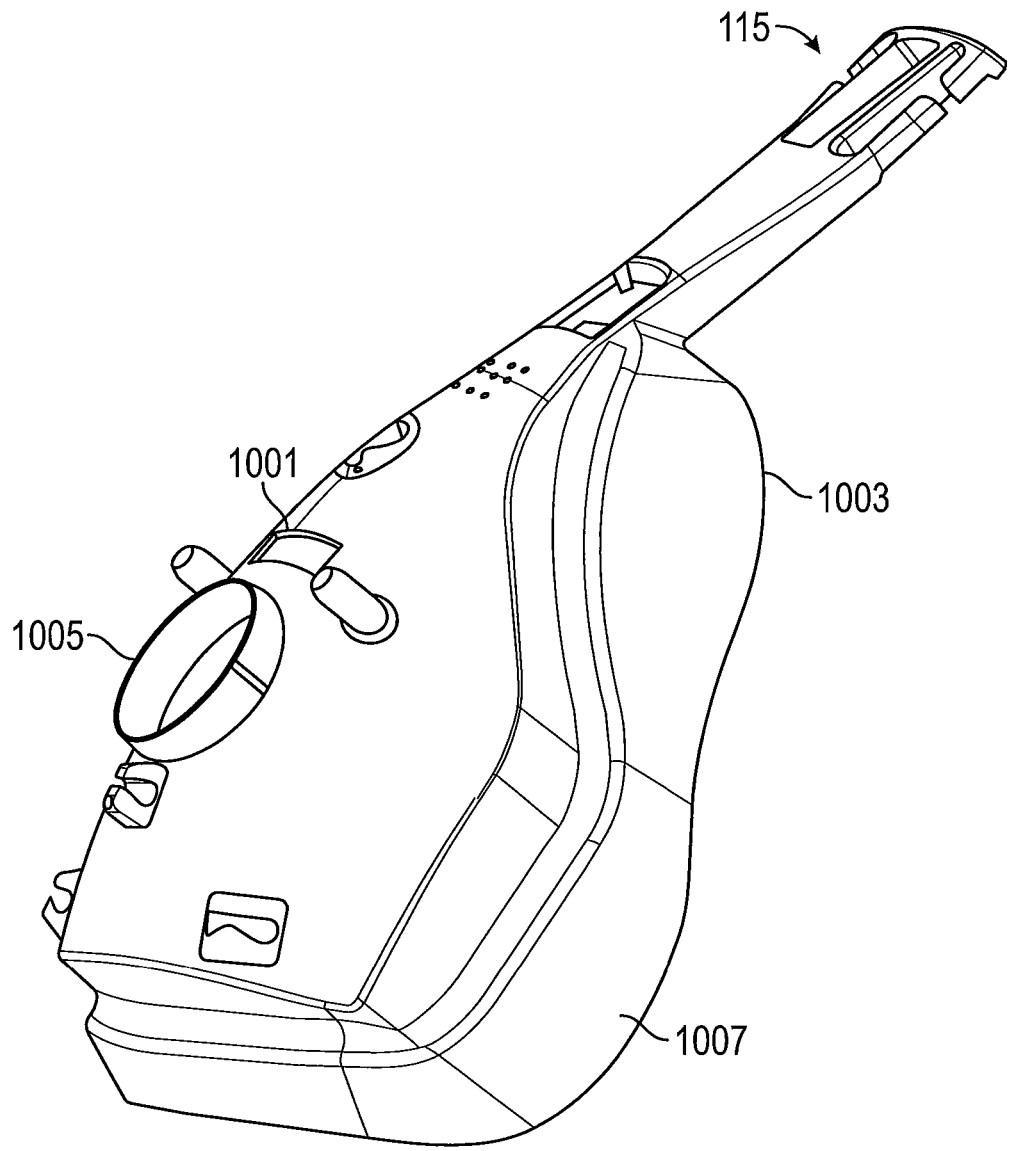
FIG. 10A shows a front perspective view of an example patient interface.

FIG. 10A shows a front perspective view of an example of the patient interface 115. The patient interface 115 can be used in the field of respiratory therapy. The patient interface 115 has particular utility with forms of positive pressure respiratory therapy. For example, the patient interface 115 can be used for administering continuous positive airway pressure ("CPAP") treatments. In addition, the patient interface 115 can be used with variable positive airway pressure ("VPAP") treatments and bi-level positive airway pressure ("BiPAP") treatments. The patient interface 115 can be used with any suitable CPAP system.

The patient interface 115 can comprise any suitable mask configuration. For example, certain features, aspects and advantages of the present invention can find utility with nasal masks, full face masks, oronasal masks or any other positive pressure mask. The illustrated interface is a full face mask 1001. The mask 1001 generally comprises a mask assembly 1003 and a connection port assembly 1005. The mask assembly 1003 generally comprises a mask seal 1007 that, in use, contacts a user's face.

Figure 10B:
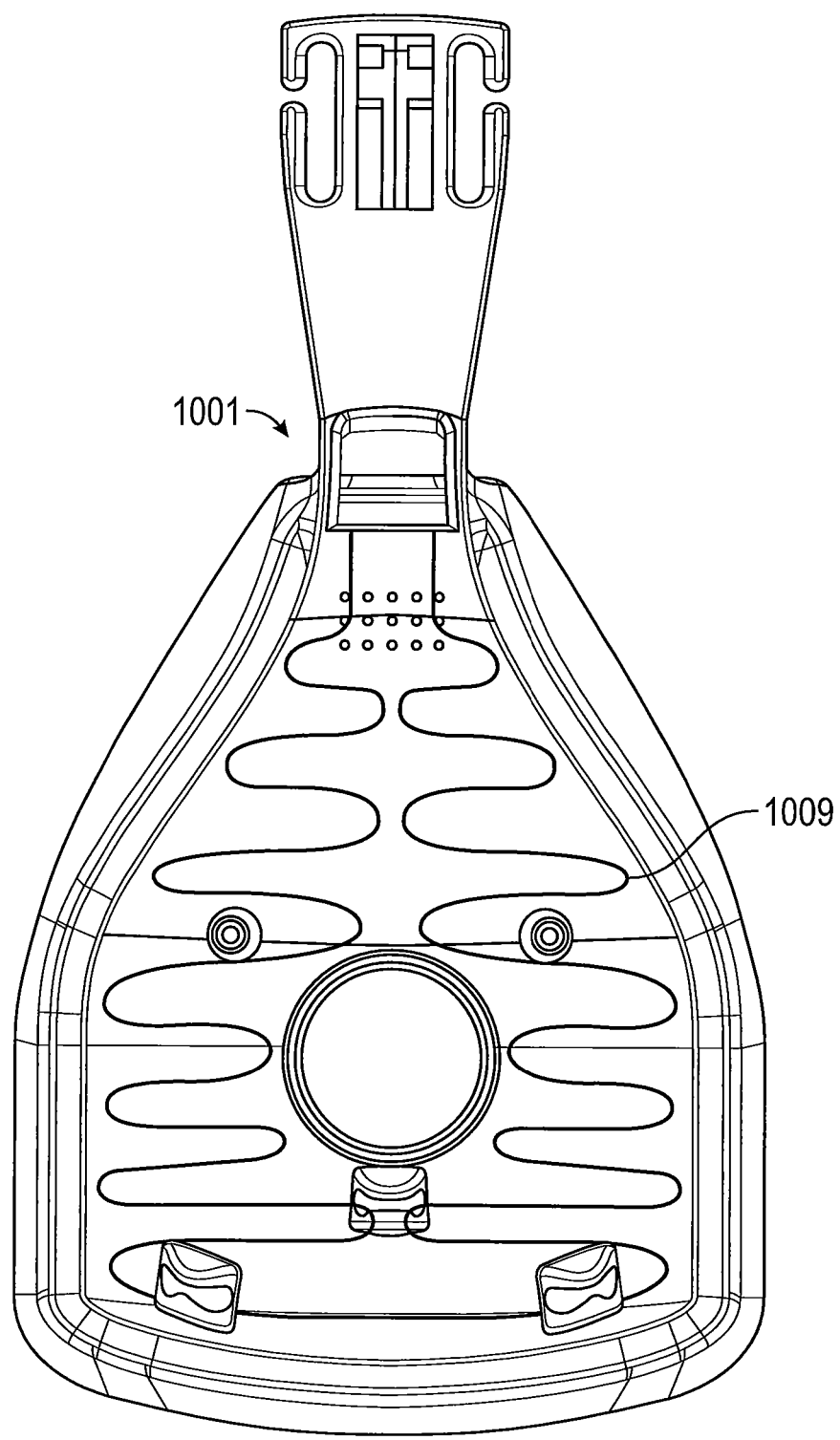
FIG. 10B shows a front plan view of an example patient interface incorporating a conductive filament.

FIG. 10B illustrates a configuration of the mask 1001 of FIG. 10A incorporating one or more conductive filaments 1009. As shown in FIG. 10B, the conductive filaments 1009 can be arranged in a generally sinuous pattern. However, a variety of configurations are possible, such as a grid-shaped configuration, a coil, or a ring.

The one or more conductive filaments 1009 can be attached to an outer surface of the mask 1001 wall (that is, the surface of the mask 1001 configured to face the ambient air during use). The one or more conductive filaments 1009 can also be attached to an inner surface of the mask 1001 wall (that is, the surface of the mask 1001 configured to face the patient during use). The one or more conductive filaments 1009 can also be embedded or otherwise incorporated in the mask 1001 wall. The last configuration can be desirable because it can prevent a patient from touching the conductive filaments 1009. A combination of the foregoing configurations can also be incorporated in the mask 1001. Moreover, the mask 1001 wall itself, or at least a portion of the mask 1001 wall, can be conductive. For example, the mask 1001 can comprise a conductive polymer or a conductive metal.

Figure 11A:
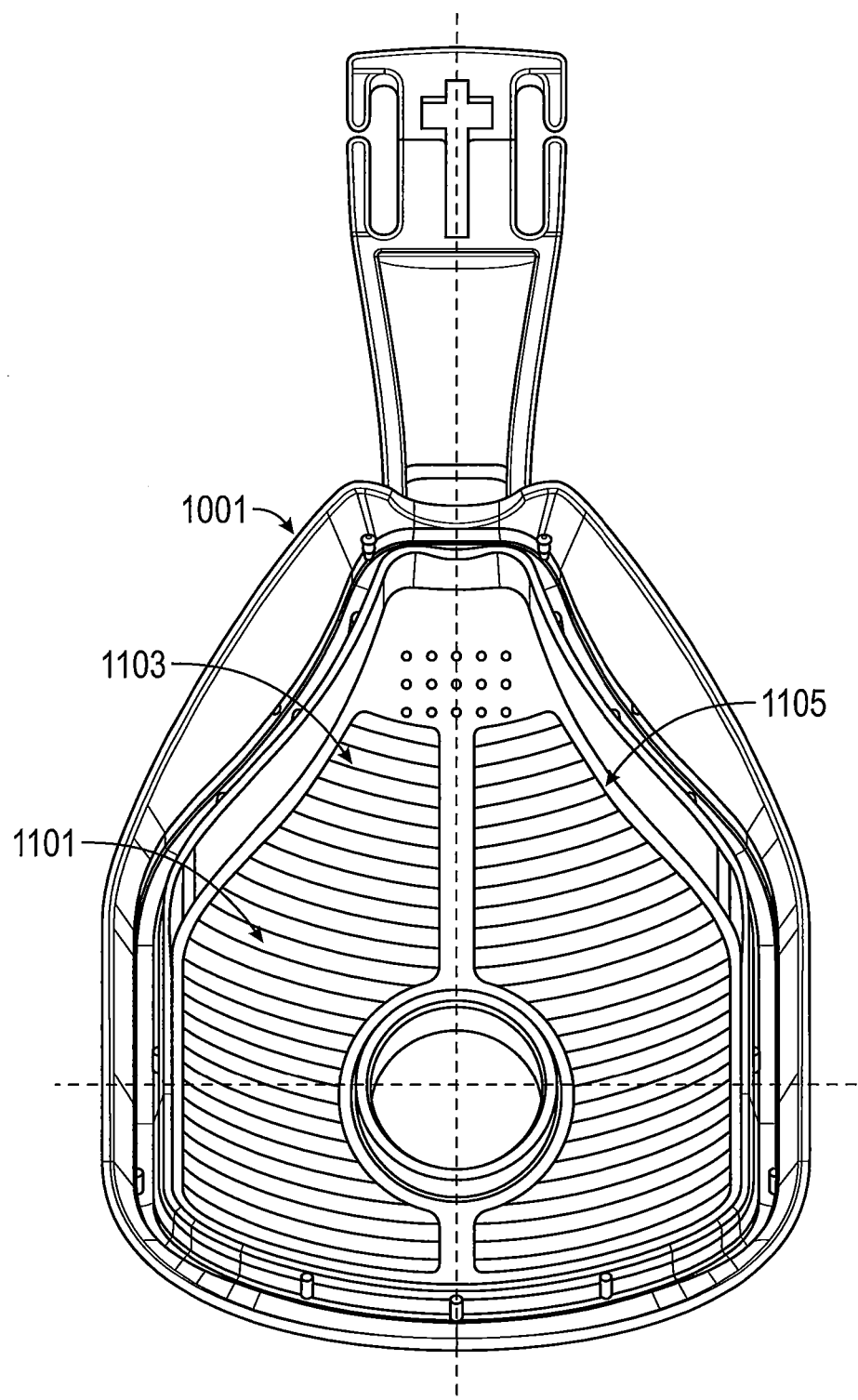
FIG. 11A shows a rear plan view of an example patient interface including microstructures.

FIG. 11A is a rear elevation view of the mask 1001 of FIG. 10. FIG. 11A generally illustrates an example configuration for microstructures 1101 on the inside surface of the mask. The properties of the microstructures 1101 discussed in the preceding sections are incorporated by reference. The example mask 1001 has a longitudinal axis LA and a transverse axis TA. The mask 1001 comprises a first portion 1103 on one side of the longitudinal axis LA and a second portion 1105 on the other side of the longitude axis LA. In general, the microstructures 1101 extend along the underside of the mask 1001 parallel the transverse axis TA. The microstructures 1101 on either side of the longitudinal axis LA form mirror image patterns. The microstructures 1101 are not drawn to scale and are for illustrative purposes only.

Figure 11B:
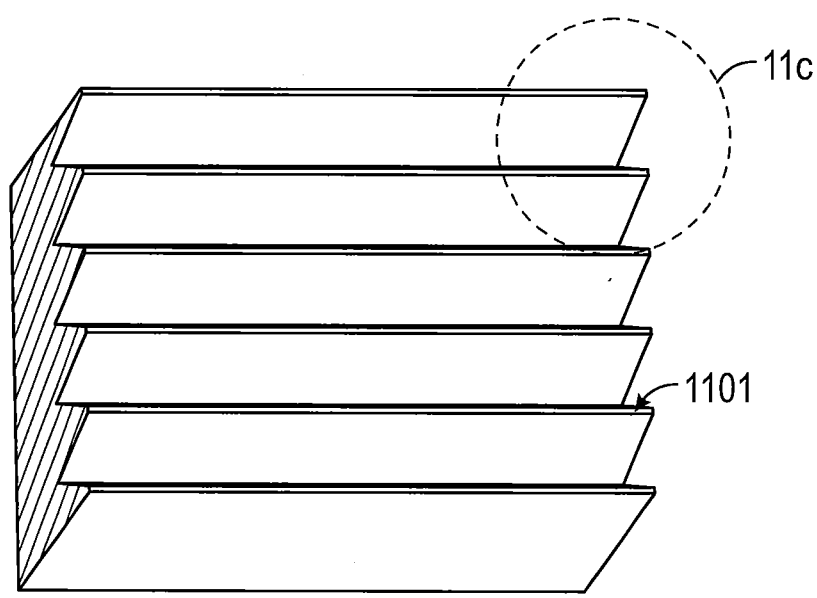
FIG. 11B shows a perspective view of a magnified portion of the microstructures in FIG. 11A.
Figure 11C:
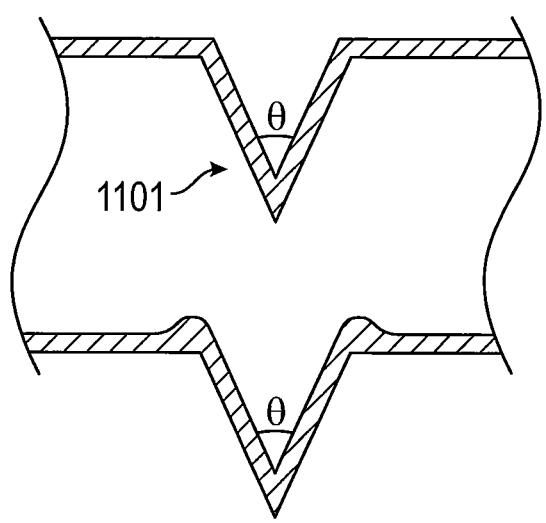
FIG. 11C shows a cross section of an example microstructure.

FIG. 11B shows a first magnified view of a portion of the microstructures 1101 of FIG. 11A. FIG. 11C illustrates a cross section of an example one of the microstructures 1101. In this example embodiment, the microstructure is a microchannel. The microstructures can be similar to those discussed above, and the discussion of their shapes and properties is incorporated by reference here.

As explained below, certain embodiments include the realization that incorporating microstructures in a patient interface can improve condensate management by preventing or reducing formation of macroscale water droplets (that is, water droplets having a diameter greater than 1000 μm (or about 1000 μm). FIG. 12A shows a schematic of water droplet formation on an interface surface that does not incorporate microstructures. In contrast, FIG. 12B shows a schematic of water spreading on an interface surface that does incorporate microstructures. In both figures, 1201 designates the outer surface of the interface (that is, the surface of the interface configured to face the ambient air during use), and 1203 designates the inner surface of the interface (that is, the surface of the interface configured to face the patient during use).

Patient interfaces experience very high humidity conditions. As shown in boxes 1205 and 1207, water droplets can readily form on the inner surface of a patient interface when the inner surface 1203 of the interface is smooth (or relatively smooth). As shown in box 1209, in use, these water droplets will run down to a lower area of the patient interface and pool together or drip onto a patient's face. As shown in boxes 1211 through 1213, the incorporation of microstructures on the inner surface 1203 of a patient interface can ameliorate this problem. As shown in boxes 1211 and 1213, the microstructures spread out the condensate along the length (or at least a portion of the length) of the microstructures, which prevents the condensate from forming droplets. As shown in box 1215, because condensate spreads out along the microstructures over a large surface area, the condensate can evaporate more readily. This spreading action also decreases the likelihood that condensate will pool in a lower area or drop on the patient's face. In certain embodiments, incorporation of microstructures on the inner surface 1203 allows condensate to be redirected from the patient interface onto an absorbent layer (not shown), such as a sponge or breathable membrane.

Figure 11D:
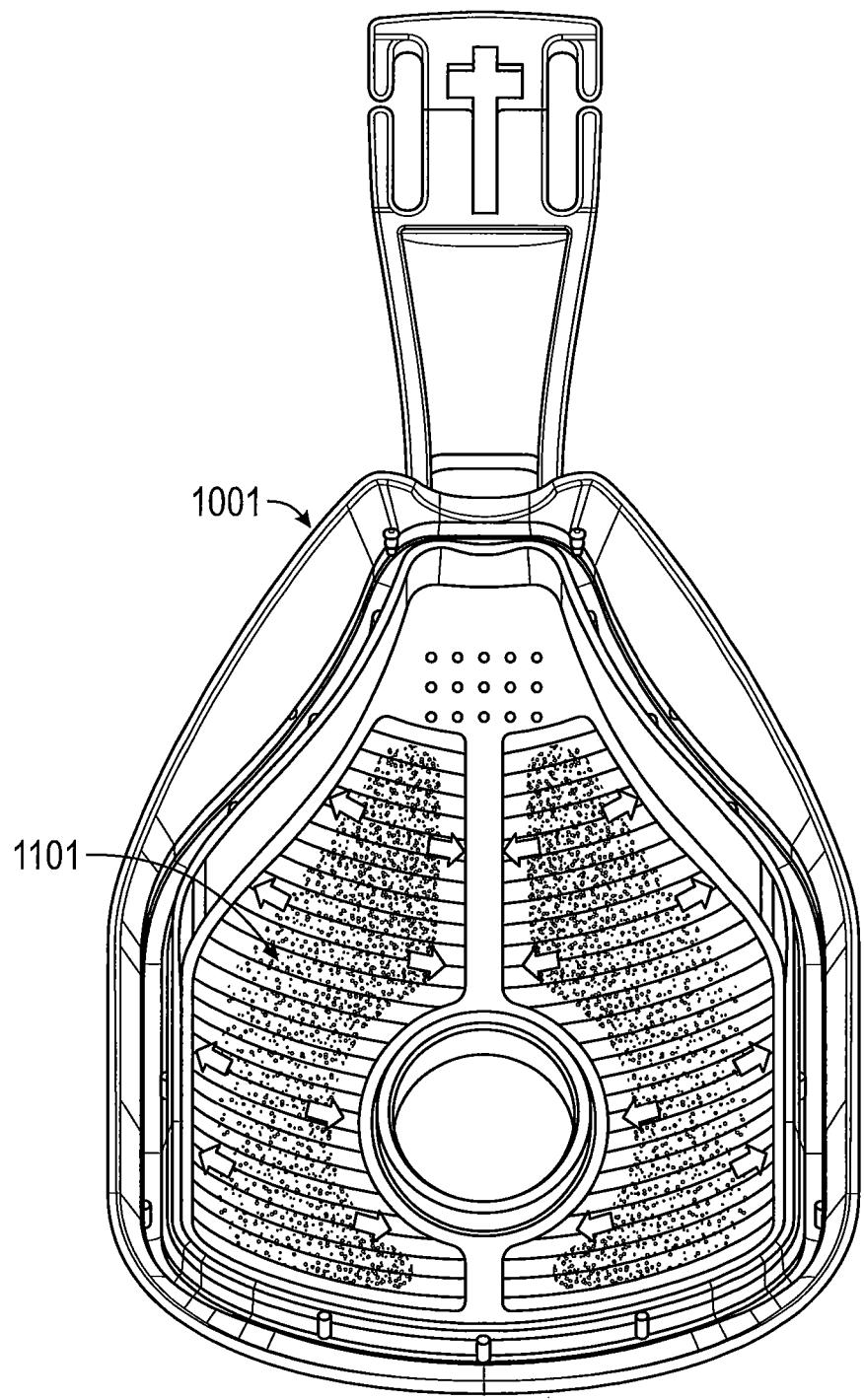
FIG. 11D shows a rear plan view of an example patient interface including microstructures.

FIG. 11D shows a rear elevation view of the mask 1001 of FIG. 10A. FIG. 11D schematically illustrates condensate spreading out along the microstructures 1101 on the inner surface of the mask.

In at least some configurations, the one or more conductive filaments 1009 (FIG. 10B) comprise one or more heating filaments configured to heat the mask 1001 wall. When the one or more conductive filaments 1009 comprise at least one heating filament, the heating filament can be connected to an electrical supply and thereby apply heat to the mask 1001 body. As shown in FIG. 13, the added heat speeds evaporation of condensate spread out in or on the microstructures.

The foregoing description of the invention includes preferred forms thereof. Modifications may be made thereto without departing from the scope of the invention. To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

What is claimed is:

1. A humidification chamber suitable for use with a humidifier, the humidification chamber comprising:
    a reservoir portion configured to hold a liquid;
    an evaporator portion adjacent the reservoir portion configured to facilitate evaporation of the liquid;
    a microstructured surface configured to transport liquid from the reservoir portion to the evaporator portion; and
    a plurality of spaced apart, arcuate and nested guide walls configured to guide a flow of gases within the humidification chamber.

2. The humidification chamber of claim 1, wherein the evaporator portion is heatable.

3. The humidification chamber of claim 1, wherein the microstructured surface comprises microchannels having an aspect ratio that is lower near the reservoir portion and higher near the evaporator portion such that the aspect ratio increases along a gradient.

4. The humidification chamber of claim 1, wherein the microstructured surface comprises first microchannels extending generally horizontally near the reservoir portion and second microchannels extending generally vertically near the evaporator portion, wherein the first microchannels are configured to transport liquid to the second microchannels.

5. The humidification chamber of claim 1, wherein the microstructured surface forms at least a portion of an inner wall of the humidification chamber.

6. The humidification chamber of claim 1, wherein the humidification chamber comprises walls configured to be heated by a heater base of the humidifier.

7. The humidification chamber of claim 1, wherein the humidification chamber comprises walls configured to be heated by a heating member distinct from the humidifier.

8. The humidification chamber of claim 1, further comprising insulation disposed at least on or over a wall of the humidification chamber near the evaporator portion.

9. The humidification chamber of claim 1, wherein the at least one arcuate internal guide wall is generally U-shaped and extend between an inlet port and an outlet port of the humidification chamber.

10. The humidification chamber of claim 1, further comprising a mixing element within the humidification chamber that is configured to facilitate mixing of gas and liquid.

11. The humidification chamber of claim 1, wherein the humidification chamber comprises an inlet port and an outlet port.

12. A humidification chamber suitable for use with a humidifier, the humidification chamber comprising:
    a reservoir portion configured to hold a liquid;
    an evaporator portion adjacent the reservoir portion configured to facilitate evaporation of the liquid;
    a microstructured surface configured to transport liquid from the reservoir portion to the evaporator portion; and
    at least one arcuate internal guide wall configured to guide a flow of gases within the humidification chamber, wherein the microstructured surface is located on a separate sheet which is adhered to at least a portion of the at least one arcuate internal guide wall.

13. The humidification chamber of claim 12, wherein the evaporator portion is heatable.

14. The humidification chamber of claim 12, wherein the microstructured surface comprises microchannels having an aspect ratio that is lower near the reservoir portion and higher near the evaporator portion such that the aspect ratio increases along a gradient.

15. The humidification chamber of claim 12, wherein the microstructured surface comprises first microchannels extending generally horizontally near the reservoir portion and second microchannels extending generally vertically near the evaporator portion, wherein the first microchannels are configured to transport liquid to the second microchannels.

16. The humidification chamber of claim 12, wherein the microstructured surface forms at least a portion of an inner wall of the humidification chamber.

17. The humidification chamber of claim 12, wherein the humidification chamber comprises walls configured to be heated by a heater base of the humidifier.

18. The humidification chamber of claim 12, wherein the humidification chamber comprises walls configured to be heated by a heating member distinct from the humidifier.

19. The humidification chamber of claim 12, further comprising insulation disposed at least on or over a wall of the humidification chamber near the evaporator portion.

20. The humidification chamber of claim 12, wherein the at least one arcuate internal guide wall comprises a plurality of guide walls.

21. The humidification chamber of claim 12, wherein the sheet is flexible.

22. The humidification chamber of claim 1, wherein a flow channel is defined between adjacent ones of the plurality of spaced apart, arcuate and nested guide walls and the plurality of spaced apart, arcuate and nested guide walls defines multiple flow channels.

23. The humidification chamber of claim 22, wherein at least some of the flow channels vary in size relative to one another.

24. The humidification chamber of claim 1, wherein the plurality of spaced apart, arcuate and nested guide walls are arranged concentrically.

25. The humidification chamber of claim 1, wherein the microstructured surface is integrally formed on a guide wall of the plurality of spaced apart, arcuate and nested guide walls.

* * * * *